United States Patent
Zenhausern et al.

(10) Patent No.: US 8,640,555 B2
(45) Date of Patent: Feb. 4, 2014

(54) PERFORMANCE

(75) Inventors: Frederic Zenhausern, Fountain Hills, AZ (US); Alan Nordquist, Payson, AZ (US); Ralf Lenigk, Chandler, AZ (US); Cedric Hurth, Tempe, AZ (US); Jianing Yang, Tempe, AZ (US); Xiaojia Chen, Chandler, AZ (US); John Lee-Edghill, Birmingham (GB); Nina Moran, Birmingham (GB); Andrew Hopwood, Birmingham (GB); Pieris Koumi, Birmingham (GB)

(73) Assignee: BioAccel, Phoenix, AZ (US)

( * ) Notice: Subject to any disclaimer, the term of this patent is extended or adjusted under 35 U.S.C. 154(b) by 543 days.

(21) Appl. No.: 12/703,025

(22) Filed: Feb. 9, 2010

(65) Prior Publication Data

US 2011/0100101 A1    May 5, 2011

Related U.S. Application Data

(60) Provisional application No. 61/151,107, filed on Feb. 9, 2009, provisional application No. 61/151,117, filed on Feb. 9, 2009, provisional application No. 61/151,104, filed on Feb. 9, 2009, provisional application No. 61/151,111, filed on Feb. 9, 2009.

(51) Int. Cl.
*G01N 1/22* (2006.01)

(52) U.S. Cl.
USPC ...................................................... 73/863.11

(58) Field of Classification Search
USPC ...................................................... 73/863.11
See application file for complete search history.

(56) References Cited

U.S. PATENT DOCUMENTS

| | | |
|---|---|---|
| 3,981,956 A | 9/1976 | Redmer et al. |
| 4,683,195 A | 7/1987 | Mullis et al. |
| 4,683,202 A | 7/1987 | Mullis |
| 5,409,586 A | 4/1995 | Kamahori et al. |
| 5,519,635 A | 5/1996 | Miyake et al. |
| 5,538,848 A | 7/1996 | Livak et al. |
| 5,578,832 A | 11/1996 | Trulson et al. |
| 5,631,734 A | 5/1997 | Stern et al. |
| 5,834,758 A | 11/1998 | Trulson et al. |
| 5,856,174 A | 1/1999 | Lipshutz et al. |
| 5,922,591 A | 7/1999 | Anderson et al. |

(Continued)

FOREIGN PATENT DOCUMENTS

| | | |
|---|---|---|
| EP | 0 421 595 A2 | 8/1990 |
| EP | 0 512 334 A2 | 11/1992 |

(Continued)

OTHER PUBLICATIONS

U.S. Appl. No. 61/151,104, filed Feb. 9, 2009. (Zenhausern et al.).

(Continued)

*Primary Examiner* — Hezron E Williams
*Assistant Examiner* — Rodney T Frank
(74) *Attorney, Agent, or Firm* — Merchant & Gould P.C.

(57) ABSTRACT

Instruments, devices and methods of analysis are provided which fully integrate a significant number of process steps in a continuous operation. Accurate positioning and full contact between components is also provided by the relative movement the designs allow. An effect interface between a low cost disposable cartridge or device and the instrument to process it is also detailed.

22 Claims, 39 Drawing Sheets

(56) References Cited

U.S. PATENT DOCUMENTS

| | | | |
|---|---|---|---|
| 5,928,907 A | 7/1999 | Woudenberg et al. | |
| 5,972,716 A | 10/1999 | Ragusa et al. | |
| 6,004,821 A | 12/1999 | Levine et al. | |
| 6,007,690 A | 12/1999 | Nelson et al. | |
| 6,025,601 A | 2/2000 | Trulson et al. | |
| 6,043,080 A | 3/2000 | Lipshutz et al. | |
| 6,090,555 A | 7/2000 | Fiekowsky et al. | |
| 6,141,096 A | 10/2000 | Stern et al. | |
| 6,171,793 B1 | 1/2001 | Phillips et al. | |
| 6,185,030 B1 | 2/2001 | Overbeck | |
| 6,197,595 B1 | 3/2001 | Anderson et al. | |
| 6,201,639 B1 | 3/2001 | Overbeck | |
| 6,207,960 B1 | 3/2001 | Stern | |
| 6,225,625 B1 | 5/2001 | Pirrung et al. | |
| 6,242,235 B1 | 6/2001 | Shultz et al. | |
| 6,252,236 B1 | 6/2001 | Trulson et al. | |
| 6,262,838 B1 | 7/2001 | Montagu | |
| 6,270,644 B1 | 8/2001 | Mathies et al. | |
| 6,294,327 B1 | 9/2001 | Walton et al. | |
| 6,335,824 B1 | 1/2002 | Overbeck | |
| 6,372,106 B1 | 4/2002 | Johnson et al. | |
| 6,399,365 B2 | 6/2002 | Besemer et al. | |
| 6,403,320 B1 | 6/2002 | Read et al. | |
| 6,403,957 B1 | 6/2002 | Fodor et al. | |
| 6,407,858 B1 | 6/2002 | Montagu | |
| 6,416,952 B1 | 7/2002 | Pirrung et al. | |
| 6,440,725 B1* | 8/2002 | Pourahmadi et al. | 435/288.5 |
| 6,472,671 B1 | 10/2002 | Montagu | |
| 6,489,111 B1 | 12/2002 | Takahashi et al. | |
| 6,490,533 B2 | 12/2002 | Weiner et al. | |
| 6,491,871 B1 | 12/2002 | Fodor et al. | |
| 6,521,181 B1 | 2/2003 | Northrup et al. | |
| 6,545,264 B1 | 4/2003 | Stern | |
| 6,551,841 B1 | 4/2003 | Wilding et al. | |
| 6,554,986 B1 | 4/2003 | Mathies et al. | |
| 6,576,424 B2 | 6/2003 | Fodor et al. | |
| 6,597,000 B2 | 7/2003 | Stern | |
| 6,604,902 B2 | 8/2003 | Norris et al. | |
| 6,611,767 B1 | 8/2003 | Fiekowsky et al. | |
| 6,643,015 B2 | 11/2003 | Weiner | |
| 6,643,076 B2 | 11/2003 | Montagu | |
| 6,646,243 B2 | 11/2003 | Pirrung et al. | |
| 6,650,411 B2 | 11/2003 | Odoy et al. | |
| 6,670,122 B2 | 12/2003 | Rosenow et al. | |
| 6,720,149 B1 | 4/2004 | Rava et al. | |
| 6,741,344 B1 | 5/2004 | Stern et al. | |
| 6,813,567 B2 | 11/2004 | Weiner et al. | |
| 6,818,185 B1 | 11/2004 | Petersen et al. | |
| 6,902,900 B2 | 6/2005 | Davies et al. | |
| 6,942,971 B2 | 9/2005 | McMillan et al. | |
| 7,022,473 B1 | 4/2006 | Tanga et al. | |
| 7,029,881 B1 | 4/2006 | Takahashi et al. | |
| 7,081,226 B1 | 7/2006 | Wittwer et al. | |
| 7,097,973 B1 | 8/2006 | Zenhausern | |
| 7,118,867 B2 | 10/2006 | Tabiti et al. | |
| 7,172,897 B2* | 2/2007 | Blackburn et al. | 435/287.2 |
| 8,101,244 B2* | 1/2012 | Clarke et al. | 427/427.2 |
| 2002/0123059 A1 | 9/2002 | Ho | |
| 2002/0141903 A1* | 10/2002 | Parunak et al. | 422/101 |
| 2003/0022231 A1 | 1/2003 | Wangh et al. | |
| 2003/0102221 A1 | 6/2003 | Ozawa et al. | |
| 2003/0113906 A1 | 6/2003 | Sangha et al. | |
| 2003/0119004 A1 | 6/2003 | Wenz et al. | |
| 2003/0159999 A1 | 8/2003 | Oakley et al. | |
| 2003/0190608 A1 | 10/2003 | Blackburn | |
| 2004/0034211 A1 | 2/2004 | Gjerde et al. | |
| 2004/0043479 A1 | 3/2004 | Briscoe et al. | |
| 2004/0063137 A1 | 4/2004 | Kurane et al. | |
| 2004/0086870 A1 | 5/2004 | Tyvoll et al. | |
| 2004/0086872 A1 | 5/2004 | Childers et al. | |
| 2004/0096819 A1 | 5/2004 | McMillan et al. | |
| 2004/0115094 A1 | 6/2004 | Gumbrecht et al. | |
| 2004/0209354 A1 | 10/2004 | Mathies et al. | |
| 2004/0257906 A1 | 12/2004 | Scriba et al. | |
| 2005/0053952 A1 | 3/2005 | Hong et al. | |
| 2005/0176037 A1 | 8/2005 | Mastromatteo et al. | |
| 2005/0191686 A1 | 9/2005 | Han et al. | |
| 2005/0220677 A1 | 10/2005 | Sangha | |
| 2005/0238535 A1 | 10/2005 | Knezevic et al. | |
| 2005/0243304 A1 | 11/2005 | Padmanabhan et al. | |
| 2005/0255516 A1 | 11/2005 | McMillan et al. | |
| 2006/0011539 A1 | 1/2006 | Lee et al. | |
| 2006/0014186 A1 | 1/2006 | Hodge et al. | |
| 2006/0014200 A1* | 1/2006 | McMillan et al. | 435/6 |
| 2006/0084185 A1 | 4/2006 | Landers et al. | |
| 2006/0099620 A1 | 5/2006 | Walker et al. | |
| 2006/0194308 A1 | 8/2006 | Gutekunst et al. | |
| 2006/0260941 A1 | 11/2006 | Tan et al. | |
| 2006/0286606 A1 | 12/2006 | Oliver | |
| 2007/0003955 A1 | 1/2007 | Novoradovskaya et al. | |
| 2007/0128612 A1 | 6/2007 | Povlich | |
| 2007/0184456 A1 | 8/2007 | Chee et al. | |
| 2007/0265439 A1 | 11/2007 | Gumbrecht et al. | |
| 2008/0038740 A1 | 2/2008 | Reed et al. | |
| 2008/0063573 A1* | 3/2008 | Ammann et al. | 422/105 |
| 2008/0182301 A1* | 7/2008 | Handique et al. | 435/91.2 |
| 2008/0229849 A1* | 9/2008 | Doebler et al. | 73/864.91 |
| 2009/0203022 A1 | 8/2009 | Zenhausern et al. | |

FOREIGN PATENT DOCUMENTS

| | | |
|---|---|---|
| EP | 0 854 362 A2 | 7/1998 |
| EP | 1 312 684 A2 | 5/2003 |
| EP | 1 385 006 A2 | 7/2003 |
| EP | 1 445 020 A1 | 8/2004 |
| EP | 1 467 202 A2 | 10/2004 |
| EP | 1 526 372 A2 | 4/2005 |
| EP | 1 681 557 A1 | 7/2006 |
| JP | 2006-112928 | 4/2006 |
| KR | 10-2001-0040747 | 5/2001 |
| KR | 10-2002-0008402 | 1/2002 |
| KR | 10-2006-0094543 | 8/2006 |
| WO | WO 92/21780 | 12/1992 |
| WO | WO 96/09407 | 3/1996 |
| WO | WO 99/10735 | 3/1999 |
| WO | WO 00/62931 | 4/2000 |
| WO | WO 00/72970 A1 | 12/2000 |
| WO | WO 00/78454 A1 | 12/2000 |
| WO | WO 01/02846 A1 | 1/2001 |
| WO | WO 01/17683 A2 | 3/2001 |
| WO | WO 02/052030 A2 | 7/2002 |
| WO | WO 02/075312 A1 | 9/2002 |
| WO | WO 02/093153 A1 | 11/2002 |
| WO | WO 03/050308 A1 | 6/2003 |
| WO | WO 03/089669 A1 | 10/2003 |
| WO | WO 2004/040001 A2 | 5/2004 |
| WO | WO 2004/055509 A2 | 7/2004 |
| WO | WO 2005/003384 A1 | 1/2005 |
| WO | WO 2005/024010 A1 | 3/2005 |
| WO | WO 2006/032044 A2 | 3/2006 |
| WO | WO 2006/039293 | 4/2006 |
| WO | WO 2006/059132 A1 | 6/2006 |
| WO | WO 2006/103440 A2 | 10/2006 |
| WO | WO 2007/002490 | 1/2007 |
| WO | WO 2007/047336 A2 | 4/2007 |
| WO | WO 2007/058433 | 5/2007 |
| WO | WO 2007/082480 A1 | 7/2007 |
| WO | WO 2007/125468 A2 | 11/2007 |
| WO | WO 2008/144496 A1 | 11/2008 |
| WO | WO 2009/002152 | 12/2008 |
| WO | WO 2009/002580 A2 | 12/2008 |
| WO | WO 2009/021240 A2 | 2/2009 |
| WO | WO 2009/098485 A1 | 8/2009 |
| WO | PCT/GB2009/002186 | 3/2010 |
| WO | WO 2010/091410 A2 | 8/2010 |

OTHER PUBLICATIONS

2100 Bioanalyzer, Agilent.com, http://www.chemagilent.com/en-US/product/instruments/lab-on-a-chip/2100bioanalyser/Pages/default.aspx. Accessed Feb. 12, 2010, 2 pages.

Chou et al., "A miniaturized cyclic PCR device—modeling and experiments," *Microelectronic Engineering* 61-62 (2002): 921-925.

(56) References Cited

OTHER PUBLICATIONS

Chou et al., "Rapid genotyping with integrated continuous-flow PCR and bioelectronic detection," 7th *International Conference on Miniaturized Chemical and Biochemical Analysis Systems* Oct. 5-9, 2003, Squaw Valley, CA, USA: 1203-1205.

Cotton et al., "Validation of the AMPFISTR® SGM Plus™ system for use in forensic casework," Forensic Science International (2000) 112: 151-161.

Easley et al., "A fully integrated microfluidic genetic analysis system with sample-in-answer-out capability," Proceedings of the National Academy of Sciences of the United States of America USA (2006) 103 (51): 19272-19277.

Green et al., "Developmental validation of the Quantifiler™ real-time PCR kits for the quantification of human nuclear DNA samples," J. Forensic Sci. (2005) 50 (4): 809-825.

Hopwood et al., "Forensic response vehicle: Rapid analysis of evidence at the scene of a crime," *International Congress Series* (2006) 1288: 639-641.

Howitt, T., "Maximising the value of DNA evidence through a service approach," *The Forensic Science Service*, Birmingham, West Midlands, England.

Jeffreys, A.J. "Hypervariable 'minisatellite' regions in human DNA." *Nature*. vol. 314 (6006) 1985. pp. 67-73.

Knox et al., "Improved DNA analysis through real-time PCR analysis," Forensic Magazine (2007): 16-24.

Lagally et al. "Fully integrated PCR capillary electrophoresis microsystem for DNA analysis." *Lab on aChip*, vol. 1. 2001. pp. 102-107.

Lenigk et al., "A fully automated sample-preparation cartridge for geneexpression based diagnostics," 8th *International Conference on Miniaturized Systems for Chemistry and Life Sciences* Sep. 26-30, 2004, Malmö, Sweden: 273-275.

Liu et al. "Integrated portable polymerase chane reaction—capillary electrophoresis microsystem for rapid forensic short tandem repeat typing" Anal Chem. 79(5): 1881-1889 (2007).

Liu et al., "Self-contained, integrated biochip system for sample-to-answer genetic assays," 7th International Conference on Miniaturized Chemical and Biochemical Analysis Systems Oct. 5-9, 2003, Squaw Valley, CA, USA.

Liu et al: "Self-Contained, Fully Integrated Biochip for Sample Preparation, Polymerase Chain Reaction Amplification, and DNA Microarray Detection," Analytical Chemistry, American Chemical Society, US LNKD-DOI: 10.1021/AC0353029, vol. 76, No. 7, Apr. 1, 2004, pp. 1824-1831.

Mathies et al. "Integrated portable microchip system for rapid forensic STR typing." Proceedings of the 17th International Symposium on Human Identification. http://www.promega.com/geneticidproc.ussymp17proc/oralpresntations/Mathies.pdf. Oct. 9-12, 2006.

Richard et al., "Developmental validation of a real-time quantitative PCR assay for automated quantification of human DNA," *J. Forensic Sci.* (2003) 48 (5): 1041-1046.

Sadler et al., "Thermal management of BioMEMS: Temperature control for ceramic-based PCR and DNA detection devices," *IEEE Transactions on Components and Packaging Technologies* (2003) 26(2): 309-316.

Sadler et al., "Thermal Management of BioMEMS," *IEEE Proceedings* (2002): 1025-1032.

Schmalzing et al. "DNA sequencing on microfabricated electrophoretic devices" Anal Chem. 70(11): 2303-2310 (1998).

Schmalzing et al. "Recent developments in DNA sequencing by capillary and microdevice electrophorresis." Electrophoresis 20(15-16):3066-3077 (1999).

Schmalzing et al. "Toward real-world sequencing by microdevice electrophoresis." Genome Res. 9(9):853-858 (1999).

Schmalzing et al. "Two-color multiplexed analysis of eight short tandem repeat loci with an electrophoretic microdevice." Anal Biochem 270(1):148-152 (1999).

Sparkes et al., "The validation of a 7-locus multiplex STR test for use in forensic casework—(II) Artefacts, casework studies and success rates," *Int. J. Legal Med* (1996) 109: 195-204.

Sparkes et al, "The validation of a 7-locus multiplex STR test for use in forensic casework—(II) Mixtures, ageing, degradation and species studies," *Int J. Legal Med* (1996) 109: 186-194.

Zhang et al., "PCR microfluidic devices for DNA amplification," Biotechnology Advances (2006) 24 (3): 243-284.

Form PCT/ISA/210 for corresponding International Application PCT/GB2009/000354.

Form PCT/ISA/237 for corresponding International Application PCT/GB2009/000354.

Form PCT/ISA/220 for corresponding International Application PCT/GB2009/000354.

Form PCT/ISA/206 for corresponding International Application PCT/US2010/023617.

Form PCT/ISA/220 for corresponding International Application PCT/US2010/023617.

Form PCT/ISA/210 for corresponding International Application PCT/US2010/023617.

Form PCT/ISA/237 for corresponding International Application PCT/US2010/023617.

Form PCT/ISA/206 for corresponding International Application PCT/US2010/023631.

Form PCT/ISA/210 for corresponding International Application PCT/US2010/023631.

Form PCT/ISA/220 for corresponding International Application PCT/US2010/023631.

Form PCT/ISA/237 for corresponding International Application PCT/US2010/023631.

Form PCT/ISA/206 for corresponding International Application PCT/US2010/023639.

Form PCT/ISA/210 for corresponding International Application PCT/US2010/023639.

Form PCT/ISA/220 for corresponding International Application PCT/US2010/023639.

Form PCT/ISA/237 for corresponding International Application PCT/US2010/023639.

Form PCT/ISA/206 for corresponding International Application PCT/US2010/023647.

Form PCT/ISA/210 for corresponding International Application PCT/US2010/023647.

Form PCT/ISA/220 for corresponding International Application PCT/US2010/023647.

Form PCT/ISA/237 for corresponding International Application PCT/US2010/023647.

Form PCT/ISA/210 for International Application No. PCT/US2008/072819.

Form PCT/ISA/237 for International Application No. PCT/US2008/072819.

Form PCT/ISA/210 for related International Application No. PCT/US2011/049141.

Form PCT/ISA/237 for related International Application No. PCT/US2011/049141.

U.S. Appl. No. 61/026,869, filed Feb. 2008, Zenhausern et al.

Form PCT/ISA/210 for related International Application No. PCT/GB2011/051591.

Form PCT/ISA/220 for related International Application No. PCT/GB2011/051591.

Form PCT/ISA/237 for related International Application No. PCT/GB2011/051591.

Form PCT/ISA/210 for related International Application No. PCT/GB2011/051508.

Form PCT/ISA/220 for related International Application No. PCT/GB2011/051508.

Form PCT/ISA/237 for related International Application No. PCT/GB2011/051508.

\* cited by examiner

Design Specifications

Design Specification : fSS Buccal

| Functional Chambers | Volume | Depth | Tool | Vent | Note |
|---|---|---|---|---|---|
| C1 (Lysis) | 300ul total | 1mm | | | |
| C2 (Purification/Beads) | 311ul total | 0.75mm | | Yes | |
| Expansion Chamber | 67ul total | 0.75mm | | | |
| C3 (Dwell) | 250ul total | 0.5mm | | Yes | |
| C4 (Heating/Magnet) | 250ul total | 1.0mm | | Yes | |
| Bead Storage Chamber | 30ul total | 1.0mm | | Yes | |
| PCR Chamber | 23ul | 1.0mm | | | |
| Binding Buffer Chamber | 40ul total | 2.0mm | | Yes | |
| Auxiliary Chambers | | | | | |
| Elution | 150ul total | 2.0mm | | Yes | |
| Wash Buffer | 250ul total | 1.0mm | | No | |
| Recovery | 200ul | 2.0mm | | Yes | |
| EC Pump | 1124ul total | 2.0mm | | | |
| Waste | 1000ul total | 2.5mm | | Yes | |
| Channel | | | | | |
| Flow Channel | | 0.5mm | 0.5mm BEM | | |
| Pump Channel | | 0.5mm | 0.5mm BEM | | See A.N. |
| PCR Entrance Channel | | 1.0mm | 1.5mm BEM | | |
| Paraffin Valve | Diameter | | | | |
| Open Valve | 1.0mm | 0.5mm | | | |
| Close Valve | 2.0mm | 1.0mm | | | |
| Close Valve 12/13 | 3.0mm | 1.0mm | | | PCR Close valves enlarged |
| Cartridge Specification | | | | | |
| Height | 160mm | | | | |
| Width | 125mm | | | | |
| Thickness | 3.0mm | | | | |
| Electrode Glue | UV Glue | | | | |
| Alignment Pin | 2.3mm | | | | |
| Bonding Tape | 90106 | | | | |
| Fabrication Note | | | | | |
| Tape trimmed in chambers | | | | | |

FIG. 3b

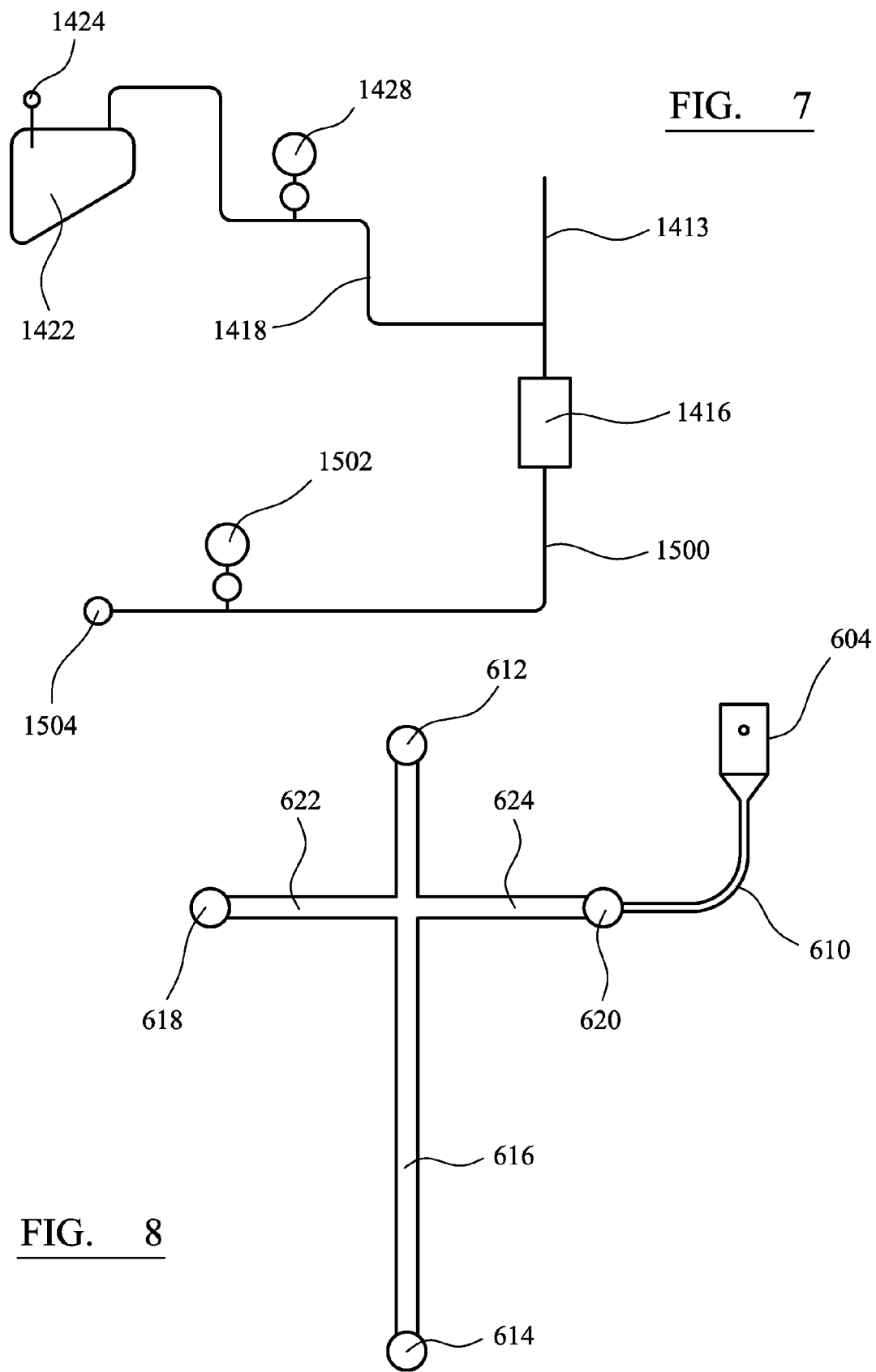

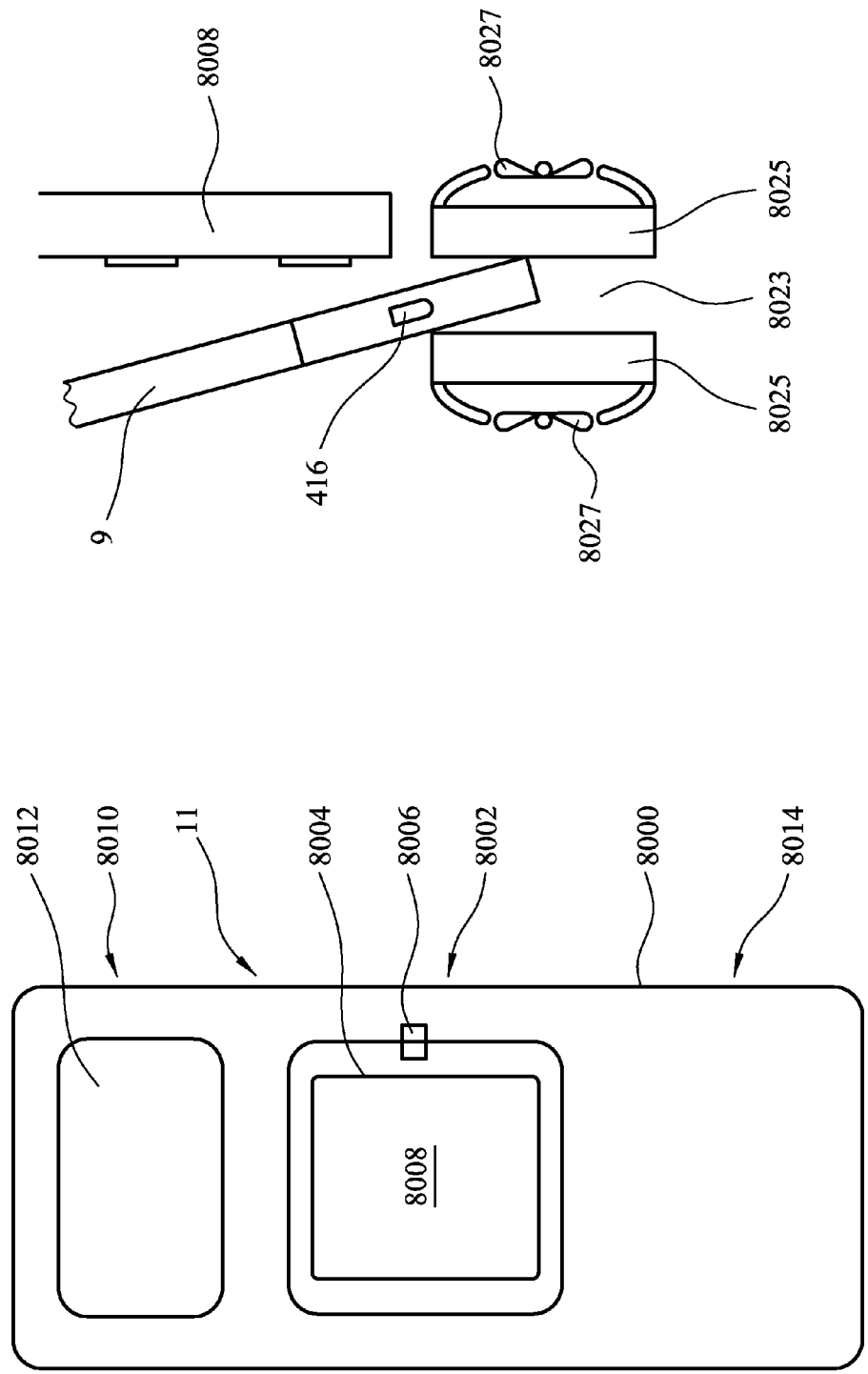

FIG. 28b

| Functional Chambers | Volume | Depth | Tool | Vent | Note |
|---|---|---|---|---|---|
| C1 (Lysis) | 300ul | 1mm | Std Cutter | No | |
| C2 (Purification) | 311ul | 0.75mm | Std Cutter | Yes | |
| Expansion/Mixing Chambers | 67ul | 0.75mm | Std Cutter | No | |
| C3 (Dwell or Initial Binding)) | 250ul | 0.5mm | Std Cutter | Yes | |
| C4 (PCR washing and release) | 250ul | 1.0mm | Std Cutter | Yes | |
| Bead Storage (BSC) | 30ul | 1.0mm | Std Cutter | No | |
| Binding Buffer (BBC) | 40ul | 2.0mm | Std Cutter | No | |
| Elution | 150ul | 2.0mm | Std Cutter | No | |
| Wash Buffer | 250ul | 2.0mm | Std Cutter | No | |
| Archive | 200ul | 2.0mm | Std Cutter | No | |
| Waste | 1000ul | 2.5mm | Std Cutter | Yes | |
| PCR | 10ul | 1.0mm | Std Cutter | No | |
| Formamide | 105ul | 1.0mm | Std Cutter | No | |
| Denaturing | 105ul | 1.0mm | Std Cutter | No | |
| Channel | | | | | |
| PCR Red | | 0.25mm | 0.5mm BEM | | Sigma-Aldrich 411663 |
| PCR Cyan | | 1.0mm | 1.0mm BEM | | Sigma-Aldrich 411663 |
| PCR White/Black | | 0.35mm | 0.5mm BEM | | Sasolwax H1 |
| Magenta | | 0.5mm | 1.0mm BEM | | |
| EC PUMP Yellow | | 2.0mm | 1.0mm BEM | | |
| Paraffin Valve | Volume | Depth | Tool | | |
| LMW OV's 1.5mm diameter | 1.77ul | 0.5mm | Std Cutter | | |
| LMW OV's 3.0mm diameter | 7.1ul | 1.0mm | Std Cutter | | |
| HMWV CV15 | 7.1ul | 1.0mm | Std Cutter | | |
| Cartridge Specification | | | | | |
| Substrate width - 175mm | | | | | |
| Substrate length - 228mm | | | | | |
| Substrate 3.0mm PC | | | | | |
| | | | | | |
| Capping Layer 0.5mm PC | | | | | |
| PSA 90106 cold bond assy | | | | | Adhesives Research |
| EC pump UV glue 1180-M | | | | | |
| | | | | | |
| Bar Code pocket | N/A | 0.2mm | Std Cutter | | May opt for flduclai:marks instead |

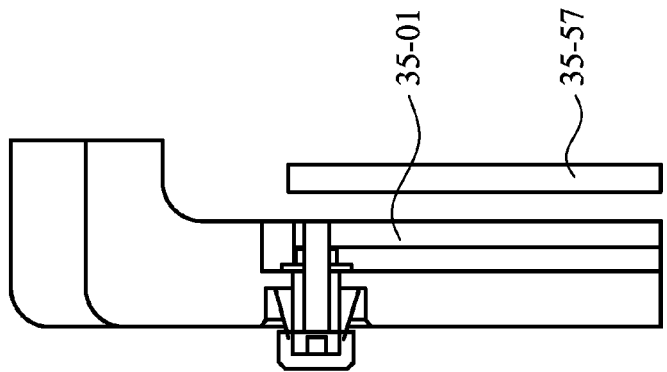
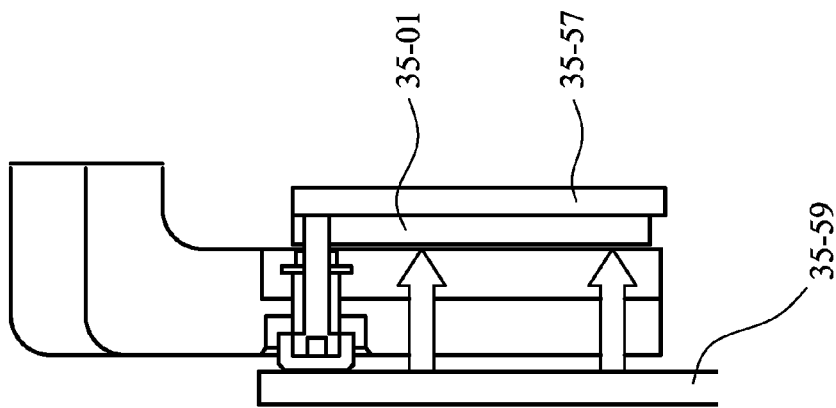
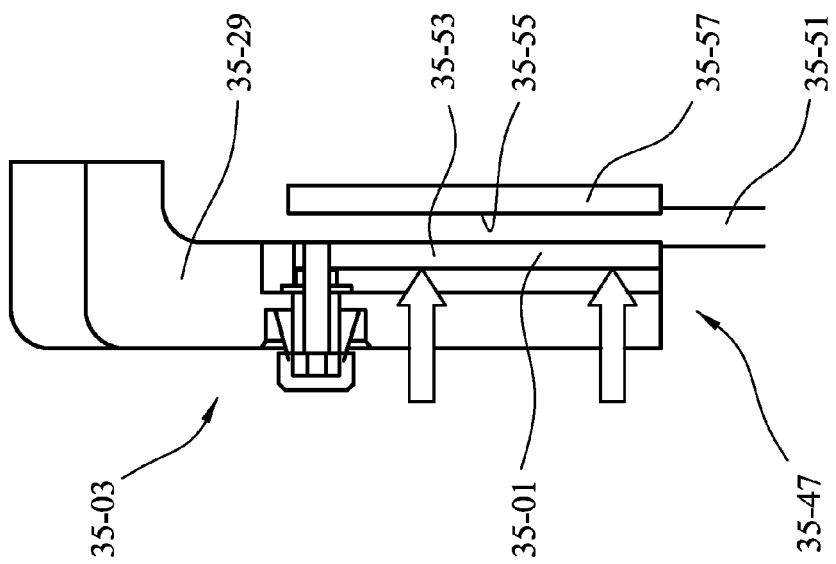
FIG. 35c
FIG. 35b
FIG. 35a

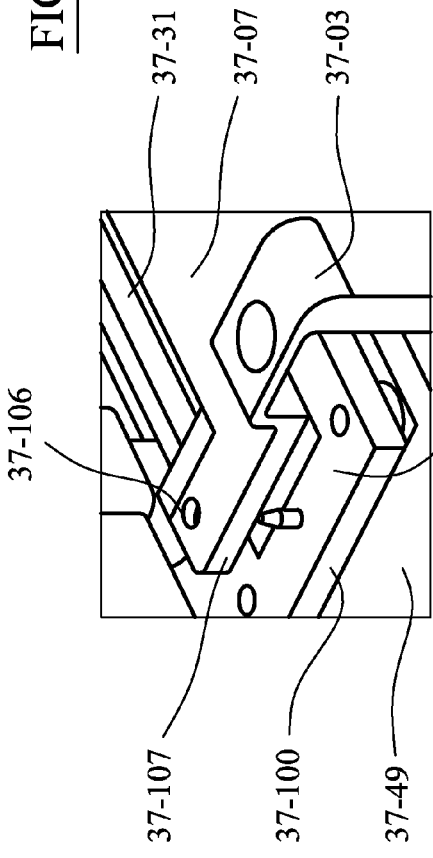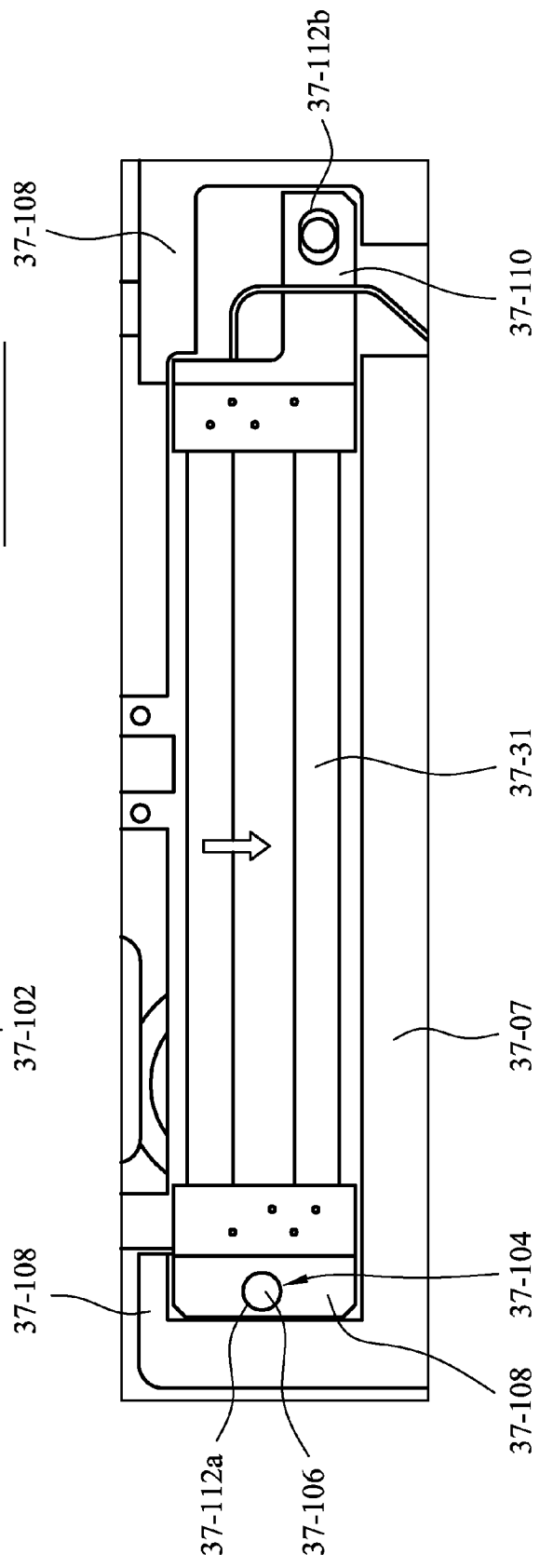

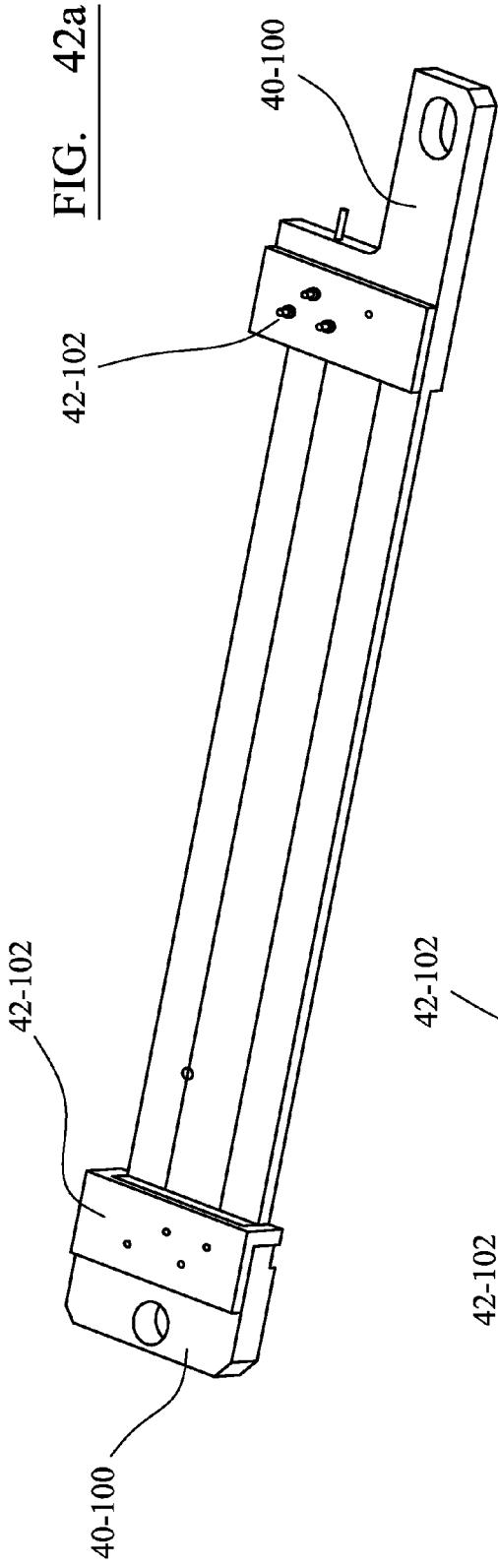

PERFORMANCE

CROSS-REFERENCE TO RELATED APPLICATIONS

This application is a Utility Application which claims benefit of Ser. No. 61/151,107, filed Feb. 9, 2009 in the United States, and of Ser. No. 61/151,104, filed Feb. 9, 2009 in the United States, and of Ser. No. 61/151,111, filed Feb. 9, 2009 in the United States, and of Ser. No. 61/151,117, filed Feb. 9, 2009 in the United States, and which application(s) are incorporated herein by reference. A claim of priority to all, to the extent appropriate is made.

BACKGROUND OF THE INVENTION

The invention concerns improvements in and relating to analysis, particularly, but not exclusively, in relation to biological samples.

SUMMARY OF THE INVENTION

According to a first aspect of the invention, there is provided an instrument for analysing a sample, the instrument including:
one or more sample processors;
electronics for operating the sample processors.

According to a second aspect of the invention, there is provided a device, for processing a sample, the device including:
one or more sample processors.

According to a third aspect of the invention, there is provided a method of producing a device, the method including:
forming one or more sample processors;
providing electronics for operating the sample processors.

According to a fourth aspect of the invention, there is provided a method of analysing a sample, the method including:
applying one or more process steps to the sample;
obtaining one or more results from the method.

The instrument may provide an integrated set of process steps and/or sample processors. The process steps and/or sample processors may include a sample receiving step and/or sample preparation step and/or sample extraction step and/or sample retention step and/or purification step and/or washing step and/or elution step and/or amplification step and/or PCR step and/or denaturing step and/or investigation step and/or detection step and/or electrophoresis step and/or analysis step and/or results output step.

The instrument may provide for a first and a second amplification and/or PCR step. The first amplification and/or PCR step may include a lower number of amplification cycles and/or have a shorter duration than the second. The first amplification and/or PCR step may provide a first amplification product. The first amplification product may be analysed in the chamber where it is amplified and/or before the second amplification product is analysed. The instrument may include a light source and/or optics and/or detector for analysis of the first amplification product. The instrument may include a light source and/or optics and/or detector which are separate from a light source and/or optics and/or detector which are used to analyse the second amplification product. One or more components may be shared.

One or more negative and/or positive controls may be analysed by the instrument, potentially in parallel to a sample. The same or a different cartridge may be used for the control(s).

The instrument may provide an integrated set of process steps and/or sample processors which progresses from start to finish without user intervention. The start may be the loading of the sample into the instrument, for instance loading the sample into the cartridge and/or loading the cartridge into the instrument. The finish may be the amplification step and/or PCR step and/or denaturing step and/or investigation step and/or electrophoresis step and/or analysis step and/or results output step.

One or more of the steps, and preferably each step, includes one or more operations checks. The operation check may determine whether or not the step occurred correctly, for instance in terms of duration and/or temperature and/or pressure and/or activation. One or more of the steps, and preferably each step, includes a position check. The position check may confirm the orientation and/or alignment and/or horizontal alignment and/or vertical alignment and/or lateral alignment of one component relative to another component.

The instrument may provide one or more of the process steps and/or sample processors on a device, such as a cartridge.

The instrument may receive and/or process one or more devices, such as cartridges. The cartridges may be of the same type. One or more of the cartridges may be of a different type to one or more of the other cartridges. Two or more devices, such as cartridges, may be processed by the instrument simultaneously. Two or more devices, such as cartridges, may be being processed at the same time. At that same time, the devices, such as cartridges, may be at the same or different parts of their processing.

The device may be a single sample only device. The device may be a multi-sample device. The device may provide duplicate channel and/or chamber structures and/or arrangements to process the multiple samples. The device may be a single use only device. The device may be discarded or stored after the single use. The whole and/or a part of the device may be discarded and/or stored after use, such as a single use.

The process steps and/or sample processors of a sample receiving step and/or sample preparation step and/or sample extraction step and/or sample retention step and/or purification step and/or washing step and/or elution step and/or amplification step and/or PCR step and/or denaturing step and/or investigation step and/or electrophoresis step and/or analysis step may be performed on or in the device.

The process steps and/or sample processors of an analysis step and/or a results output step may be performed on or in the instrument outside of the device.

The analysis step may be partly performed on or in the device and partly performed on or in the instrument aside from the device.

The instrument may provide a set of process steps and/or sample processors which take a time period of less than 300 minutes from start to finish. Preferably the time period is less than 240 minutes, more preferably less than 180 minutes and more preferably less than 150 minutes. The instrument may provide a set of process steps and/or sample processors which take a time period of greater than 30 minutes, preferably greater than 45 minutes and more preferably greater than 60 minutes. The start may be the loading of the sample into the instrument, for instance loading the sample into the cartridge and/or loading the cartridge into the instrument. The finish may be the completion of the investigation step and/or electrophoresis step and/or analysis step and/or results output step.

The instrument may provide a time period of less than 6 minutes from start to finish for the sample receiving step. Preferably the time period is less than 4 minutes, more preferably less than 3 minutes and more preferably less than 2 minutes. The instrument may provide a set of process steps and/or sample processors from start to finish for the sample receiving step which take a time period of greater than 10 seconds, preferably greater than 20 seconds and more preferably greater than 30 seconds.

The instrument may provide a time period from start to finish for the sample preparation step. The sample preparation step may include one or more of an extraction step and/or a sample retention step and/or a purification step and/or a washing step and/or a elution step. The time period may be less than 40 minutes from start to finish, preferably a time period of less than 30 minutes, more preferably less than 25 minutes and still more preferably less than 20 minutes. The time period may be greater than 10 minutes, preferably greater than 15 minutes and more preferably greater than 18 minutes. The start may be defined by the sample leaving the chamber or location into which the sample is loaded. The finish may be the completion of the loading of the sample into an amplification step.

The instrument may provide a time period from start to finish for the amplification step. The amplification step may include a PCR step. The time period may be less than 150 minutes from start to finish, preferably a time period of less than 120 minutes, more preferably less than 90 minutes and still more preferably less than 70 minutes, potentially less than 50 minutes, potentially less than 40 minutes or potentially less than 30 minutes. The time period may be greater than 30 minutes, preferably greater than 40 minutes and more preferably greater than 50 minutes. The start may be defined by the sample entering the chamber or location at which amplification is provided. The finish may be defined by the sample leaving the chamber or location at which amplification has been provided.

The instrument may provide a time period from start to finish for the investigation step and/or electrophoresis step. The investigation step and/or electrophoresis step may include a denaturing step and/or an analysis step. The time period may be less than 45 minutes from start to finish, preferably a time period of less than 30 minutes, more preferably less than 20 minutes and still more preferably less than 18 minutes. The time period may be greater than 8 minutes, preferably greater than 10 minutes and more preferably greater than 12 minutes. The start may be defined by the sample entering the chamber or location at which denaturation is provided. The start may be defined by the sample entering the channel in which electrophoresis is provided. The start may be defined by the sample entering the channel in which the investigation step is provided. The finish may be defined by the receipt of the last signal from investigation step and/or the electrophoresis step and/or from the channel by the light detector. The finish may be defined by the electrophoresis voltage being turned off.

The instrument may include a housing. The housing may have a volume of less than 300,000 $cm^3$, potentially less than 250,000 $cm^3$, preferably less than 200,000 $cm^3$, possibly less than 175,000 $cm^3$, preferably less than 125,000 $cm^3$, more preferably less than 75,000 $cm^3$ and ideally less than 50,000 $cm^3$.

The instrument may have a maximum height of 100 cm, preferably 76 cm and more preferably 65 cm and possibly 50 cm.

The instrument may have a maximum depth of 75 cm, preferably 65 cm and more preferably 55 cm and still more preferably 45 cm.

The instrument may have a maximum width of 50 cm, preferably 45 cm, possibly 40 cm and even possibly 30 cm.

The instrument may occupy an area on the surface on which the instrument stands, the maximum area occupied may be less than 2500 $cm^2$, preferably less than 2000 $cm^2$, more preferably less than 1750 $cm^2$, possibly less than 1500 $cm^2$ and even possibly less than 1000 $cm^2$.

The instrument may weigh less than 20 kg. The instrument may weigh less than 10 kg.

The instrument may be portable. The casing of the instrument may be provided with one or more carrying handles.

The instrument may require only a single connection to a power supply of 110 to 240V and/or 50 Hz. The instrument may require a two or three pin electrical plug for the power supply. The instrument may be provided with a portable power supply, such as a battery based power supply. The portable power supply may be the only power supply for the instrument. The portable power supply may be a backup power supply for the instrument.

The sample may be received from one or more of: a swab, a buccal swab, a cotton swab, a soft swab, a solution, a suspension, an item of clothing, an item placed in the mouth, a cigarette or piece thereof, chewing gum, one or more hairs, a bone sample, a tissue sample or saliva. The sample may be received in solution and/or suspended in a liquid.

The sample receiving step may include the transfer of a sample from outside the device and/or instrument, to inside the device and/or instrument. The sample receiving step may receive the sample from a collection device or from a storage device. The sample receiving step may include the transfer of the sample to a channel or chamber within the device.

The sample preparation step may include contacting the sample with one or more reagents and/or one or more other components. The reagents and/or other component may be used to prepare the sample for one or more of the subsequent steps.

The sample extraction step may be part of or separate from the sample preparation step. The sample extraction step may include contacting the sample with one or more reagents and/or components which select the sample component(s) relative to one or more waste components in the sample. The selected sample component(s) may be removed from the waste component(s) and/or the waste component(s) may be removed from the selected sample components. The waste component(s) may flow away from the extraction step. The waste component(s) may be washed away from the extraction step using one or more further reagents and/or components.

The sample retention step may be a part of or may be separate from the sample preparation step and/or sample extraction step. The sample retention step may include contacting the sample with one or more reagents and/or components which retain the sample component(s) relative to one or more waste components in the sample. The sample component(s) may be retained on one or more beads. The beads may be magnetic. The retained sample component(s) may be removed from the waste component(s) and/or the waste component(s) may be removed from the retained sample components. The waste component(s) may flow away from the retention step. The waste component(s) may be washed away from the retention step using one or more further reagents and/or components. The waste component(s) may flow past the location of retention. The waste component(s) may be washed away using one or more further reagents and/or components which flow past the location of retention.

The retained and/or selected sample may be eluted, preferably with the eluent conveying the retained and/or selected sample to the next step.

The purification step may be a part of or may be separate from the sample preparation step and/or sample extraction step and/or sample retention step. The purification step may separate the selected sample components, for instance DNA, from one or more waste components of the sample, for instance cellular material, PCR inhibitors and chemical inhibitors.

The washing step may be a part of or may be separate from the sample preparation step and/or sample extraction step and/or sample retention step and/or purification step. The washing step may remove one or more components of the sample from the location of one or more other components of the sample.

The elution step may be a part of or may be separate from the sample preparation step and/or sample extraction step and/or sample retention step and/or purification step and/or washing step. The elution step may remove one or more components of the sample from a first form into a second form. The first form may be bound to a surface or substrate, for instance on a bead. The second form may be in a liquid, for instance the eluent.

The amplification step may include contacting the sample with one or more reagents and/or components to cause amplification. The amplification step may include contacting the sample with conditions, preferably of a cyclic nature, to cause amplification. The amplification may be provided by a PCR step.

The denaturing step may prepare the sample for electrophoresis. The denaturing step may include contacting the sample with one or more reagents and/or components. The denaturing step may include contacting the sample with conditions, preferably of a cyclic nature, to cause denaturing.

The investigation step may provide a characteristic for one component of the sample which differs from the characteristic for one or more other components of the sample. The characteristic may be one or more detectable positions and/or one or more signals and/or one or more intensities and/or one or more colours and/or one or more concentrations and/or presence of one or more characteristics and/or absence of one or more characteristics.

The electrophoresis step may be part of or may be separate from the investigation step. The electrophoresis step may include transferring the sample to a start location for electrophoresis and/or a mobility based separation and/or a size based separation. The start location may be in a channel. The electrophoresis step may include one or more voltage conditions. One or more voltage conditions may be used to transfer the sample to the start location. One or more voltage conditions may be used to provide the separation.

The analysis step may establish one or more of the characteristics of the sample. The analysis may interrogate the instrument, particularly the device, and/or may seek a response from the instrument, particularly the device. The analysis may subject the instrument, particularly the device, to an operation, for instance the application of light. The analysis may consider the response to the operation, for instance the light returning.

The analysis step may include one or more operations involving an interaction with the device. The analysis step may include one or more operations not involving an interaction with the device. One or more of the interactions may be electromagnetic interactions.

The analysis step may apply light to the device. The analysis step may receive light from the device. The analysis step may establish the relative position of the elements having a characteristic, for instance an allele having a fluorescent dye. The analysis step may establish the relative size of the elements having a characteristic, for instance an allele having a fluorescent dye. The analysis step may generate one or more results. The light may be of visible and/or non-visible wavelengths. The results output step may display the one or more results from the analysis step and/or a processed form thereof.

The results output step may transmit the one or more results from the analysis step and/or a processed form thereof to a remote location. The results output step may compile the one or more results into a transmission form. The transmission may be via a telecommunications network. The results may be provided in a format compatible with one or more software applications.

The results output step may be followed by a further processing step. The further processing may interpret the results to provide further results. The further processing step may analyse the results to provide a DNA profile for the sample. The further processing step may provide an indication of a match between the sample and a database record of a sample. The further processing step may be provided at a location remote from the instrument. The further processing step may be provided at a location connected to the instrument, at least part of the time, by a telecommunications network. The further processing step may return to the instrument and/or a computer, preferably within 200 m of the site of the instrument, the further processed results.

The results may be processed on the instrument to give processed results. The processed results may extract from the results the signals, sections of signals or positions attributable to a characteristic being analysed for, such as an allele. The results and/or processed results may be provided to the results output step.

The instrument may include a housing, such as a casing. A single housing may be provided for the instrument. The housing may enclose one or more, preferably all of: a cartridge location; cartridge to instrument interface; operating electronics for the cartridge; operating electronics for the cartridge to instrument interface; data processor; powers supply; light source; optical system; light detector; computer software; computer hardware; telecommunications unit.

The casing may include one or more removable panels and/or portions, for instance to allow access to components provided within the casing.

The housing may be provided with a door.

The door may be provided with a restraint, such as a latch, to hold the door in the closed position. The door may be held closed by gravity.

The instrument may have an orientation of use, the door may be provided in the upper half of the instrument, preferably the upper third of the instrument, potentially between 50% and 80% of the way up the instrument. The door may be provided in the upper 20% of the height of the instrument. The door may form part of the upper surface of the casing and/or the front surface of the casing. The hinge for the door may be provided on the upper surface of the casing.

The door may be provided with one or more contact switches. The one or more contact switches may be used to control one or more processes and/or steps and/or actions within the device, for instance the availability of a voltage to certain components within the instrument and/or the availability of light from certain components. The one or more contact switches, when open, may isolate and/or prevent operation of one or more components within the instrument, for instance the power supply or one or more parts of the power supply and/or the laser or other light source.

The cartridge location is preferably provided inside the instrument, preferably behind the door. This may be behind the door by being below it vertically and/or behind the door by being behind it horizontally. The cartridge to instrument interface is preferably provided inside the instrument, preferably behind the door.

The door may have an open position which allows access to a work surface within the instrument. The work surface may include the access route, such as a slot, to the cartridge location.

The cartridge location may be a planar location. The cartridge location may extend parallel to the door, for instance parallel +/−10°, more preferably +/−5°.

With a cartridge in the instrument, in the cartridge location, the cartridge may extend parallel to the door, for instance parallel +/−10°, more preferably +/−5°.

The cartridge to instrument interface may be include a planar surface. The cartridge to instrument interface may include a planar surface which extends parallel to the door, for instance parallel +/−10°, more preferably +/−5°. Preferably the planar surface faces the cartridge location.

The cartridge to instrument interface may include one or more components, preferably exposed at the planar surface. The one or more components may include one or more heaters. The one or more components may include one or more coolers. The one or more components may include one or more Peltier effect components. The one or more components may include an actuator. The one or more components may include one or more sensors, for instance temperature sensors. The or one or more magnets may be moved through an aperture in the cartridge to instrument interface. The one or more magnets may include one or more permanent magnets and/or include one or more electro-magnets.

One or more of the heaters may be printed onto the cartridge to instrument interface. One or more of the heaters may have a square face. The cartridge to instrument interface may have an orientation of use, one or more edges of a heater being inclined relative to the horizontal, preferably by 45°+/−5°.

Preferably the actuator provides reciprocating motion. Preferably the actuator is connected to a mounting for a magnet. The magnet may be a permanent and/or electro magnet. The actuator may have a first state. The actuator may have a second state, the magnet being closer to the cartridge location in the second state than in the first state. The magnet may move along an axis perpendicular to the plane of the cartridge location and/or planar surface of the cartridge to instrument interface, +/−10°, more preferably +/−5°.

One or more of the components may have a planar face. Preferably the planar face of a component faces the cartridge location. Preferably the planar face of a component is parallel to the cartridge location and/or to the cartridge to instrument interface, particularly the planar surface thereof. The planar face of a component may be coplanar with the cartridge location. The planar face of a component may be coplanar with the cartridge to instrument interface, particularly the planar surface thereof. The planar face of a component may be raised compared with the adjoining part of the cartridge to instrument interface, potentially the whole of the planar face of the cartridge to instrument interface.

The cartridge to instrument interface may be a printed circuit board.

The cartridge to instrument interface may be connected to the operating electronics on the rear surface thereof.

The operating electronics for the cartridge may include one or more power supplies. Preferably a power supply is connected to the electrical connections for a pump provided in the cartridge, preferably for each pump. The operating electronics for the cartridge may include a controller or controllers allowing separate operation of each pump in the cartridge.

The connection between the pump and the operating electronics for the cartridge may be provided by abutting contacts. The contacts may abut when the cartridge is introduced to the cartridge location and/or when the door of the instrument is closed. The elements of the operating electronics for the cartridge which contact the cartridge and/or elements mounted thereon are preferably mounted on or in the cartridge to instrument interface.

The connection between the pump(s) and the operating electronics for the cartridge may be provided by one or more pins mounted on the cartridge. The one or more pins may be spring loaded. The one or more pins may be partially or fully recessed into a surface of the cartridge, particularly the planar face thereof. The connection may be provided or may be further provided by one or more pins mounted on the cartridge to instrument interface. The one or more pins may be spring loaded. The one or more pins may be partially or fully recessed into a surface of the cartridge to instrument interface, particularly the planar face thereof which opposes the cartridge. The connection may be made when the cartridge is put in the use position.

The connection between the pump(s) and the operating electronics for the cartridge may be provided in a recessed portion of the cartridge. The recessed portion may be provided by a recess in the perimeter of the cartridge, particularly a recess extending in the main plane of the cartridge.

The operating electronics for the cartridge to instrument interface may be, at least in part, mounted on or in the cartridge to instrument interface. The operating electronics for the cartridge to instrument interface may include one or more power supply controllers and/or one or more heater controllers and/or one or more temperature controllers and/or one or more actuator controllers and/or sensor monitors and/or voltage controllers.

The power supply may include a power supply for the pumps provided in the cartridge. The power supply may include a power supply for one or more heaters provided in or on the cartridge to instrument interface. The power supply may include a power supply for one or more coolers provided on or in the cartridge to instrument interface. The power supply may include a power supply for the actuator for a magnet. The power supply may include a power supply for one or more fans, particularly fans for a Peltier heater. The power supply may include a power supply for an electrophoresis step. The power supply may include a power supply for a light source. The power supply may include a power supply for a light detector. The power supply may include a power supply for an optics alignment and/or verification and/or calibration components.

The light source and/or optical system and/or light detector and/or power supply for one or more of these components may be provided in the lower half, preferably lower third of the instrument.

The light source may be a laser. The laser may emit at a wavelength between 480 nm and 520 nm, preferably between 488 nm and 508 nm. The laser may have a power of at least 15 mW, potentially 20 mW, preferably 25 mW, more preferably 35 mW and ideally at least 45 mW.

The light source may be one or more light emitting diodes.

The optical system may receive light from the light source and/or deliver light to a channel and/or receive light from a channel and/or deliver light to a light detector.

The light detector may be a charge coupled device. The light detector may be provided with one or more lenses.

The computer software may be computer software for implementing the interface with the user. The computer software may be computer software for implementing the operation of one or more of the heaters and/or one or more coolers and/or one or more sensors and/or actuator and/or one or more pumps and/or one or more reactions in the cartridge and/or one or more processes in the cartridge.

The data processor may be a computer. The computer hardware may operate the computer software.

The telecommunications unit may be connected to the data processor and/or computer hardware. The telecommunications unit may be configured to connect to a mobile telecommunications network, such as a mobile phone telecommunications network, satellite phone telecommunications network. The telecommunications unit may be configured to connect to the Internet. The telecommunications device may be configured to provide data from the instrument to a remote location, preferably electronically.

A display unit may be provided in the housing. The instrument may have an orientation of use, the display unit may be provided in upper half of the instrument, preferably the upper quarter of the instrument, potentially between 60% and 95% of the way up the instrument. The display unit may be provided in the lower 50% of the instrument.

The display unit may include a touch sensitive screen. The user may input commands to the instrument through the display. The display may include or be a touch sensitive screen. A stylus and/or stylus storage location may be provided near the display. The stylus may be used to input commands. The user may input commands to the instrument through one or more buttons and/or switches.

The display unit and/or a further display unit may provide a visual indication of the progress of the method relative to the total method. The visual indication may relate to the whole of the method being performed by the instrument and/or one or more of the steps in the whole method. An elongated bar which progressively lights up with progress may be used.

The first and/or second and/or third and/or fourth aspects of the invention may include any of the features, options or possibilities set out elsewhere in this application, including in the other aspects of the invention, the specific description of the embodiments and the drawings.

According to a fifth aspect of the invention, there is provided an instrument for analysing a sample, the instrument including:

one or more sample processors;
electronics for operating the sample processors.

One or more of the sample processors may be provided on a device. The device may be inserted into the instrument. The device may be a cartridge. One or more of the sample processors may be provided on the instrument.

The device is preferably inserted into a device location. The device location is preferably provided inside the instrument, preferably behind a door.

The device to instrument interface is preferably provided inside the instrument, preferably behind the door. The device to instrument interface is preferably provided by the device abutting a component of the instrument, with the device in the device location. A compressive force may be applied to the device and/or to the component of the instrument, for instance to improve contact.

The device may provide all of the drivers for the process steps and/or processors. The device may provide all the elements which move fluids within the process steps and/or processors. The device may provide all the pumps for the process steps and/or processors. The device may provide all of the materials which form the valves and/or seals in the device. The device may provide all the moveable components for the process steps and/or processors, aside from the actuator for the magnet. The device may provide all the reagents for the process steps and/or processors.

The device may have no electrical power sources therein. The device may have no variable magnetic field source therein. The device may have no fluid expansion drivers therein. The device may have no heaters therein. The device may have no coolers therein. The device may have no sensors therein. The device may have no energy sources therein. No material or elements may enter the device from the interface element.

The instrument, particularly the interface element, may provide all of the electrical power sources for the device. The instrument, particularly the interface element, may provide all of the variable magnetic field sources for the device. The instrument, particularly the interface element, may provide all of the fluid expansion drivers, such as heaters, for the device. The instrument, particularly the interface element, may provide all the heaters for the device. The instrument, particularly the interface element, may provide all of the coolers for the device. The instrument, particularly the interface element, may provide all of the energy sources for the device.

The instrument, particularly the interface element, may have no direct contact with the contents of the device. The instrument, particularly the interface element, may provide none of the drivers for the process steps and/or processors. The instrument, particularly the interface element, may provide none of the elements which move fluids within the process steps and/or processors. The instrument, particularly the interface element, may provide none of the pumps for the process steps and/or processors. The instrument, particularly the interface element, may provide none of the materials which form the valves and/or seals in the device. The instrument, particularly the interface element, may provide none of the moveable components for the process steps and/or processors, aside from the actuator for the magnet. The instrument, particularly the interface element, may provide none of the reagents for the process steps and/or processors.

The interaction between the device and the interface element may be limited to radiation of heat into the device and/or conduction of heat into the device and/or one or more electrical contacts and/or a magnetic field passing into or through the device. No substance may enter the device from the instrument, particularly the interface element.

The device location may be a planar location. The device location may extend parallel to the door, for instance parallel +/−10°, more preferably +/−5°.

With a device in the instrument, in the device location, the device may extend parallel to the door, for instance parallel +/−10°, more preferably +/−5°.

The device may be inserted into the instrument by one or more steps.

The insertion may include the step of inserting a section of the device into a slot in the instrument. The slot may be provided in the bottom section of the device location, for instance the lower 25%, preferably lower 15%. The slot may be provided by a component of the instrument and particularly a component of the interface element. The device may be inclined relative to the plane of the slot and/or device location and/or interface element during the insertion.

The section of the device may be the section of the device which includes the amplification step and/or PCR step and/or a chamber for providing amplification and/or PCR.

The slot may be provided between a first element and a second element. The first element and/or second element may include a heater and/or a cooler and/or a fan. The first element and/or second element may include a Peltier device, preferably a Peltier heater. The first element may have two or more positions, particularly with one of the positions providing a larger separation in the slot between the first element and the second element, than one or more of the other positions. The second element may have two or more positions, particularly with one of the positions providing a larger separation in the slot between the first element and the second element, than one or more of the other positions. The first and/or second element may be biassed towards a position with a separation in the slot which is less than in one or more of the positions. The positions may vary by the first and/or second elements moving perpendicular to the plane of the device location and/or device. The first and/or second element may be biassed towards a position in which the one or both of the opposing faces of the first and second elements abut the device.

A first heater, such as a Peltier device, may be positioned against a second heater, such as a Peltier device. The first and second heaters may be stacked on one another. The first and second heaters may be provided abutting one another, and preferably with one of the first and second heaters abutting the cartridge in use.

One or more or all of the heaters provided in the instrument may be Peltier devices. One or more or all of the heaters provided in the instrument may be infra-red heaters. One or more or all of the heaters provided in the instrument may be resistance heaters. One or more or all of the heaters provided in the instrument may be microwave heaters.

The insertion may include a step in which the device is rotated about an area or axis, particularly after the section of the device has been inserted into the slot. The rotation may cause one or more elements on the device to cooperate with one or more elements on the instrument, particularly the interface element. One or more elements on the device, such as a cartridge, may cooperate with one or more elements on the interface element. The elements may be a male element, such as a dowel, on one of the device or instrument, preferably with a female element, such as a recess, on the other. Some or all of the male elements may be provided on the device. Some or all of the female elements may be provided on the device. Some or all of the male elements may be provided on the instrument. Some or all of the female elements may be provided on the instrument.

The arrangement of the elements may be such that the device can be positioned in the device location given one orientation of the device. The arrangement of the elements may be such that the device can be positioned in the device location given one orientation of the device. The arrangement of the elements may be such that the device cannot be positioned in the device location given one or more orientations of the device.

The cartridge to instrument interface may include a planar surface. The cartridge to instrument interface may include a planar surface which extends parallel to the door, for instance parallel +/−10°, more preferably +/−5°. Preferably the planar surface faces the cartridge location.

The compressive force may be applied to the device and/or to the component of the instrument by the door of the instrument. The door may be provided with one or more elements which abut the device. The one or more elements may be spring loaded.

The compressive load may be applied by one or more structures, such as a clip or a clamp, which have a first position with a first separation and a second position with a second separation, the second separation being smaller than the first separation, a part of the device and/or of the instrument being provided between the separation. Preferably the second position provides a compressive force to the device and/or instrument.

The device to instrument interface may include one or more components, preferably exposed at the planar surface. The one or more components may include one or more heaters. The one or more components may include one or more coolers. The one or more components may include an actuator. The one or more components may include one or more sensors, for instance temperature sensors. The magnet may be moved through an aperture in the device to instrument interface.

One or more of the heaters may be printed onto the device to instrument interface. One or more of the heaters may have a square face. The device to instrument interface may have an orientation of use, one or more edges of a heater being inclined relative to the horizontal, preferably by 45°+/−5°.

Preferably the actuator provides reciprocating motion. Preferably the actuator is connected to a mounting for a magnet. The magnet may be a permanent and/or electro magnet. The actuator may have a first state. The actuator may have a second state, the magnet being closer to the device location in the second state than in the first state. The magnet may move along an axis perpendicular to the plane of the device location and/or planar surface of the device to instrument interface, +/−10°, more preferably +/−5°.

One or more of the components may have a planar face. Preferably the planar face of a component faces the device location. Preferably the planar face of a component is parallel to the device location and/or to the device to instrument interface, particularly the planar surface thereof. The planar face of a component may be coplanar with the device location. The planar face of a component may be coplanar with the device to instrument interface, particularly the planar surface thereof. The planar face of a component may be raised compared with the adjoining part of the device to instrument interface, potentially the whole of the planar face of the device to instrument interface.

One or more of the components may be fixed relative to the interface element and/or device to instrument interface. One or more of the components may have a degree of movement relative to the interface element and/or device to instrument interface, for instance by spring loading the component. The degree of movement may be perpendicular to the plane of the device location and/or interface element. The degree of movement may be parallel to the plane of the device location and/or interface element. The one or more components may be biased towards the device location and/or away from the interface element.

One or more materials may be provided at the device to instrument interface. The material may be thermally conductive. The material may be uniform. The material may be uniform in the direction between the device and the interface element. The material may vary between locations in the plane of the device to instrument interface. One or more of the materials may be a solid, a paste or a liquid. One or more of the materials may include particles or nanoparticles. One or more of the materials may be provided on the device. One or more of the materials may be provided on the instrument. A compressible material may be provided at the device to instrument interface. A layer, for instance a protective layer, may be provided over the one or more materials. The layer may be a peelable layer. Preferably the layer is removed before the device is inserted into the instrument.

The device to instrument interface may be a printed circuit board.

The device to instrument interface may be connected to the operating electronics on the rear surface thereof.

The operating electronics for the device may include one or more power supplies. Preferably a power supply is connected to the electrical connections for a pump provided in the device, preferably for each pump. The operating electronics for the device may include a controller or controllers allowing separate operation of each pump in the device.

The door may have an open position which allows access to a work surface within the instrument. The work surface may include the access route, such as a slot, to the device location. The device location may be a cartridge location. The device location may be a planar location.

The device location may be opposed by a device to instrument interface, for instance a cartridge to instrument interface, which may itself include a planar surface. The device to instrument interface may include one or more components, preferably exposed at the planar surface.

The device may have an insertion position in which it opposes, but is not in contact with the device to instrument interface. The device may have a use position in which it opposes and is in contact with the device to instrument interface.

The device may be mounted on a carrier.

The device may be mounted on the carrier with the carrier outside of the instrument. The device may be mounted on the carrier before use. The device may be removed from the carrier with the carrier outside of the instrument. The device may be removed from the carrier after use.

The device may provide a first support. The first support may be rectilinear in profile. The first support may receive the device. The planar device may be presented to the planar first support.

The device may be connected to the first support by one or more releasable fasteners, such as screw threaded fasteners. The fasteners may interact with a plurality of engagement locations provided on the device, for instance in the corner portions thereof. The releasable fasteners may be retained on the first support. Initial contact may provide for the releasable fasteners engaging with the device. Tightening of the releasable fasteners may draw the device into contact with the support. The contact may be between one or more peripheral portions of the device of the periphery thereof and the first support. The releasable fasteners may hold the device against the first support, but still allow movement of the device away from the first support in response to a force above a certain level. A force, for instance above that level may be applied to move the device from the insertion position to a use position and/or away from the first support. The force may be removed and/or reduced below that level to allow the device to return to the insertion position and/or into contact with the first support.

One or more of the releasable fasteners may be of the following form. The fastener may include a compressible element, such as a spring and in particular a conical spring between a part of the fastener and a part of the first support. The compressible element may be provided on the side of the first support which is the opposing side to that contacted by the device. Tightening of the fastener and/or displacement of the device from the first support may compress the compressible element. Untightening of the fastener and/or the device approaching the first support may decompress the compressible element. The fastener may be provided with a locking nut and/or washer, preferably on the same side of the first support as that which is contacted by the device.

The device may include the structure providing the investigation step and/or detection step and/or electrophoresis step and/or analysis step and/or results output step. The device may not include the structure providing the investigation step and/or detection step and/or electrophoresis step and/or analysis step and/or results output step. The structure providing the investigation step and/or detection step and/or electrophoresis step and/or analysis step and/or results output step may be provided on an element. The element may be separate from the device. The structure may be the channel(s) and/or chamber(s) and/or electrode(s) for the step, for instance for an electrophoresis step.

The element may be made of a different material and/or to a different manufacturing tolerance to the device.

The element may be mounted on the carrier.

The element may be mounted on the carrier with the carrier outside of the instrument. The element may be mounted on the carrier before use. The element may be removed from the carrier with the carrier outside of the instrument. The element may be removed from the carrier after use.

The carrier may provide support and/or protection for the device and/or element. The carrier may interact with the instrument and/or casing and/or device location and/or device to instrument interface, for instance to position the device and/or element correctly relative to the device to instrument location. The carrier may be held by the user when inserting the device and/or element into the instrument and/or when removing the device and/or element from the instrument.

The carrier may include a second support. The second support may receive the element. The second support may be rectilinear in profile.

The second support may extend in a second direction. The second direction may be perpendicular, +/−15°, to the first direction in which the first support extends. The maximum extent of the second support in the second direction may be less than 50% and even less than 35% of the maximum extent of the first support in the first direction.

The element may be connected to the second support by cooperation of one or more parts of the element with one or more parts of the second support. The one or more parts of the element may be opposing ends of the element. The one or more parts of the second support may be a pair of slots provided in the second element. The element may be inserted into the second support in a first direction and may be removed therefrom in a second direction which is the reverse of the first direction. The first and/or second directions may be in the plane of the element and/or second support.

A releasable and/or adjustable fastener provided on the second support may engage with a part of the element. For instance, a protrusion may cooperate with a recess.

The device may be connected to the element, for instance to allow the passage of fluid from the device to the element. The connection may be formed by the insertion of the device into the first support and/or the element into the second support. The connection may be a tube, for instance a flexible tube. The carrier may accommodate and/or support the tube. The carrier may include a first aperture through which the tube passes from the device. The aperture may lead to a void within the carrier. The carrier may include a second aperture through which the tube passes from the void to the element. The tube may make a first turn from the plane of the device into the plane of the element, ideally within the carrier. The tube may make a second turn into alignment with a channel within the device, ideally within the carrier.

The carrier, including the device and/or element, may be inserted into the instrument, for instance into a slot, for instance accessed from the work surface. The carrier may be inserted until one or more parts thereof abut one or more parts of the slot and/or work surface and/or instrument and/or casing.

The carrier may be in an insertion position when further inward movement is stopped. The insertion position may provide the device, in opposition to the device to instrument interface, but spaced therefrom.

The device may be moved from the insertion position to a use position, for instance in which the device contacts the device to instrument interface. The movement to the use position and/or a subsequent step may provide for one or more or all of the following: the application of force to the device to hold it in position against the device to instrument interface; the formation of contact between the element or that part of the device providing the electrophoresis step with a heater board; the formation of electrical contacts between the instrument and one or more electrical components, such as electrochemical pumps, provided on the device; the formation of electrical contacts between the instrument and one or more electrical components, such as electrodes, provided on the element or that part of the device providing the electrophoresis step and/or the deactivation of one or more interlocks, for instance for the power supply or one or more parts thereof or the light source.

The device may be moved from the insertion position to the use position by contact between a displacement element with the device. For instance, a platen may be advanced from a non-contact position to a contact position and then to a displacing position. In the non-contact position, the displacement element may be outside of the slot into which the carrier and cartridge are inserted. In the contact position, the displacement element may be inside the slot and/or in contact with the device. The displacement element may pass through an opening from which the carrier and/or first support is absent, but in which the device is present. In the displacing position, the displacement element may move the device away from the carrier and/or first support. The device is preferably still connected to the carrier and/or first support by the one or more releasable fasteners.

The device may engage one or more elements on the device to instrument interface and/or extending there through, particularly during the transition from insertion position to use position. The elements may be a male element, such as a dowel, on one of the device or instrument, preferably with a female element, such as a recess, on the other. Some or all of the male elements may be provided on the device. Some or all of the female elements may be provided on the device. Some or all of the male elements may be provided on the instrument. Some or all of the female elements may be provided on the instrument. The arrangement of the elements may be such that the device can be positioned in the device location given one orientation of the device. The arrangement of the elements may be such that the device can be positioned in the device location given one orientation of the device. The arrangement of the elements may be such that the device cannot be positioned in the device location given one or more orientations of the device.

The device may be moved from the use position to the insertion position by withdrawal of a displacement element. The displacement element may be withdrawn from a displacing position to a contact position, for instance to thereby allow the device to move from the use position to the insertion position, most preferably due to expansion of a compressible element. The displacement element may be withdrawn from a contact position to a non-contact position, for instance to allow the carrier and/or device to be removed, for instance from the slot.

The device may be capable of movement relative to the carrier when provided on the carrier. The device may be capable of independent lateral and/or vertical and/or horizontal movement relative to the carrier. The element may be capable of movement relative to the carrier when provided on the carrier. The element may be capable of independent lateral and/or vertical and/or horizontal movement relative to the carrier. The movement relative to the carrier may be used to move the device and/or element from a insertion position to a use position or more preferably from a first use position to a second optimised use position. In the optimised use position, the device and/or cartridge is positioned in the optimum position relative to the device to instrument interface and/or element to instrument interface and/or optical system and/or temperature control system.

The relative movement for the device and/or element may be made in response to one or more alignment checks, for instance conducted by the instrument.

The device may include a section providing one or more of a sample receiving step and/or sample preparation step and/or sample extraction step and/or sample retention step and/or purification step and/or washing step and/or elution step and/or amplification step and/or PCR step and/or denaturing step and/or investigation step and/or detection step and/or electrophoresis step and/or analysis step and/or results output step. The device may include a further section providing one or more of the steps not provided by the section. A carrier may be provided for the section and further section. The section and further section may be capable of movement relative to the carrier when provided on the carrier. The section and/or further section may be capable of independent lateral and/or vertical and/or horizontal movement relative to the carrier. The movement relative to the carrier may be used to move the section and/or further section from an insertion position to a use position or more preferably from a first use position to a second optimised use position. In the optimised use position, the device and/or cartridge is positioned in the optimum position relative to the device to instrument interface and/or element to instrument interface and/or optical system and/or temperature control system.

The relative movement for the section and/or further section may be made in response to one or more alignment checks, for instance conducted by the instrument.

The device may include one or more of a sample receiving step and/or sample preparation step and/or sample extraction step and/or sample retention step and/or purification step and/or washing step and/or elution step and/or amplification step and/or PCR step and/or denaturing step and/or investigation step and/or detection step and/or electrophoresis step and/or analysis step and/or results output step. The device may be capable of movement relative to the carrier when provided on the carrier. The device may be capable of independent lateral and/or vertical and/or horizontal movement relative to the carrier. The movement relative to the carrier may be provided before and/or after one or more of the steps of a sample receiving step and/or sample preparation step and/or sample extraction step and/or sample retention step and/or purification step and/or washing step and/or elution step and/or amplification step and/or PCR step and/or denaturing step and/or investigation step and/or detection step and/or electrophoresis step and/or analysis step and/or results output step. The movement relative to the carrier may be provided before a sample extraction step. The movement relative to the carrier may be provided before an investigation step and/or detection step and/or electrophoresis step and/or analysis step and/or results output step. A plurality of different movements may be provided. A first movement may be provided to position and/or align and/or bring into contact the device and the device to instrument interface with respect of one or more of the steps of a sample receiving step and/or sample preparation step and/or sample extraction step and/or sample retention step and/or purification step and/or washing step and/or elution step and/or amplification step and/or PCR step and/or denaturing step. A second movement may be provided to position and/or align and/or bring into contact the device and the device to instrument interface with respect to one or more of the steps of an investigation step and/or detection step and/or electrophoresis step and/or analysis step and/or results output step The relative movement for the section and/or further section may be made in response to one or more alignment checks, for instance conducted by the instrument.

The insertion of the carrier into the instrument may provide contact between the element or that part of the device providing the electrophoresis step and the device to instrument interface or a section thereof.

The contact may include one or more protrusions on the device to instrument interface interacting with one or more apertures provided in the carrier and/or second support and/or element or that part of the device providing the electrophoresis step. The contact may result in movement of the element or that part of the device providing the electrophoresis step relative to the carrier.

The contact may include contact between the element or that part of the device providing the electrophoresis step with a heated surface or location. The heated surface or location may be in the form of a thermally conductive block or heat sink, preferably provided in contact with one or more heaters. The heated surface or location may provide a planar surface portion. The heated surface or location may contact a planar surface by the channel, for instance by the electrophoresis cartridge section. The heated surface or location may have a planar surface portion whose boundaries match those of the planar surface of the channel, for instance as provided by the electrophoresis cartridge section. The heated surface or location may be bounded by one or more protruding or elevated sections. The protruding or elevated section(s) may surround the heated surface or location and/or the planar surface of the channel. The heated surface or location may be recessed compared with one or more sections provided in proximity thereto. The section(s) may surround the heated surface or location and/or the planar surface of the channel. The channel or electrophoresis cartridge section containing the channel may fit into the heating location. A snug fit may be provided.

The insertion may include the step of inserting a section of the device into a slot within the device location in the instrument. The slot may be provided in the upper section of the device location, for instance the upper 25%. The slot may be provided by a component of the instrument and particularly a component of the interface element. The component of the interface element may be in the form of a pair of supports, such as calipers, which extend partially across each side of the device. The section of the device may be the section of the device which includes the amplification step and/or PCR step and/or a chamber for providing amplification and/or PCR.

The slot may be provided between a first element and a second element. The first element and/or second element may include a heater and/or a cooler and/or a fan. The first element and/or second element may include a Peltier device, preferably a Peltier heater. The first element and/or second element may provide one or more temperature sensors. The first element may have two or more positions, particularly with one of the positions providing a larger separation in the slot between the first element and the second element, than one or more of the other positions. The second element may be fixed in position. The first element may be biassed towards a position with a separation in the slot which is less than in one or more of the positions. The positions may be varied by the first element moving perpendicular to the plane of the device location and/or device.

The connection between the pump and the operating electronics for the device location may be provided by abutting contacts. The contacts may abut when the device is introduced to the device location and/or when the door of the instrument is closed. The elements of the operating electronics for the device which contact the device and/or elements mounted thereon are preferably mounted on or in the device to instrument interface.

The operating electronics for the device to instrument interface may be, at least in part, mounted on or in the device to instrument interface. The operating electronics for the device to instrument interface may include one or more power supply controllers and/or one or more heater controllers and/or one or more temperature controllers and/or one or more actuator controllers and/or sensor monitors and/or voltage controllers.

The power supply may include a power supply for the pumps provided in the device. The power supply may include a power supply for one or more heaters provided in or on the device to instrument interface. The power supply may include a power supply for one or more coolers provided on or in the device to instrument interface. The power supply may include a power supply for the actuator for a magnet. The power supply may include a power supply for one or more fans, particularly fans for a Peltier heater. The power supply may include a power supply for an electrophoresis step. The power supply may include a power supply for a light source. The power supply may include a power supply for a light detector. The power supply may include a power supply for an optics alignment and/or verification and/or calibration components.

According to a sixth aspect of the invention, there is provided a method of producing a device, the method including:

forming one or more sample processors;

providing electronics for operating the sample processors.

According to a seventh aspect of the invention, there is provided a method of analysing a sample, the method including:

applying one or more process steps to the sample;

obtaining one or more results from the method.

The fifth and/or sixth and/or seventh aspects of the invention may include any of the features, options or possibilities set out elsewhere in this application, including in the other aspects of the invention, the specific description of the embodiments and the drawings.

Any of the aspects of the invention may include any of the following options, features or possibilities.

The sample may be received from one or more of: a swab, a buccal swab, a cotton swab, a soft swab, a solution, a suspension, an item of clothing, an item placed in the mouth, a cigarette or piece thereof, chewing gum or saliva.

The sample may be a skin sample, blood sample, cell sample, bodily fluid sample, hair sample, saliva sample or sample containing one or more of these.

The sample may be a forensic sample. The sample may be a medical sample.

The analysis may be for diagnostic purposes. The analysis may be for forensic purposes.

The analysis may be for use in the consideration of marker targets, diagnostic assays, disease markers, biobanking applications, STR based targets in transplants, identification of drug resistant microorganisms, blood testing, mutation detection, DNA sequencing, food analysis, pharmogenetics and pharmogenomics, medical fields, biotech fields, in determining familial relationships, paternity testing and pedigree testing in animals.

The analysis may be for use in border control, security or customs situations and/or uses.

The device may be a microfluidic device. The instrument may incorporate a microfluidic device. The device may be a device processing a sample of less than 1 ml, possibly less than 500:1, possibly less than 250:1, potentially less than 200:1, possibly less than 175:1, possibly less than 50:1, preferably less than 30:1, more preferably less than 20:1, potentially less than 10:1 in one or more steps. The device may be a device processing a fluid, particularly a liquid, of less than 50:1, preferably less than 30:1, more preferably less than 20:1, potentially less than 10:1 in one or more steps.

The device may process and/or contain a fluid, particularly a liquid, of less than 50:1, preferably less than 30:1, more preferably less than 20:1, potentially less than 10:1 in one or more of the following steps: a sample receiving step and/or sample preparation step and/or sample extraction step and/or sample retention step and/or purification step and/or washing step and/or elution step and/or amplification step and/or PCR step and/or denaturing step and/or investigation step and/or electrophoresis step and/or analysis step and/or results output step.

The device may incorporate one or more channels or chambers with a maximum dimension of less than 1000:m, possible less than 750:m and preferably less than 550:m.

The device may incorporate one or more channels or chambers with a maximum dimension of less than 500:m, possible less than 250:m and preferably less than 100:m.

The device may include a chambers provided with one or more reagents. One or more chambers may be so provided. The reagents may be different. The reagents may be in liquid form. The reagents may be in liquid and/or solid and/or gel form. The reagents may be provided on and/or in the surface of a solid. The solid may be one or more beads. The solid may be magnetic.

One or more reagents may be provided for cell lysis. One of more reagents may be provided for a selective extraction of DNA containing material from other material. One or more reagents may be provided for washing. One or more reagents may be provided for elution, particularly from the surface of a solid. One or more reagents may be provided for amplification, particularly PCR based amplification. One or more reagents may be provided for denaturing. One or more reagents may be provided for electrophoresis.

Preferably the device has a stored form and a use form. In the use form, the sample to be processed may be loaded into the device. Preferably one or more reagents are pre-loaded into the device and/or are present in the device when in the stored form. One or more reagents may be loaded into the device in the use form.

The device and/or method may include one or more pumps. Preferably the device only includes pumps of a single type. Preferably the pumps of the single type are identical with respect to chamber shape and/or electrode positions and/or electrode materials and/or orientation and/or chamber volume and/or pump electrolyte and/or pump electrolyte concentration.

One or more, preferably all, of the pumps may be electrochemical pumps.

The device may have an orientation of use, preferably one electrode in the pump chamber is provided above the other. The pump chamber may have a height greater than its width. The pump chamber may have a width greater than its depth.

The pump chamber may have an outlet. Preferably the outlet is provided in the upper section of the pump chamber. The upper section may be the upper 20%, preferably 10%, and more preferably 5% of the height of the chamber. The outlet may be in the top wall of the chamber.

The pump chamber may contain NaCl. The molarity of the electrolyte in the pump chamber may be between 0.2M and 3M, preferably 1M+/−15%.

The electrophoresis step and/or electrophoresis cartridge section may be provided with a channel, for instance a capillary for electrophoresis.

The channel may be provided with a matrix. Preferably the matrix resists the passage of elements, the resistance being related to the size of the element. Preferably different size elements migrate through the matrix at different rates, the larger migrating slower.

The channel may be provided with an inert bed of particulate material to form the matrix.

The channel may be provided with a gel, particularly a polymer gel. The gel may be cellulose based. The channel may be provided with polyhydroacrylamide, polydimethylacrylamide or mixtures there of The channel may be provided with a cross-linked polymer. The cross-linking of the polymer may be provided in situ.

One or more surfaces of the channel may be treated, for instance with a hydrophilic coating, for instance poly(hydroxyethlacrylamide).

The channel may be provided with a matrix during electrophoresis. The channel may be provided without a matrix prior to electrophoresis, with the matrix being introduced before electrophoresis commences. The matrix or a material for forming the matrix may be stored at a location removed from the channel in which electrophoresis is provided. The matrix or material for forming the matrix may be stored in a chamber. The chamber may be connected by a channel to the channel in which electrophoresis is provided.

The matrix and/or material for forming the matrix may be altered before use in the electrophoresis step. The alteration may be provided before and/or during and/or after the matrix and/or material for forming the matrix is provided in the channel. The alteration may be polymerisation. The alteration may be caused and/or triggered by heating and/or the application of light, such as U/V light. The alteration may be applied to all of the matrix and/or material for forming the matrix or only a part thereof. One or more parts of the matrix may be prevented from alteration, for instance by masking those parts and/or excluding heat and/or excluding light from them.

BRIEF DESCRIPTION OF THE DRAWINGS

Various embodiments of the present invention will now be described, by way of example only, and with reference to the accompanying drawings in which:

FIG. 3b is a table of dimensions and volumes for a cartridge according to the present invention, and components thereof;

FIG. 7 is an illustration of an alternative structure for providing sample to the PCR chamber;

FIG. 8 is a front view of the electrophoresis cartridge section showing an alternative form of injector;

FIG. 12 is a schematic front view of one embodiment of the instrument;

FIG. 13 is a side view showing the insertion of the cartridge into the instrument;

FIG. 28b is a table of dimensions and volumes for the FIG. 28a cartridge;

FIG. 29a is a perspective view of an embodiment of the instrument;

FIG. 29b is a front view of the instrument of FIG. 29a;

FIG. 29c is a side view of the instrument of FIG. 29a;

FIG. 30 is a perspective view of another instrument embodiment;

FIG. 35a is an illustration of the cartridge and carrier in the insertion form;

FIG. 35b is an illustration of the cartridge and carrier in the use form;

FIG. 35c is an illustration of the cartridge returned to the carrier;

FIG. 37a is a perspective view of the second support of the carrier and CE chip;

FIG. 37b is a partial cut away illustration of the second support and CE chip;

FIG. 42a shows a CE chip embodiment;

FIG. 42b shows a detail of the CE chip of FIG. 42a;

DETAILED DESCRIPTION OF THE PREFERRED EMBODIMENTS

Figure 1:
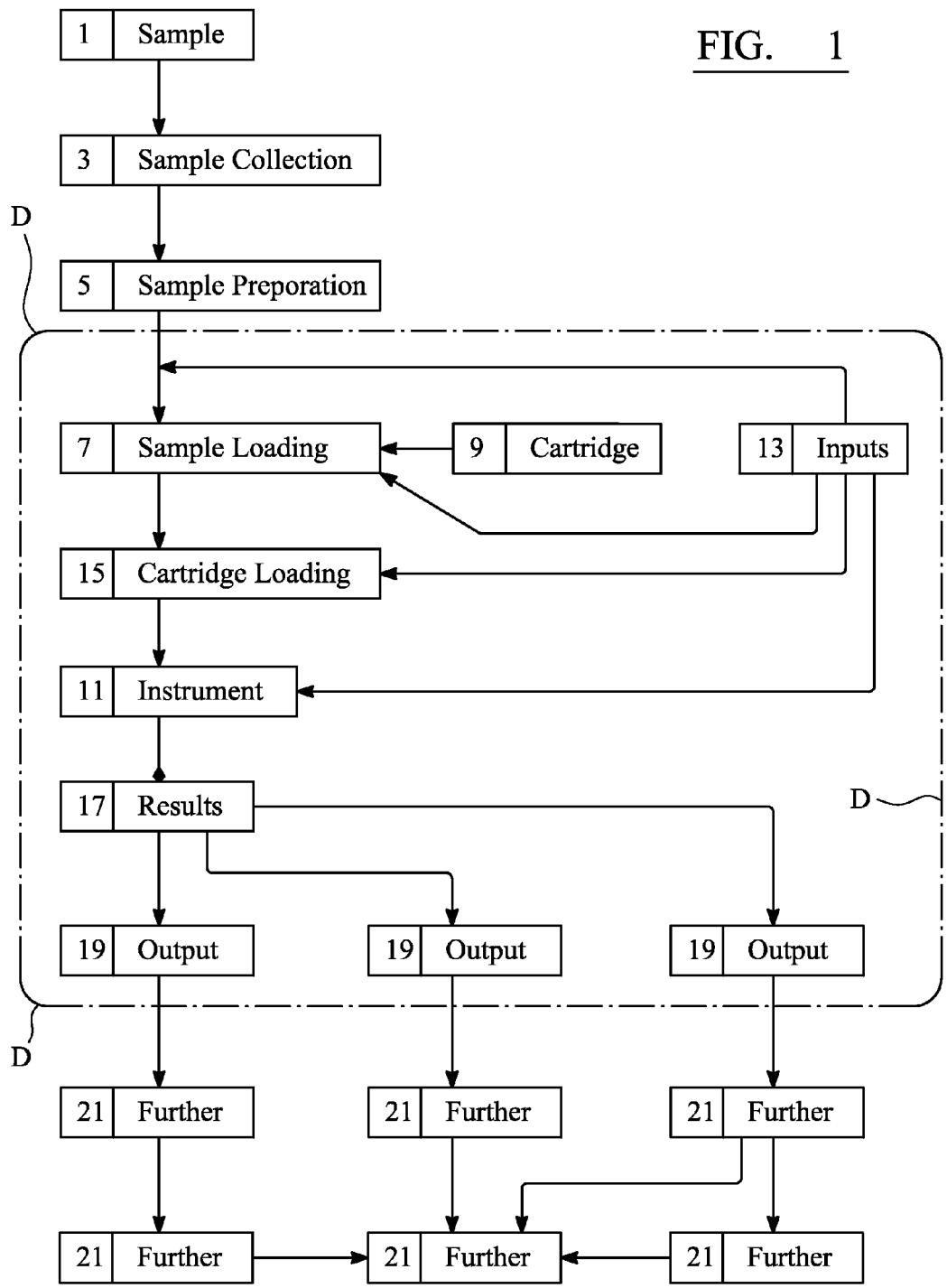
FIG. 1 is a schematic illustration of the stages involved in the consideration of a sample from collection to results and illustrates the positioning of the embodiments of the present invention in that context.

In a variety of cases it is desirable to be able to analyse a biological sample to obtain information on the sample and/or one or more components of the sample. Such cases include medical diagnostics, for instance to look for disease markers, and forensic science, for instance to establish a DNA profile.

At present, such analyses are conducted by highly trained scientists in a laboratory environment. This means that a significant amount of effort and experience goes into the handling of the samples, the use of the analysis equipment and the formulation of the conclusions reached. However, the need to convey the sample to a laboratory environment and then receive the results back from the laboratory environment introduces a potential time delay between obtaining the sample and obtaining the results thereon. The need to use a laboratory environment and highly trained scientists potentially adds to the time required, as the supply of such people and resources is limited. The need to use a laboratory environment and highly trained scientists potentially adds to the cost as there are capital and running costs associated with such facilities and the scientists.

If fewer laboratory style environments are to be used for the analysis or the staff used are less specialised, then there is the potential for problems with the analysis, unless a proper and reliable system is provided.

The present invention has amongst its potential aims to enable analysis of samples at a greater variety of locations and/or non-laboratory type locations. The present invention has amongst its potential aims to enable analysis by personnel having a lower level of training and/or experience. The present invention has amongst its potential aims to enable lower cost and/or faster analysis of samples. The present invention has amongst its potential aims to enable greater use and/or more successful use of analysis by law enforcement authorities.

Many of the concepts and issues to be addressed by the invention are best understood by way of the following examples. It should be noted, however, that these examples are by their very nature detailed and exhaustive, and that benefits from the present invention arise even when only small sections of the examples are implemented in other embodiments of the present invention.

The various embodiments and examples explain the invention initially in the context of a reference sample; that is a sample collected from a known individual under controlled conditions. An example of a reference sample would be a sample collected by a swab from the buccal cavity of a person who has been arrested, the sample being collected at a police station. The invention is also suited to casework samples; that is a sample collected from a location from an unknown individual under non-controlled conditions. An example would be a spot of blood collected by a swab from a crime scene, with the source of the blood unknown. Where the differences between reference samples and casework samples have an impact on the preferred forms of the instrument, cartridge and methods, the casework sample embodiments are separately described.

The substitution of one or more components by one or more different components or different arrangements of components is also envisaged where particular conditions or issues arise. Again, after the discussion of the reference sample and casework sample contexts for the instrument, these alternatives are described.

As a starting point, it is useful to establish the context of the instrument, cartridge and methods of use in the overall context in which they may be used, by way of example. Thus in FIG. 1 there is a schematic of the overall process into which the present invention fits. This overall process includes a sample 1 which is gathered in a sample collection stage 3. This is followed by a sample preparation stage 5. In the subsequent sample loading stage 7, a prepared cartridge 9 is loaded with the collected and prepared sample 1. The next stage is the cartridge installation stage 15 in which the cartridge 9 is introduced to the instrument 11. The instrument 11 also receives various inputs 13 at the sample loading stage 7 and/or at the cartridge installation stage 15 and/or subsequently.

The structure and processes performed within the instrument 11 and cartridge 9 are described further below in the context of FIG. 2.

Once the instrument 11 has completed these stages and achieved the analysis, the next stage is the results stage 17. This is followed by one or more output stages 19, and potential further stages 21 which integrate the analysis into the criminal justice system of that jurisdiction. A wide range of possible links between the various output stages 19 and further stages 21 may be possible, with some being linked to just one stage and others be the result of multiple such stages and/or combinations thereof.

An output stage 19 may include the transmission of the results from the instrument to a remote location for processing. The processing may be performed using complex software and/or hardware tools, before the final results are returned to the instrument 11 or to another computer. Processing the results at a remote location may be preferably in terms of the size, cost or complexity of the software/hardware needed to perform the processing thus only being provided at a limited number of locations, rather than a part of each instrument.

The following description of the operation of the instrument 11, in a generally sequential manner, provides full details of the key instrument stages and their interrelationship.

Figure 2:
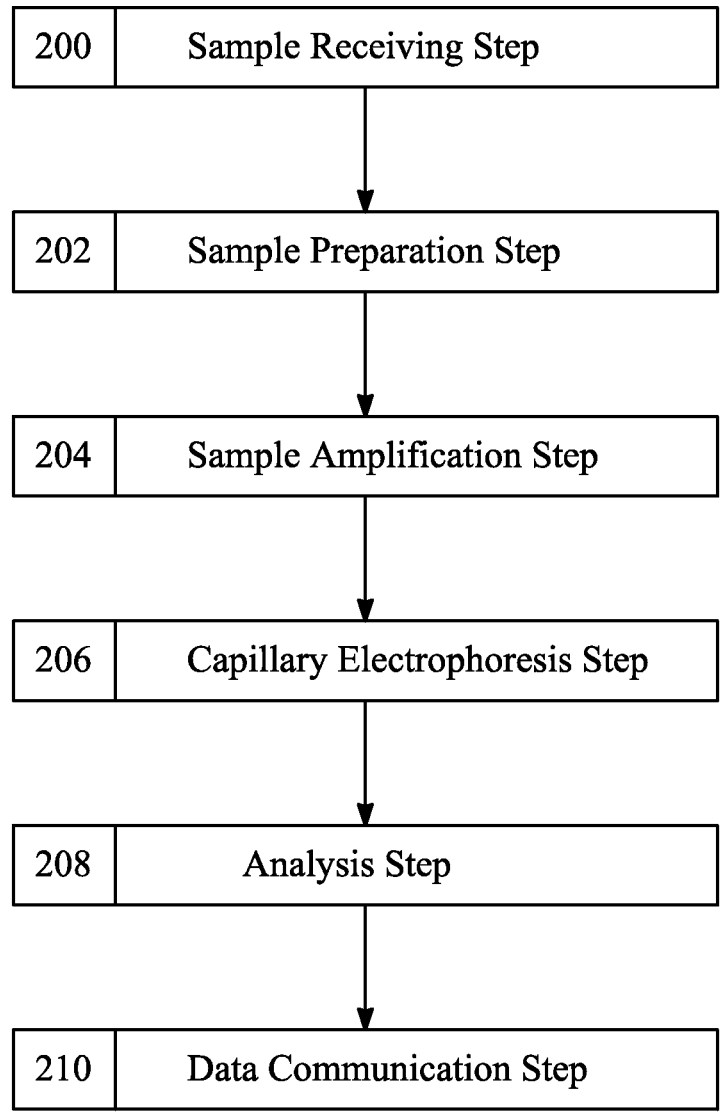
FIG. 2 is a schematic illustration of the key steps provided on or by an instrument embodying the present invention.

Referring to FIG. 2, the instrument has a sample receiving step 200, sample preparation step 202, sample amplification step 204, electrophoresis step 206 and analysis step 208 and data communication step 210.

In the sample receiving step 200, the sample 1 is transferred from a sample storage and/or processing stage 5, which is outside of the cartridge 9 and instrument 11, to a location on the cartridge 9.

The initial collection device is frequently a swab. The swab is used to pick up the sample 1 from an article or substrate.

In the sample preparation step 202, the key components within the sample are contacted with the reagents and/or components intended to prepare the sample for the subsequent steps. In this embodiment, the sample preparation step 202 contacts the sample with beads to retain the DNA and recover it, whilst the other components which are not to be recovered flow through and away. The sample preparation step 202 also includes contact with a wash agent to improve the separation of the DNA from the other components. The wash agent flows through the chamber holding the beads and retained DNA and flows to a further chamber, a waste chamber. The wash agent is followed by an elution agent to release the DNA from the beads for the subsequent steps.

In the sample amplification step 204, the DNA is contacted with amplification reagents and provided with the conditions necessary to achieve amplification through PCR.

In the electrophoresis step 206, the amplified DNA is conveyed to a start point for a mobility based separation within a capillary. An electric field is then used to separate the complex DNA amplicons into different size clusters.

In the analysis step 208, the channel is inspected to establish the relative position and hence size of elements detected in the capillary. This is achieved by an excitation light source, fluorescent markers associated with the elements to be detected and suitable optics to detect the fluorescent light resulting.

In the data communication step 210, the instrument compiles the necessary data packet for transmission and transmits it to a remote location for consideration. The data packet includes information on the electrophoresis results, sample identity and other information. The analysed results may be received by the instrument as part of the data communication step 210.

Some data processing may be performed on the instrument itself, for instance to deconvolute the analysis results to indicate the peaks indicative of alleles present.

The instrument can be provided in a format which considers a single sample at a time, or can be provided in a format which considers multiple samples at a time. The multiple samples may each be run on separate cartridges, but modified cartridges which handle multiple samples are possible. The handling of multiple cartridges is beneficial in allowing a single set of controllers, power supplies, optics and the like to consider multiple samples, with reduced capital costs.

Cartridge

Key to the operation of the instrument is a disposable, single use cartridge 9. This cartridge 9 is intended to only process and provide the results for analysis on a single occasion. The disposable nature of the cartridge 9 places a number of constraints on the cartridge 9 in terms of the materials which can be used, because of the need to keep manufacturing, assembly or purchase costs low.

The detailed layout of the cartridge 9 is now described. Later, a description of the sequence of operation of the elements which make up the cartridge is provided.

Figure 3A:
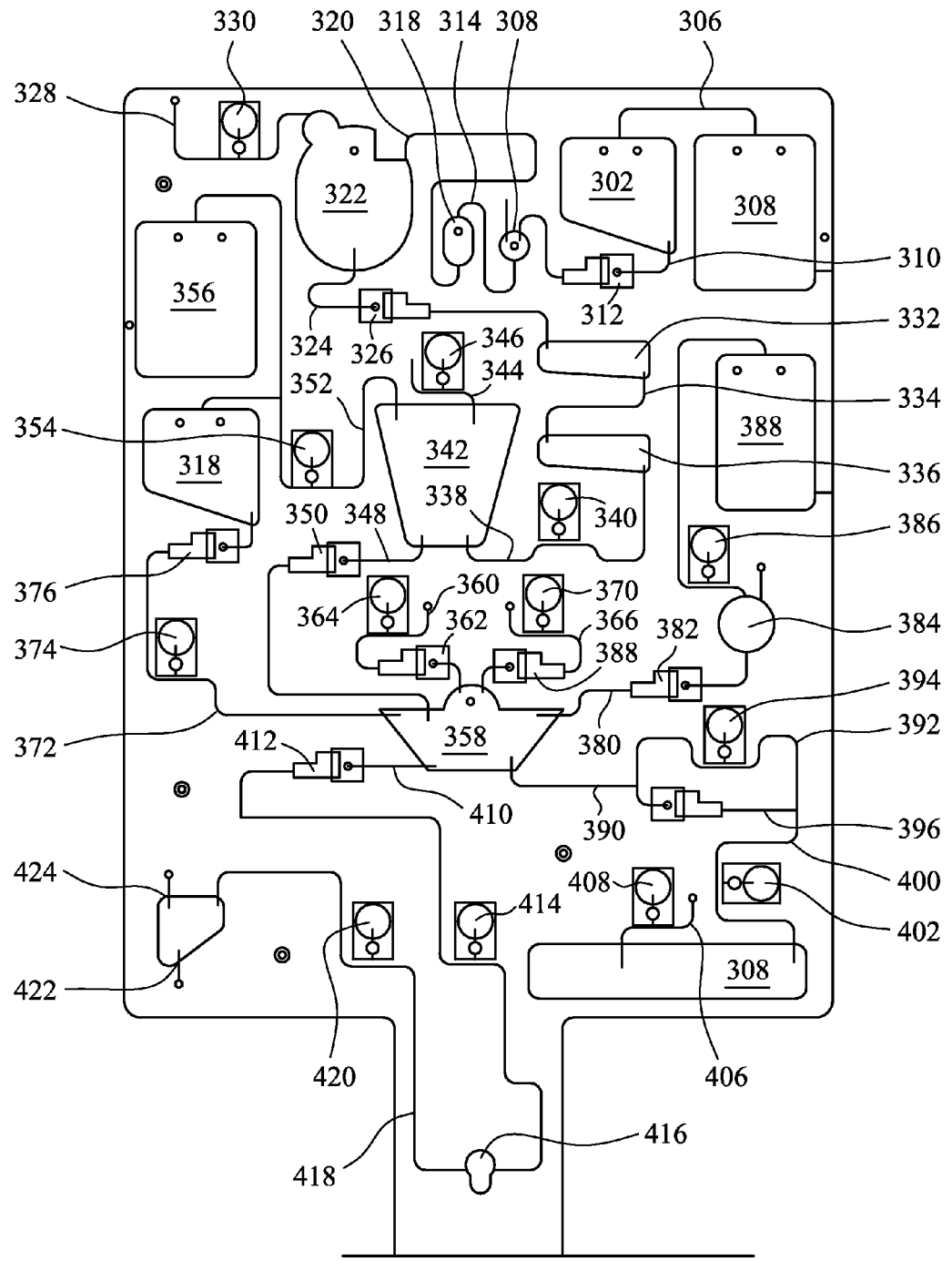
FIG. 3a is a front face view of part of a cartridge embodying the present invention.

FIG. 3a is an illustration of that part of the sample receiving step 200 provided on the cartridge 9, the whole sample preparation step 202 and the whole sample amplification step 204. The subsequent steps and their respective pasts of the cartridge 9 are illustrated separately.

FIG. 3b provides details of the volumes of the various chambers used, the depths (into the page in effect) for the various components and the overall dimensions of this part of the cartridge 9.

The cartridge 9 is provided with a sample introduction chamber 302 connected to a channel 304 leading to the outside of the cartridge 300. This forms those parts of the sample receiving step 200 provided on the cartridge 9.

The sample preparation step 204 follows. To provide this, the sample introduction chamber 302 is connected to a pumping fluid channel 306 and hence to a first electrochemical pump 308. The sample introduction chamber 302 has an outlet channel 310 which passes valve 312 and provides an inlet to purification buffer chamber 314. Valve 312 is initially open.

Purification buffer chamber 314 is connected via channel 316 to bead storage chamber 318. The bead storage chamber 318 is connected via channel 320 to initial mixing chamber 322. The outlet channel 324 from initial mixing chamber 322 is blocked by closed valve 326, but a vent channel 328 is open because valve 330 is open initially.

The outlet channel 324 leads past valve 326 to a first further mixing chamber 332 and then through channel 334 to second further mixing chamber 336. The outlet 338 from the second further mixing chamber 336 leads past valve 340 to incubation chamber 342, where bubble mixing assists the DNA to bead binding process.

The incubation chamber 342 has a vent channel 344 provided with valve 346 and an outlet channel 348 which is initially closed by valve 350. The incubation chamber 342 is also provided with a pumping fluid inlet channel 352 which passes valve 354 and is connected to second electrochemical pump 356.

The outlet channel 348 from the incubation chamber 342 leads to capture chamber 358 where the beads and hence bound DNA are collected. The capture chamber 358 is provided with a first vent channel 360 which passes first valve 362 and second valve 364. The capture chamber 358 is also provided with a second vent channel 366 which passes first valve 368 and second valve 370.

Also connected to capture chamber 358 is wash buffer channel 372. The wash buffer channel is connected to first valve 374 and second valve 376 and leads from second electrochemical pump 356 through wash buffer chamber 378 to the capture chamber 358.

Also connected to capture chamber 358 is an elution liquid channel 380. The elution liquid channel 380 is connected to first valve 382, elution liquid storage chamber 384, second valve 386 and back to third electrochemical pump 388.

The capture chamber 358 has a wash outlet channel 390 which splits into a first wash outlet channel section 392 which passes valve 394, and into a second wash outlet channel section 396 which passes valve 398. After passing their respective valves 394, 398, the first wash outlet channel section 392 and second wash outlet channel section 396 rejoin one another to form further wash channel 400. The further wash channel 400 leads past valve 402 into waste chamber 404. The waste chamber 404 is vented along vent channel 406 past valve 408. These elements provide the sample preparation step 202.

To provide the sample amplification step 204, capture chamber 358 is also provided with elution outlet channel 410 which leads past valve 412 and past valve 414 and into PCR chamber 416. The outlet channel 418 from the PCR chamber 416 leads past valve 420 into archive chamber 422. The archive chamber 422 is vented through vent channel 424. The role of the archive chamber 422 is described further below.

Provided within the PCR chamber 416 is a bead loaded with the reagents, a multimix, needed for the PCR process. The reagents/multimix include primers dNTPs and PCR reaction mix, including Tris buffer, $MgCl_2$, NaCl and BSA. These reagents are released into the sample once it contacts the bead in the PCR chamber 416 and the temperature is raised above ambient temperature.

The above circuit overall, is sufficient to receive, retain, wash, elute and perform PCR on the sample, as well as storing the waste from the process and an archive of the PCR product.

Subsequently, the arrangement shown in FIG. 4 can be used to transfer the now amplified DNA from the PCR chamber 416 into the electrophoresis step 206.

Figure 4:
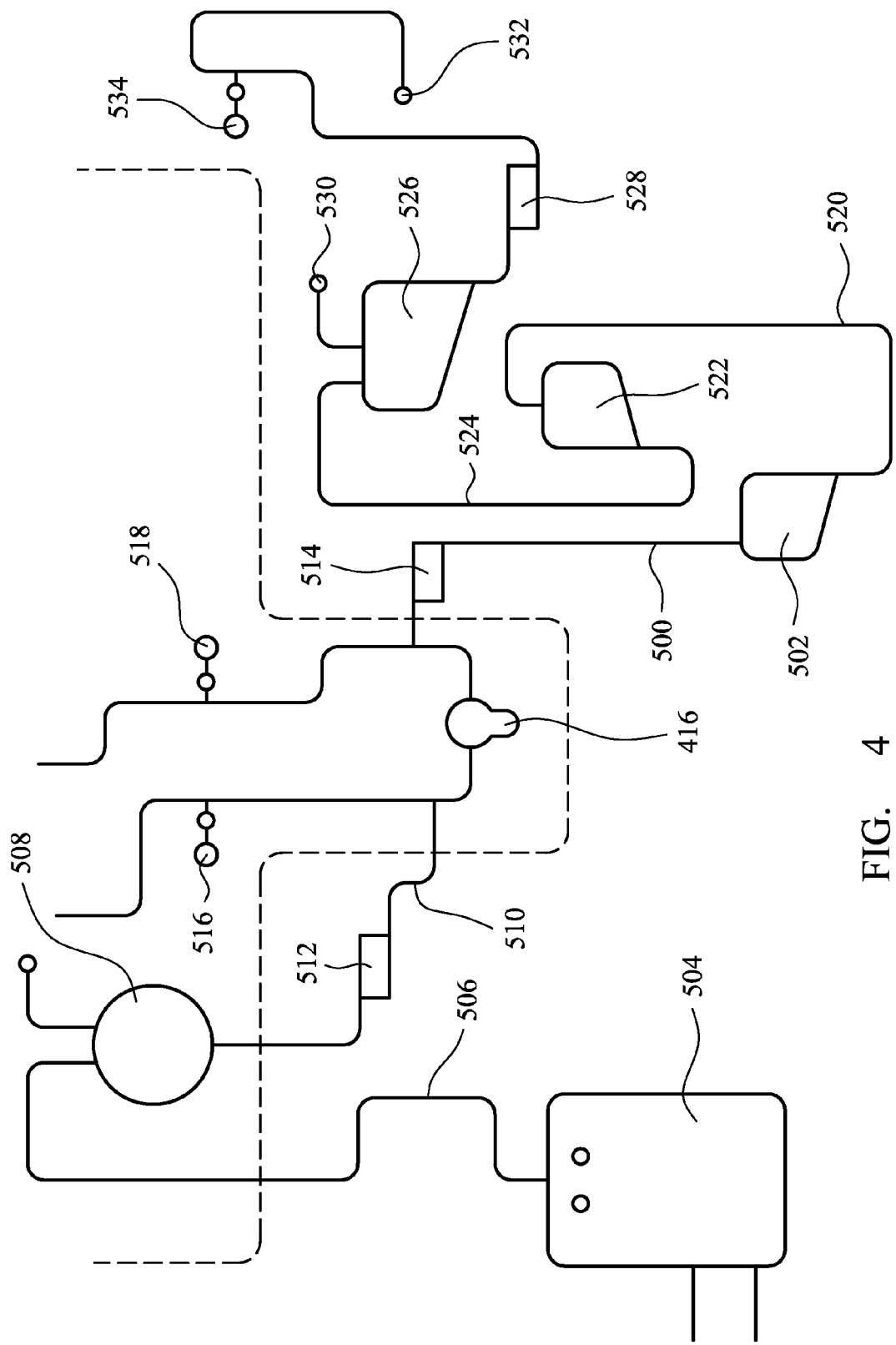
FIG. 4 is a front face view of a further part of the cartridge of FIG. 3a and embodying further features of the present invention.

In FIG. 4, the PCR chamber 416 is the same PCR chamber 416 which was illustrated in FIG. 3 and described above. Other features were omitted from FIG. 3 to improve the clarity of that Figure.

Leading from the PCR chamber 416 is a denaturing feed channel 500 which is connected to an amplified material mixing chamber 502. The amplified material is pumped from PCR chamber 416 by the action of fourth electrochemical pump 504 which is connected to channel 506, hence to denaturing reagent storage chamber 508 and through channel 510 to the PCR chamber 416. Formamide is provided in the denaturing reagent storage chamber in the preferred form.

These components are isolated from the PCR chamber 416 during the sample amplification step 204 by closed valve 512 and closed valve 514. Both valve 512 and 514 are opened and valves 516 and 518 are closed to convey the amplified material away from the PCR chamber 416.

From the denaturing feed channel 500, the amplified material and denaturing reagents enter the first amplified material mixing chamber 502, pass through channel 520, into second amplified material mixing chamber 522, through channel 524 and into third amplified material mixing chamber 526. Whilst the third amplified material mixing chamber 526 fills, valve 528 is shut and vent 530 is open. An overall volume of 45:1 is provided, 5:1 from the PCR chamber and 40:1 from the denaturing reagent storage chamber 508.

The amplified material is held in the third mixing chamber 526 for the necessary time and at the necessary temperature to complete the denaturing process. Once this has been achieved, the valve 528 is opened and further pumping by the fourth electrochemical pump 504 pumps the denatured material to the electrophoresis step inlet 532. At the inlet 532, the denatured material passes out of the plane of the cartridge 9 and to the electrophoresis cartridge section behind. Once past through the inlet 532, valve 534 is shut to isolate the cartridge 9 from the electrophoresis cartridge section 600.

The overall result of this structure is the pumping of the amplified DNA to a start point for the electrophoresis step 206.

The transfer from PCR to CE steps is provided in a way which allows easy integration of the steps, does not impact upon the temperature and pressure stability required in PCR and achieves minimal sample loss during transfer. Automated mixing of the sample and size standards during transfer and possibilities for pre-concentrating the sample before CE are also rendered possible.

Figure 5A:
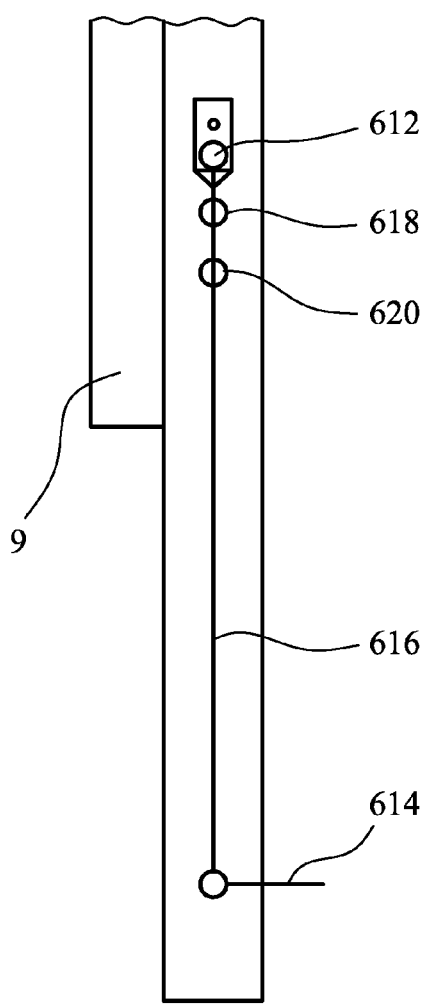
FIG. 5a is a side view of the section of the cartridge of FIGS. 3a and 4 where in joins the electrophoresis cartridge section.
Figure 5B:
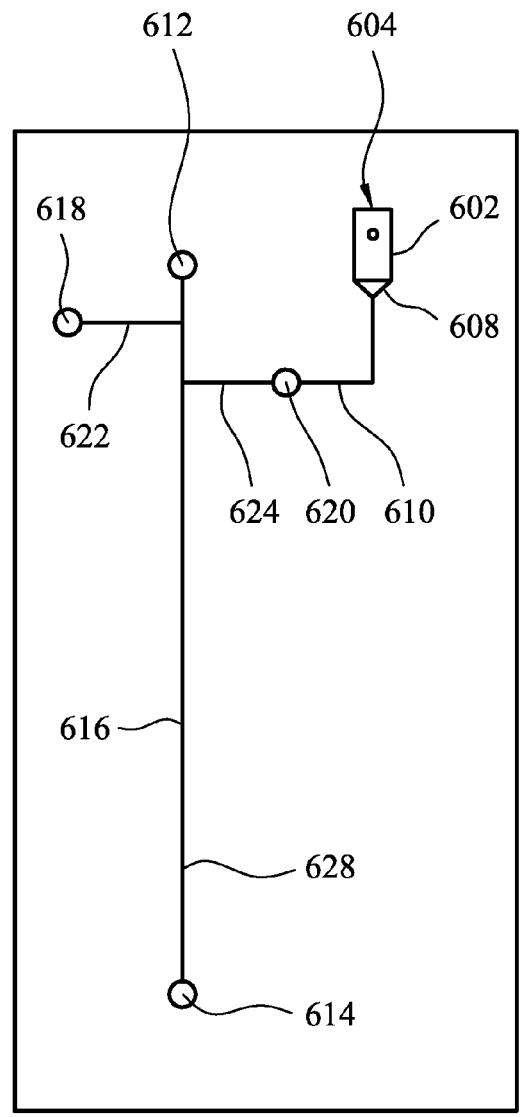
FIG. 5b is a front view of the electrophoresis cartridge section shown in FIG. 5a, with the section of the cartridge omitted.

The overall configuration of the electrophoresis step 206 can be seen in the side view of FIG. 5a and front view of FIG. 5b.

The inlet 532 leads from the plane of the cartridge 9, through into the plane of the electrophoresis cartridge section 600. Here, the inlet 532 leads into the top section 602 of an electrophoresis feed reservoir 604. The top section 602 is empty, but the lower section 606 is provided with the gel 608 which also fills the capillary 610. The sample is pumped into the electrophoresis feed reservoir 604 by a fourth electrochemical pump, not shown.

Sample flow from the reservoir 604 into the correct position within the capillary 610 is achieved using electrophoresis as the transport mechanism.

In this embodiment, the injector structure provided within the capillary cartridge section 600 is a double T injector. This includes a first electrode location 612, second electrode location 614 provided at the other end of the long capillary 616 in which the size based separation is achieved. A third electrode location 618 and fourth electrode location 620 are provided in side arms 622 and 624 respectively. The side arms are offset relative to one another, with side arm 624 further towards the second electrode location 614, than the side arm 622.

Initially, sample is drawn from the liquid phase in the reservoir 604 through the interface with the gel provided in the reservoir 604 and hence into the gel by a voltage applied to the electrode present at the third electrode location 618. Once the sample has been drawn past the fourth electrode location 620, a voltage is also applied to the electrode at the fourth electrode location. Generally, the electrode at the third electrode location may be at a voltage of 600V and the electrode at the fourth electrode location may be at a voltage of 200V. The voltage may be floating for the electrodes at the first 612 and second 614 electrode locations.

This situation results in sample being drawn along side arm 624, along the section 626 and into side arm 622, such that sample is present in the two side arms 622 and 624 and the section 626 of the capillary 616.

This gives the plug of sample upon which the electrophoresis's to act in the section 626.

To reduce the cost of the electrodes used, consistent with the cartridge being single use, platinum coated, gold coated, carbon, nickel and other lower cost electrodes may be used.

Once positioned, the separation voltages are applied: 1500V at the electrode at the second electrode location 614; 0V at the electrode at the first electrode location 612; and 200V at the electrodes present at the third electrode position 618 and fourth electrode positions 620.

The capillary 616 is filled with a gel matrix which preferentially retards the speed of progress of elements within the DNA as their size increases. The result is a size based separation of the elements, with the faster elements reaching the detection location 626 first and the slowest reaching the detection location 628 last. The different times at which the signals are generated and form the electropherogram indicate the size of the element behind that signal.

It is possible to assist in the interpretation of the unknown element sizes by using a size standard within the capillary. This is provided with a different dye colour or otherwise rendered distinct. The method set out in U.S. patent application No. 61/096,424, the contents of which are hereby incorporated by reference, offers approaches for determining the sizes of the unknowns from the size standard.

The setup and operation of the light source, optics and detector is described in detail below.

Other embodiments of the cartridge have also been developed.

Figure 27:
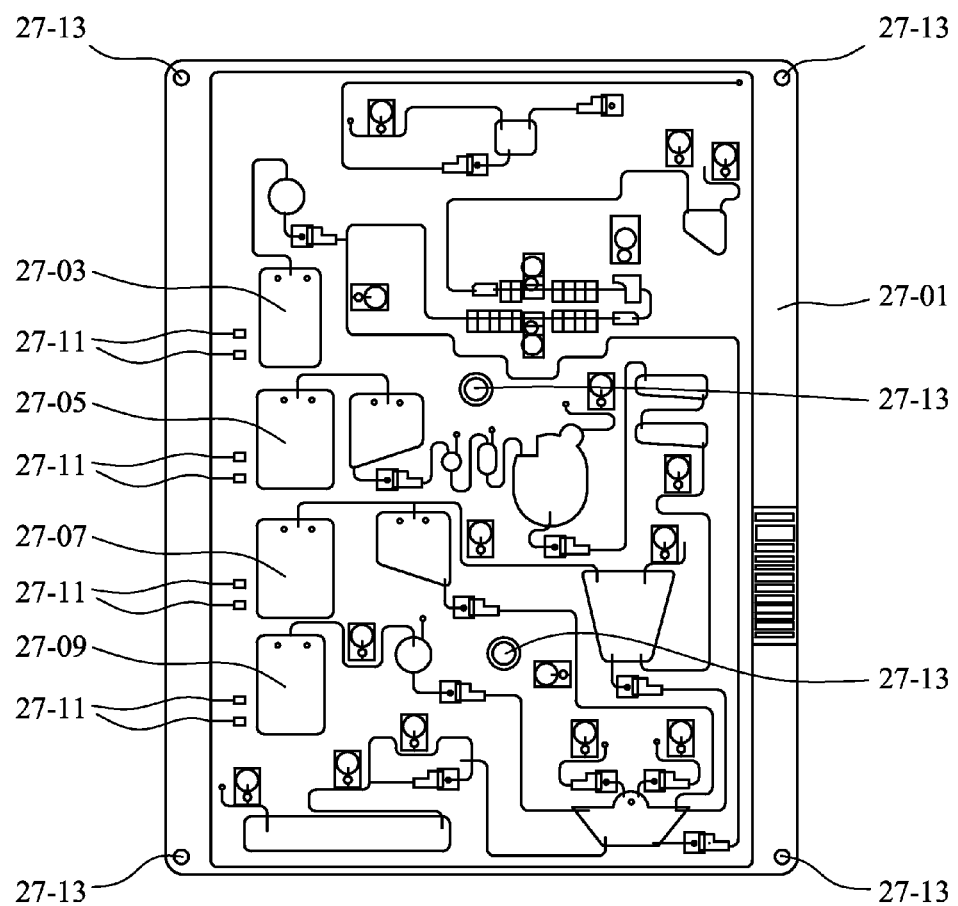
FIG. 27 is a front face view of a cartridge according to an embodiment.

As shown in FIG. 27, the cartridge 27-01 has been modified by providing the electrochemical pumps 27-03, 27-05, 27-07, 27-09 with connections between the wires leading to the electrodes in the pumps and the power source not shown of the Pogo™ pin type. The pins 27-11 are spring loaded in the recesses of the cartridge 27-01 and in use contact similar spring loaded pins (not shown) on the other side of the cartridge to instrument interface. A reliable electrical contact is thus provided and the cartridge is more robust against damage during storage, installation and use than designs in which the wires for the electrochemical pumps protruded from the side of the cartridge.

The form shown in FIG. 27 also features guide holes 27-13 which are used in the alignment of the cartridge and instrument, as described in more detail below.

Figure 28A:
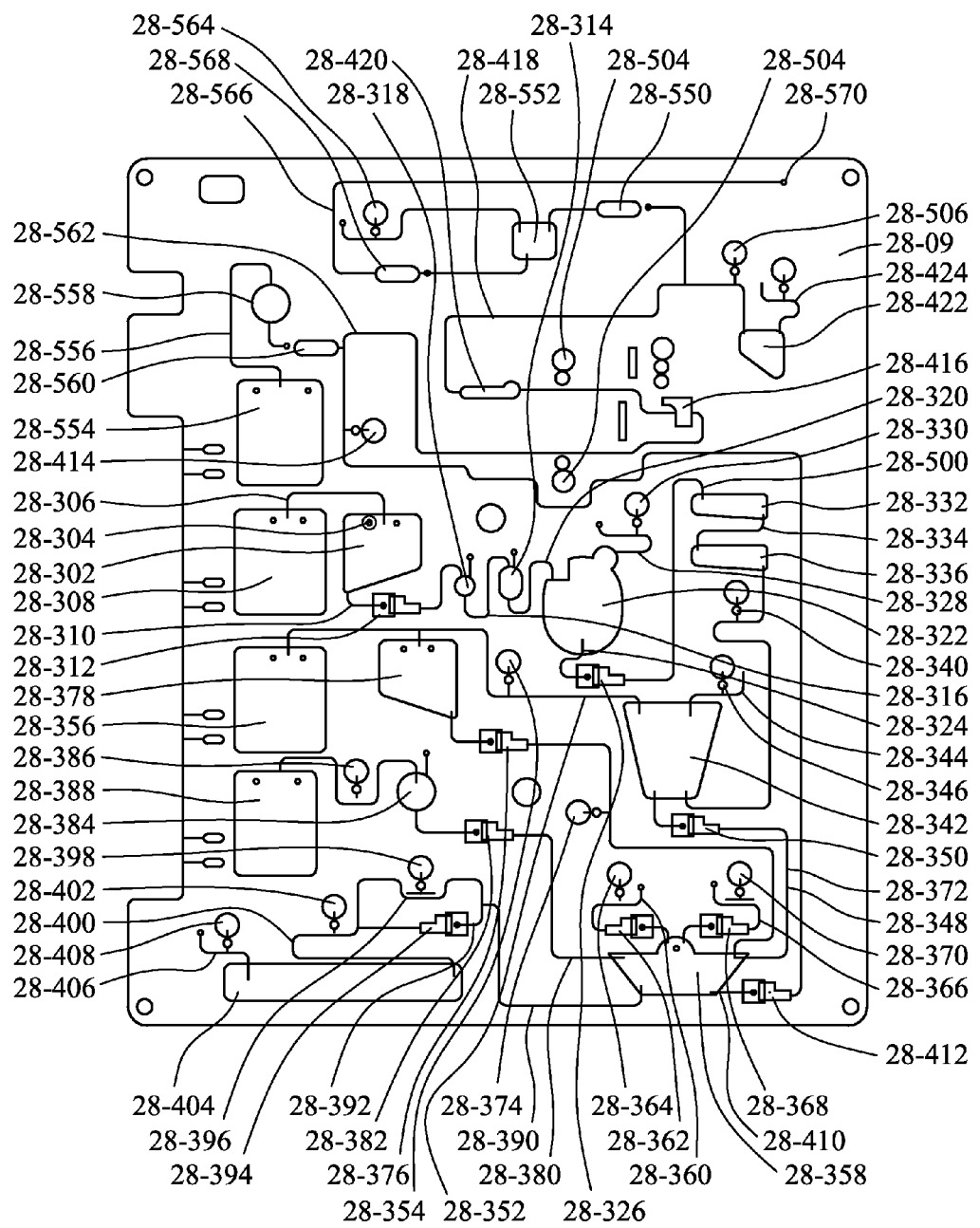
FIG. 28a is a front face view of a cartridge according to a different embodiment.

A preferred embodiment of the cartridge is shown in FIG. 28a. This is an illustration of that part of the sample receiving step 200 provided on the cartridge 28-09, the whole sample preparation step 202, the whole sample amplification step 204, the whole sample denaturation step and the feed to the capillary electrophoresis step 206.

FIG. 28b provides details of the volumes of the various chambers used, the depths (into the page in effect) for the various components and the overall dimensions of this part of the cartridge 28-09.

The cartridge 28-09 is provided with a sample introduction chamber 28-302 connected to a channel 28-304 leading to the outside of the cartridge 28-09. This forms those parts of the sample receiving step 200 provided on the cartridge 28-09.

The sample preparation step 204 follows. To provide this, the sample introduction chamber 28-302 is connected to a pumping fluid channel 28-306 and hence to a first electrochemical pump 28-308. The sample introduction chamber 28-302 has an outlet channel 28-310 which passes valve 28-312 and provides an inlet to bead storage chamber 28-318. Valve 28-312 is initially open.

The bead storage chamber 28-318 has an outlet channel 28-316 leading to binding buffer storage chamber 28-314.

This sequence of chambers is reversed compared with the FIG. 3a embodiment. The binding buffer storage chamber 28-314 has an outlet channel 28-320 which leads to mixing/purification chamber 28-322.

Mixing/purification chamber 28-322 is connected via channel 28-324 through valve 28-326 and via channel 28-500 to first further mixing chamber 28-332. The outlet channel 28-324 from mixing/purification chamber 28-322 is blocked by closed valve 28-326, but a vent channel 28-328 is open because valve 28-330 is open initially.

The outlet channel 28-324 leads past valve 28-326 to a first further mixing chamber 28-332 and then through channel 28-334 to second further mixing chamber 28-336. The outlet 28-338 from the second further mixing chamber 28-336 leads past valve 28-340 to incubation chamber 28-342, where bubble mixing assists the DNA to bead binding process. The incubation chamber 28-342 may be actively heated or may simply provide the necessary dwell time and/or other binding conditions needed.

The incubation chamber 28-342 has a vent channel 28-344 provided with valve 28-346 and an outlet channel 28-348 which is initially closed by valve 28-350. The incubation chamber 28-342 is also provided with a pumping fluid inlet channel 28-352 which passes valve 28-354 and is connected to second electrochemical pump 28-356.

The outlet channel 28-348 from the incubation chamber 28-342 leads to capture chamber 28-358 where the beads and hence bound DNA are collected. The capture chamber 28-358 is provided with a first vent channel 28-360 which passes first valve 28-362 and second valve 28-364. The capture chamber 28-358 is also provided with a second vent channel 28-366 which passes first valve 28-368 and second valve 28-370.

Also connected to capture chamber 28-358 is wash buffer channel 28-372. The wash buffer channel is connected to first valve 28-374 and second valve 28-376 and leads from second electrochemical pump 28-356 through wash buffer chamber 28-378 to the capture chamber 28-358.

Also connected to capture chamber 28-358 is an elution liquid channel 28-380. The elution liquid channel 28-380 is connected to first valve 28-382, elution liquid storage chamber 28-384, second valve 28-386 and back to third electrochemical pump 28-388.

The capture chamber 28-358 has a wash outlet channel 28-390 which splits into a first wash outlet channel section 28-392 which passes valve 28-394, and into a second wash outlet channel section 28-396 which passes valve 28-398. After passing their respective valves 28-394, 28-398, the first wash outlet channel section 28-392 and second wash outlet channel section 28-396 rejoin one another to form further wash channel 28-400. The further wash channel 28-400 leads past valve 28-402 into waste chamber 28-404. The waste chamber 28-404 is vented along vent channel 28-406 past valve 28-408. These elements provide the sample preparation step 202.

To provide the sample amplification step 204, capture chamber 28-358 is also provided with elution outlet channel 28-410 which leads past valve 28-412 and past valve 28-414 and past valve 28-502 and into PCR chamber 28-416. The outlet channel 28-418 from the PCR chamber 28-416 leads past valve 28-420 and past valve 28-504 and past valve 28-506 into archive chamber 28-422. The archive chamber 28-422 is vented through vent channel 28-424. The role of the archive chamber 28-422 is as described further above.

Provided within the PCR chamber 28-416 is a bead loaded with the reagents, a multimix, needed for the PCR process. The reagents/multimix include primers dNTPs and PCR reaction mix, including Tris buffer, $MgCl_2$, NaCl and BSA. These reagents are released into the sample once it contacts the bead in the PCR chamber 28-416 and the temperature is raised above ambient temperature.

The above circuit overall, is sufficient to receive, retain, wash, elute and perform PCR on the sample, as well as storing the waste from the process and an archive of the PCR product.

The PCR part of the circuit has been moved to the upper section of the cartridge compared with the previous embodiments so as to present it physically closer to the CE chip.

Subsequently, the further arrangement shown in FIG. 28a can be used to prepare, denaturation step, and transfer the now amplified DNA from the PCR chamber 28-416 into the electrophoresis step 206.

Leading from the PCR chamber 28-416 is outlet channel 28-418. This splits after valves 28-420 and 28-504 into a denaturing feed channel 28-550 and the channel leading to the archive chamber 28-422. The denaturing feed channel 28-550 is connected to a denaturation chamber 28-552. The amplified material is pumped from PCR chamber 28-416 by the action of fourth electrochemical pump 28-554 which is connected to channel 28-556, hence to denaturing reagent storage chamber 28-558 and through valve 28-560 and channel 28-562 to the PCR chamber 28-416. Formamide is provided in the denaturing reagent storage chamber 28-558 in combination with the size standards to be used in the capillary electrophoresis step.

These components are isolated from the PCR chamber 28-416 during the sample amplification step 204 by closed valve 28-502 and closed valve 28-420. Both valve 28-502 and 28-420 are opened and valves 28-414 and 28-506 are closed to convey the amplified material away from the PCR chamber 28-416 to the denaturation chamber 28-552. This is vented through valve 28-564, with exit channel 28-566 closed by valve 28-568.

The amplified material is held in the denaturation chamber 28-552 for the necessary time and at the necessary temperature to complete the denaturing process. Once this has been achieved, the valve 28-568 is opened and further pumping by the fourth electrochemical pump 28-554 pumps the denatured material to the electrophoresis step inlet 28-570.

At the inlet 28-570, the denatured material passes out of the plane of the cartridge 9 and through a tube to the electrophoresis cartridge section behind. The overall result of this structure is the pumping of the amplified DNA to a start point for the electrophoresis step 206.

Details of the connection of the inlet 28-570 to the CE chip are provided below.

Throughout the operations described above and in the sections that follow, various checks are made on operating conditions, component performance and successful operation so as to ensure the processing is correctly provided from start to finish. Errors or problems are indicated to the operator.

Cartridge Sequence of Operation

The sequence of operation, purely by way of example, applied to the cartridge shown in and described in relation to FIGS. 3a and b is as follows, with sample timings also given.

| Time since start (sec) | Change | Purpose and notes |
|---|---|---|
| 0.0 | Incubation chamber 358 - adjust temperature to 25° C. | |
| 0.9 | Valve 312 - opening valve - heat on | |
| 31.5 | First electrochemical pump 308 - on | |
| 73.3 | Valve 330 - closing valve - heat off | |
| 121.1 | Valve 312 - opening valve - heat off | |

-continued

| Time since start (sec) | Change | Purpose and notes |
|---|---|---|
| 138.7 | First electrochemical pump 308 - off | |
| 187.8 | Valve 326 - opening valve - heat on | |
| 212.3 | Valve 312 - opening valve - heat on | |
| 233.9 | Valve 330 - closing valve - heat off | |
| 236.0 | First electrochemical pump 308 - on | |
| 324.3 | Valve 312 - opening valve - heat off | |
| 368.6 | Valve 326 - opening valve - heat off | |
| 370.4 | Valve 346 - closing valve - heat on | |
| 401.0 | First electrochemical pump 308 - off | |
| 461.4 | Valve 346 - closing valve - heat off | |
| 653.4 | Valve 350 - opening valve - heat on | |
| 655.1 | Magnet - field applied to chamber | |
| 656.4 | Valve 326 - opening valve - heat on | |
| 684.5 | First electrochemical pump 308 - on | |
| 783.4 | Valve 326 - opening valve - heat off | |
| 804.1 | Valve 394 - closing valve - heat on | |
| 815.4 | Valve 340 - closing valve - heat on | |
| 829.6 | Valve 350 - opening valve - heat off | |
| 840.8 | Magnet - field removed from chamber | |
| 867.5 | First electrochemical pump 308 - off | |
| 894.2 | Valve 394 - closing valve - heat off | |
| 944.5 | Valve 368 - opening valve - heat on | |
| 975.5 | Valve 340 - closing valve - heat off | |
| 977.2 | Second electrochemical pump 356 - on | |
| 1025.8 | Valve 354 - closing valve - heat on | |
| 1036.2 | Valve 368 - opening valve - heat off | |
| 1050.8 | Second electrochemical pump 356 - off | |
| 1079.7 | Valve 324 - opening valve - heat on | |
| 1080.6 | Valve 368 - opening valve - heat on | |
| 1116.3 | Valve 354 - closing valve - heat off | |
| 1118.0 | Second electrochemical pump 356 - on | |
| 1181.3 | Valve 370 - closing valve - heat on | |
| 1196.4 | Valve 368 - opening valve - heat off | |
| 1228.3 | Valve 324 - opening valve - heat off | |
| 1233.9 | Second electrochemical pump 356 - off | |
| 1244.2 | Valve 398 - opening valve - heat on | |
| 1249.4 | Valve 324 - opening valve - heat on | |
| 1271.8 | Valve 370 - closing valve - heat off | |
| 1273.1 | Magnet - field applied to chamber | |
| 1284.7 | Second electrochemical pump 356 - on | |
| 1328.6 | Valve 324 - opening valve - heat off | |
| 1333.8 | Valve 402 - closing valve - heat on | |
| 1334.7 | Valve 408 - closing valve - heat on | |
| 1379.9 | Valve 398 - opening valve - heat off | |
| 1383.8 | Magnet - field removed from chamber | |
| 1393.9 | Second electrochemical pump 356 - off | |
| 1419.5 | Valve 362 - opening valve - heat on | |
| 1435.4 | Valve 402 - closing valve - heat off | |
| 1465.1 | Valve 408 - closing valve - heat off | |
| 1466.0 | Second electrochemical pump 356 - on | |
| 1474.6 | Valve 374 - closing valve - heat on | |
| 1493.6 | Valve 362 - opening valve - heat off | |
| 1501.8 | Valve 382 - opening valve - heat on | |
| 1504.8 | Valve 362 - opening valve - heat on | |
| 1508.7 | Second electrochemical pump 356 - off | |
| 1531.9 | Third electrochemical pump 388 - on | |
| 1578.8 | Incubation chamber 358 - adjust temperature to 60° C. | |
| 1585.0 | Valve 374 - closing valve - heat off | |
| 1586.6 | Valve 362 - opening valve - heat off | |
| 1588.5 | Valve 364 - closing valve - heat on | |
| 1633.3 | Valve 382 - opening valve - heat off | |
| 1640.4 | Third electrochemical pump 388 - off | |
| 1679.0 | Valve 364 - closing valve - heat off | |
| 1881.0 | Valve 412 - opening valve - heat on | |
| 1882.9 | Valve 382 - opening valve - heat on | |
| 1906.2 | Magnet - field applied to chamber | |
| 1914.9 | Third electrochemical pump 388 - on | |
| 1952.3 | Incubation chamber 358 - adjust t to 25° C. | |
| 2010.0 | Third electrochemical pump 388 - off Magnet - field removed from chamber Valve 382 - opening valve - heat off Valve 412 - opening valve - heat off | |
| 2017.3 | Valve 420 - closing valve - heat on Valve 414 - closing valve - heat on | Isolate PCR chamber |
| 2173.3 | Valve 420 - closing valve - heat off Valve 414 - closing valve - heat off | |
| 2185.0 | Incubation chamber temperature control - off | |

Cartridge Alternatives

There are a variety of alternatives for the various components within the cartridge and/or their operation. Some of these are now described, by way of example only.

1) Bead Handling

As described above, the cartridge makes use of a bead storage chamber 318 from which the beads are washed in operation. This washing action provides contact between the sample, reagents and the beads. Mixing results in the beads taking up the DNA in the sample and retaining it. Subsequent retention of the beads allows the DNA to be separated from the rest of the sample and allows washing stages to improve further this separation.

It is important to ensure that the beads are displaced from their storage location, such that the beads are available, in contact with the relevant liquids, to perform their task. Modifications to the manner in which the beads are stored and/or dispensed can assist in this. The beads may be stored away from the cartridge. They may be introduced to the cartridge to prepare it for use.

Firstly, it is possible to provide a dispersant together with the beads so as to keep them dispersed and hence more easily collected and carried by the fluid flow. This can help prevent blockages and/or agglomerations of beads. Different dispersants and/or variations in the amount provided can be used to tailor this.

Figure 6A:
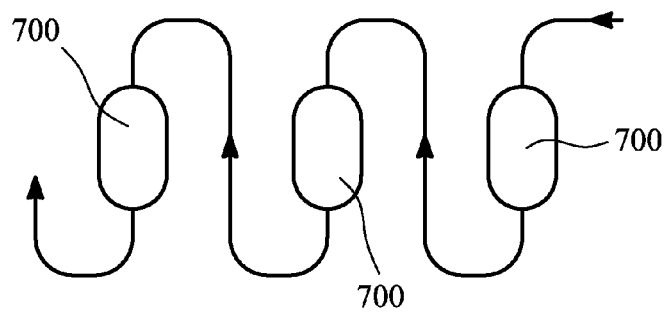
FIGS. 6a to 6e are schematic illustrations of alternative arrangements for contacting the fluid and beads.
Figure 6B:
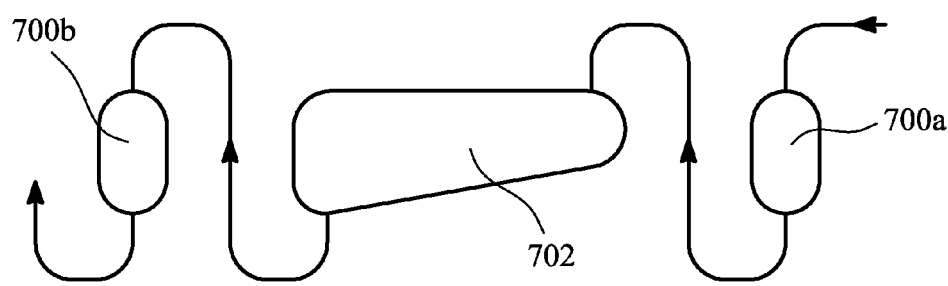
Figure 6C:
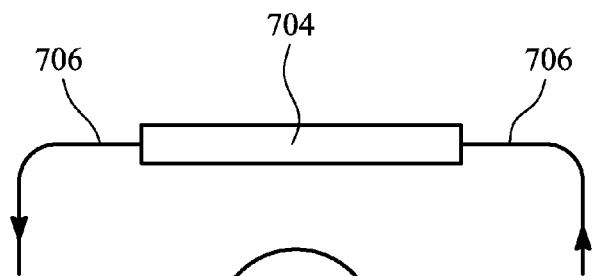

Secondly, it is possible to provide the beads in a series of bead storage chambers, rather than in a single chamber. FIG. 6a illustrates one such arrangement, where the beads are split into three groups, each in its own chamber 700. In this way, the contact between the fluid and the beads is staggered and a compacted mass of beads is avoided on the lead edge of the fluid. A variation on this is provided in FIG. 6b, where a first bead storage chamber 700a is separated from the second bead storage chamber 700b by a mixing chamber 702.

Thirdly, the contact can be provided with a thin chamber 704 whereby the transition of the fluid from the thing channel 706 into the chamber causes non-laminar flow and hence improved mixing. The provision of the beads spread along the length of the chamber 704 also means that they do not contact the fluid all at the same time.

Figure 6D:
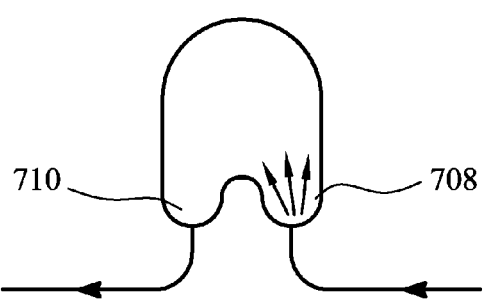
Figure 6E:
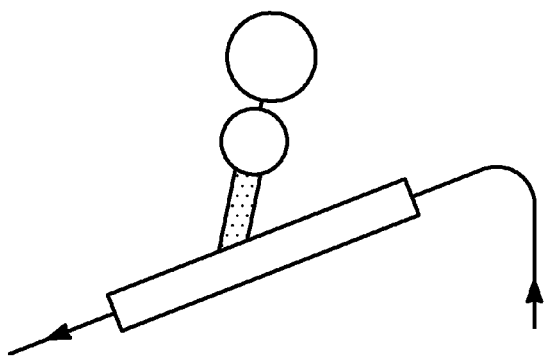
Figure 9:
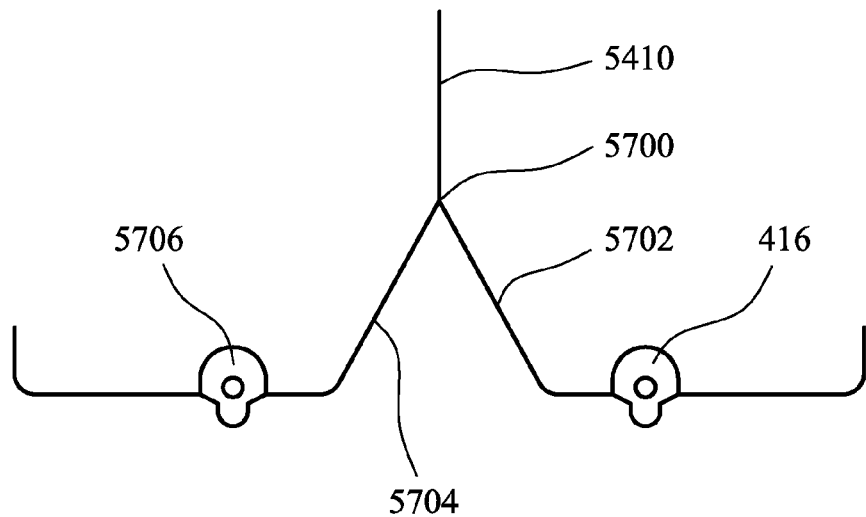
FIG. 9 is a schematic illustration of the parallel PCR chamber arrangement used in providing real time PCR and feedback of the results.

Fourthly, the flow direction and/or chamber design can be modified to encourage displacement of the beads from their storage position into a mixed form with the fluid. Thus in the FIG. 6d form, the fluid enters the chamber 700 in one bottom corner 708 and displaces, arrows, the beads resting in that part. A swirling flow within the chamber 700 gives mixing, before the fluid and bead mixture exits the chamber 700 through the other bottom corner 710.

Fifthly, the beads can be stored in a side arm 712 or other form of passage. As the flow of fluid passes through thin chamber 714 and past the junction 716 with the arm 712, a force is applied behind the mass of stored beads in the side arm 712. This forces the mass of stored beads towards and into the junction 716 where they gradually contact and are swept away by the fluid flow. Gradual dispersal of the beads into the fluid is provided. The motive force behind the beads can be provided by a similar structure to that used to move material in the context of the closing valves described herein.

2) PCR Chamber Filling

In the above system, the amount of the processed sample which is made available to the PCR stage is controlled by the relative height of the outlet from the PCR chamber to the archive chamber leading to overflow of excess sample into the archive chamber. This results in a PCR chamber which is not completely full of sample during PCR. As PCR involves heating of the sample, evaporation and/or condensation of part of the sample may occur at a location outside of the PCR chamber. This can reduce the reagents present in the PCR chamber and hence reduce the efficiency of the PCR stage.

In an alternative form, the PCR chamber is entirely filled with the sample before PCR is started. This is achieved using the arrangement of FIG. 7 where the majority of the components have the same structure and function as shown in the FIG. 3 and FIG. 4 description. The differences are in the section around the PCR chamber 416.

In this alternate form, the PCR chamber 1416 is fed material along channel 1413. Initially, the path of least resistance to this fluid flow is through the PCR chamber 1416, along channel 1500, past opened valve 1502 and onto vent 1504. The vent 1504 is hydrophobic and so allows the passage of the air displaced from the PCR chamber 1416 and channel 1500 by the material's advance. Once the fluid reaches the vent 1504, however, the path of least resistance changes and further flow occurs along channel 1418 past valve 1428 and into archive chamber 1422, which is provided with vent 1424. By this time, the PCR chamber 1416 is completely full of liquid and hence the volume of the liquid subjected to PCR is guaranteed.

As before, the valves around the PCR chamber 1416 are closed during the amplification itself, so as to isolate the PCR chamber 1416.

Figure 22:
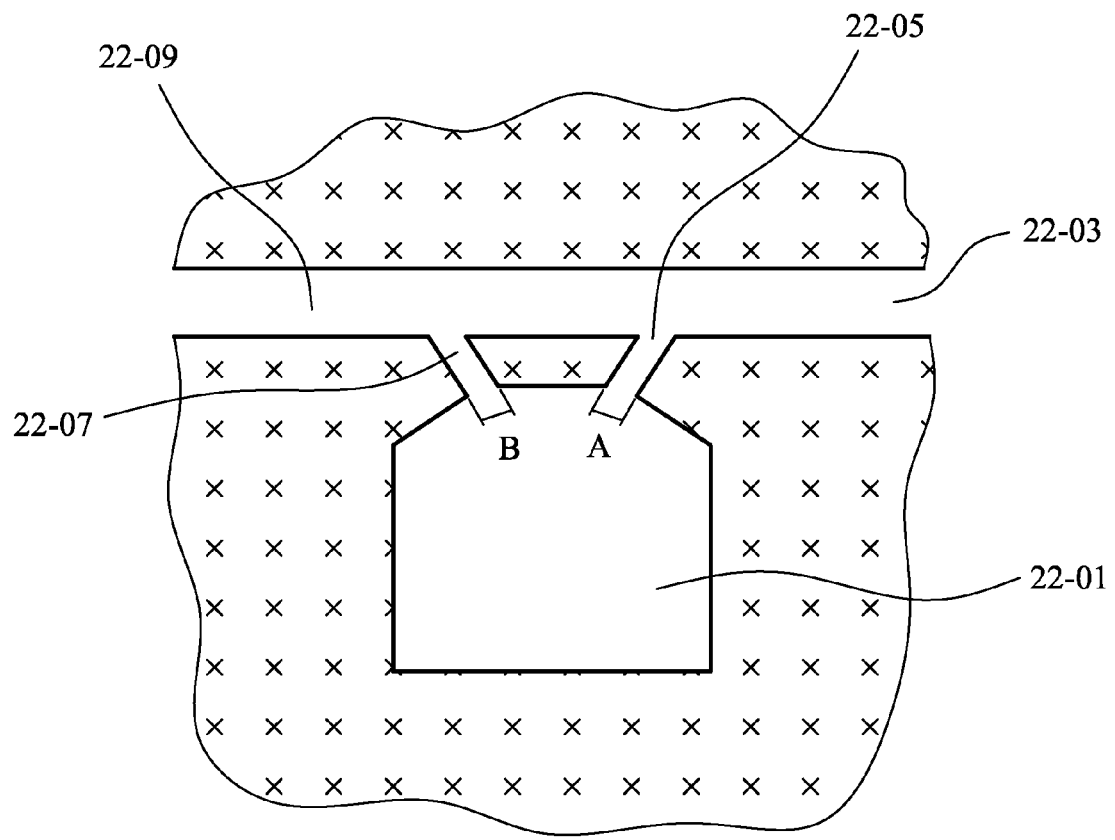
FIG. 22 is an illustration of a PCR chamber according to a further embodiment.

In a third alternative, the configuration shown in FIG. 22, the PCR chamber 22-01 is along channel 22-03. Initially, the path of least resistance to this fluid flow is through the inlet 22-05 to the PCR chamber 22-01. Once the PCR chamber 22-01 has filled, the liquid overflows through exit 22-07 into channel 22-09 which is a continuation of channel 22-03. Further fluid flow simply by-passes the PCR chamber 22-01 and flows through channel 22-03 and then channel 22-09. To control the flow correctly, the dimension A of the inlet 22-05 is greater than the dimension B of the outlet 22-07. The dimension is preferably greater in terms of the cross-sectional area, perpendicular to the direction of flow. The complete filling of the PCR chamber 22-01 ensure the volume of the liquid subjected to PCR is guaranteed.

Figure 26:
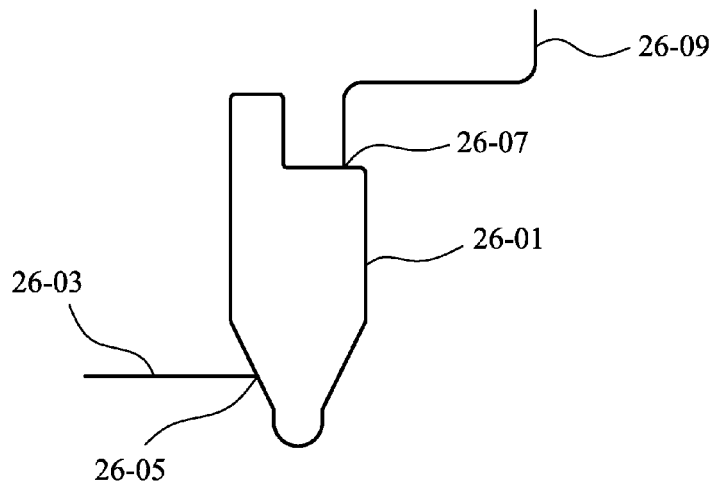
FIG. 26 is an illustration of a further embodiment of a PCR chamber.

Various shapes are possible for the PCR chamber. FIG. 26 provides an example in which the PCR chamber 26-01 is formed as smooth as possible. This assists with full fluid contact with the surfaces and hence complete and accurate filling of the PCR chamber 26-01. The sample flows along channel 26-03 and enters the PCR chamber 26-01 via inlet 26-05 provided towards the bottom of the PCR chamber 26-01. The sample fills the PCR chamber 26-01 before overflowing through outlet 26-07 provided towards the top of the PCR chamber 26-01 and into channel 26-09.

Figure 46:
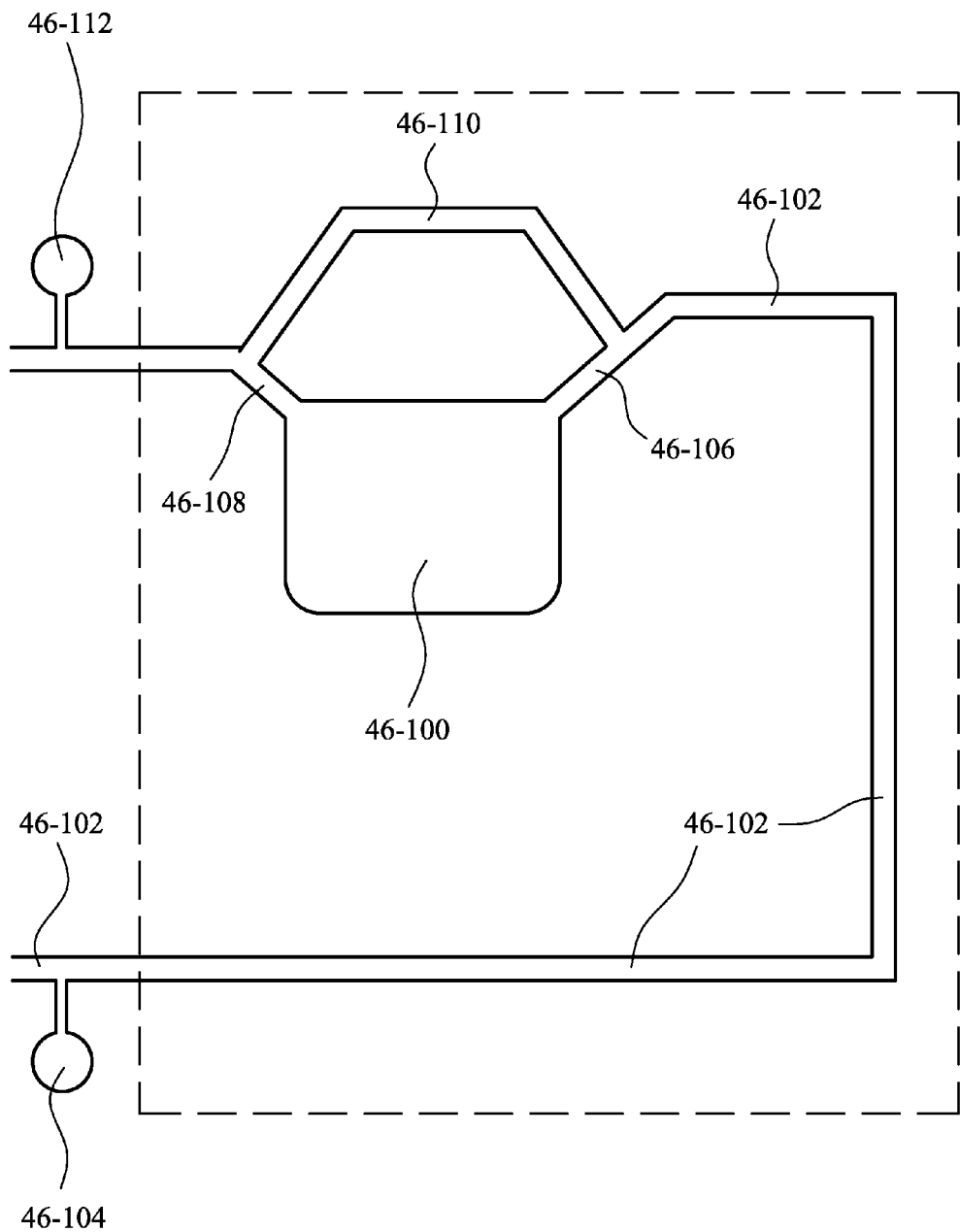
FIG. 46 shows a further embodiment of a PCR chamber.

In the embodiment of FIG. 46, a variation on the above principle is provided. The flow to the PCR chamber 46-100 passes along channel 46-102 and past valve 46-104. The channel 46-102 turns as it approaches the chamber 46-100 and provides inlet channel 46-106. The natural flow is along this route. As the flow progresses, the PCR chamber 46-100 fills, with the gas exiting through outlet channel 46-108. The outlet channel 46-108 has a similar configuration to inlet channel 46-106, but the cross-sectional area of the outlet channel 46-108 is much smaller than that of the inlet channel 46-106. As a result, when the liquid reaches the outlet channel 46-108, the flow resistance increases greatly and flow is redirected along the by-pass channel 46-110 in preference. Both the outlet channel 46-108 and the by-pass channel 46-110 lead past valve 46-112 to exit channel 46-114. The Peltier effect device heats the area within the dotted lines and so ensures that as much of the space between the two valves, 46-104 and 46-112 is heated so as to minimise any condensation within that space.

3) Sample Concentration Before Capillary Electrophoresis

In some instances, it may be helpful to increase the concentration of the sample prior to its use in the electrophoresis step and/or to reduce the size of the sample as it is injected.

Once suitable approach for doing so is set out in European patent publication no 1514100, the contents of which are incorporated herein by reference. This technique uses careful balancing of the electrophoretic velocity of the DNA and the opposing electroosmotic velocity to concentrate the DNA at the liquid to gel interface. A change in conditions can then be used to drawn the concentrated DNA into the electrophoresis step as a concentrated and small sample.

Another option is hydrodynamic stacking. This is based upon the variation in the flow velocity between sample and the location from which the size based separation starts, for instance through the use of adjustments to conductivity, buffer components, pH and the like. An example of such an approach is field amplified sample stacking, FASS. This provides higher electric fields in the lower conductivity zones than in the higher conductivity zones. The sudden potential drop at the interface between the two zones causes sample stacking there.

Mechanical pre-concentration is also a possibility. Packed beds, nanochannels, immobilised polymers and membranes all offer the possibility of trapping and concentrating the sample. Electro-elution, where by the release of the sample is caused by the application of an electric potential to a membrane, is one possibility.

A combined technique approach to pre-concentration may be particularly beneficial. Such an approach is shown in FIG. 24, in the case of CE channel being in the same plane as the rest of the cartridge, and FIG. 25, in the case of the CE channel not being in the same plane as the rest of the cartridge.

As illustrated, the combined flow 24-01, 25-01 of DNA containing sample and formamide pass valve 24-03, 25-03 and then reach a junction 24-05, 25-05. The Y-shaped junction brings the combined flow 24-01, 25-01 into proximity with the running buffer flow 24-07, 25-07 in channel 24-08, 25-08. These flows cross the CE channel 24-09, 25-09 and any excess passes to chamber 24-11, 25-11. The left-hand detail shows the construction present at the intersection of the CE channel 24-09, 25-09 and the channel 24-08, 25-08.

Figure 24:
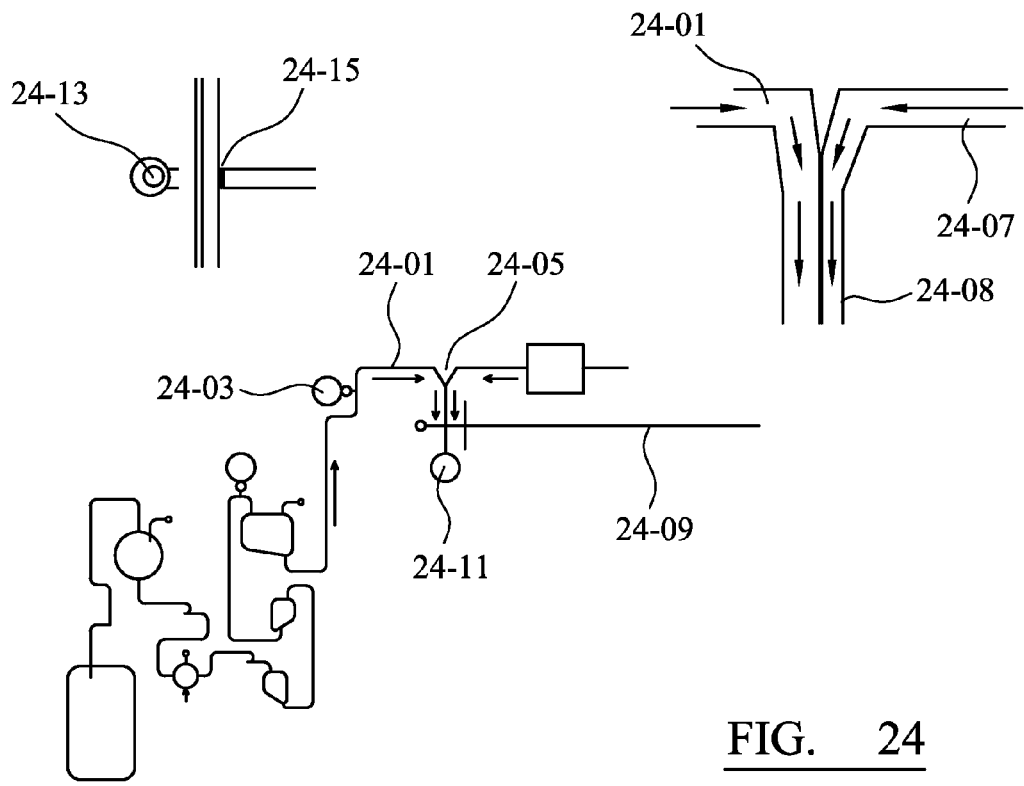
FIG. 24 is an illustration of an embodiment for loading a CE channel

In the FIG. 24 form, the stacking interface 24-11 is provided between the combined flow 24-01 and buffer flow 24-07. The electric potential is provided by electrode 24-13. The second stacking function is provided by the membrane 24-15 provided between the buffer flow 24-07 and the CE channel 24-09.

Figure 25:
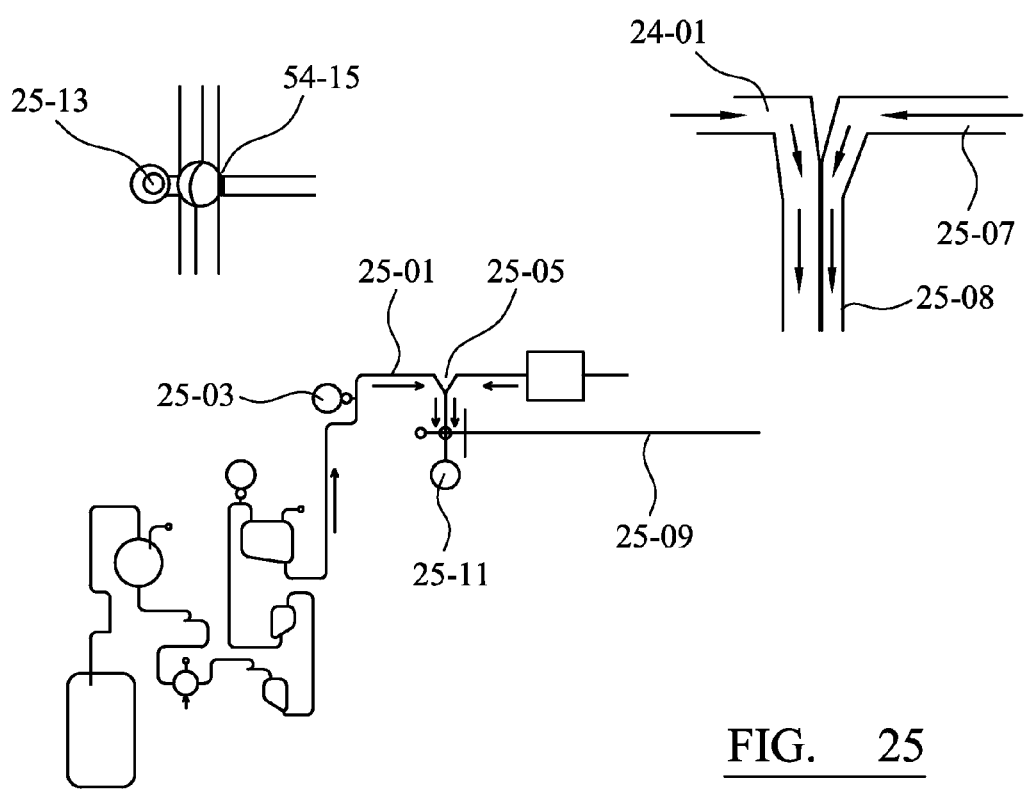
FIG. 25 is an illustration of a further embodiment for loading a CE channel.

In the FIG. 25 form, the stacking interface is similarly provided.

4) Alternative Electrophoresis Channel Configuration

In the embodiment described above, the injector is of the double T type. As an alternative, it is possible to use a cross-channel injector, as shown in FIG. 8.

In this case, the reservoir 604, channel 610 and other parts leading to the fourth electrode location 620 are the same. The arm 624 provided with the fourth electrode location 620 and the arm 622 provided with the third electrode location 618 are aligned on a common axis and at 90° to the main capillary 616.

The sample is drawn towards the electrode at the third electrode position 618 by the application of a voltage. To prevent dispersion of the sample into the main capillary, towards the first 612 and/or second 614 electrode locations, a voltage is applied to the electrode at the first electrode location 612 and to the electrode at the second electrode location 614. This has the effect of pinching the part of the sample at the intersection of the main capillary 616 and the arms 622, 624, and maintaining the minimal size of the plug which is then used in the capillary electrophoresis.

Figure 43:
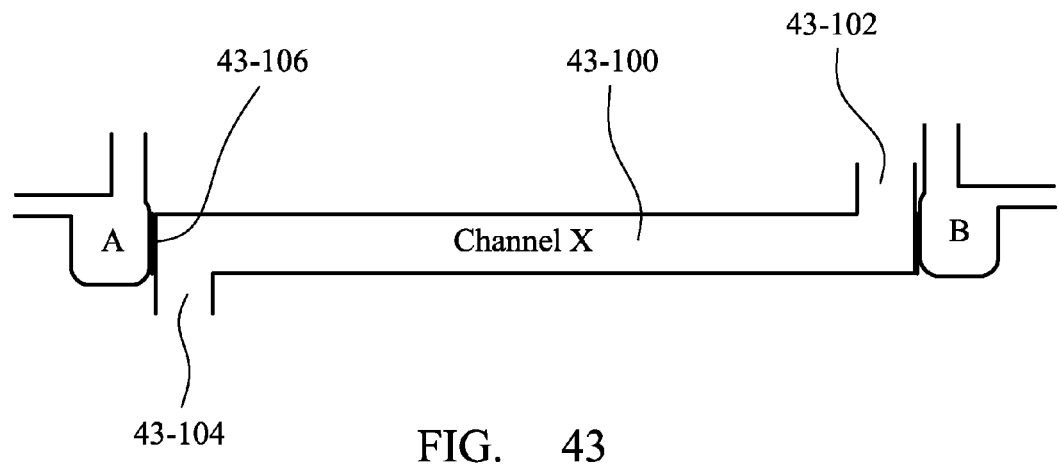
FIG. 43 shows an approach to loading sample to the CE step.

A further electrophoresis channel configuration is shown in FIG. 43. In this case, the sample flows along channel 43-100 from inlet 43-102 to outlet 43-104. A potential difference is applied between locations A and B. This draws the DNA in the sample towards the membrane 43-106. The membrane is sized, 10-14 kDa cutoff, to retain the DNA. The separation matrix is then flowed into the channel 43-100; UV activation may be provided, as discussed elsewhere. The same buffers at location A, B and in the matrix are then provided for the electrophoretic separation to be provided through the application of a potential difference between A and B.

The polarity may be provided in the reverse direction before the CE run, for instance to ensure the buffer extends from A to B. DNA is not lost as the flow will maintain it on the membrane 43-106.

Between loading to the membrane 43-106 and the CE separation, it is possible to introduce a variety of reagents/buffers into locations A and/or B and/or the channel 43-100 to assist in purifying the DNA and/or to optimise CE conditions, for instance through removal of excess salts and/or unincorporated PCR primers. Both locations A and B have their own inlets and outlets for this purpose.

Figure 44:
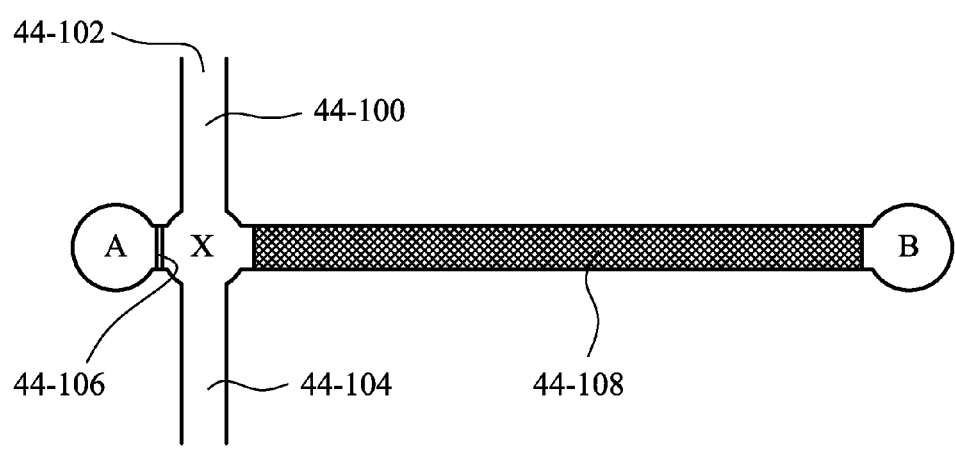
FIG. 44 shows an alternate approach to loading sample to the CE step.

A still further configuration is shown in FIG. 44. In this case, again the sample flows through channel 44-100 from inlet 44-102 to outlet 44-104. A potential difference between A and B is used to attract and retain the DNA on a membrane 44-106. By swapping to an electrolyte flow through channel 44-100 and changing the potential difference it is possible to load the DNA to the matrix in main channel 44-108. The CE can then be performed.

Again one or more cleaning or condition controlling steps may be provided before CE is conducted.

Figure 45:
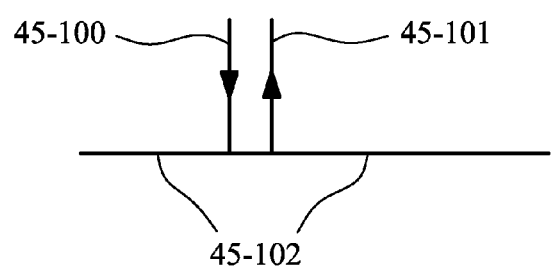
FIG. 45 shows a further alternative for loading sample to the CE step

A yet further configuration is shown in FIG. 45. In this case, the arm 45-100 leading the sample into the main channel 45-102 where CE is performed extends downwards, at least partially aligned with gravity. The arm 45-104 leading away from the main channel 45-102 extends upward, at least partially aligned with gravity. In this way gravitation effects promote retention within the main channel 45-102, rather than encouraging flow away from it and into another arm.

5) Cartridge Variant for Real Time PCR Performance

In the cartridge 9 described above, the cartridge 9 is being used to consider a reference sample. In this alternative embodiment, the changes to the cartridge 5009 beneficial to the consideration of a casework sample are considered.

A major difference between a casework sample and a reference sample is that whilst the amount of DNA recovered in a reference sample has a degree of consistency, and is of a high level, this is not the case for a casework sample. The manner in which the sample is left, the passage of time, the collection process and other factors can all result in the amount of DNA in a casework sample being unpredictable, and often lower, than desired.

To counteract this, the casework sample processing seeks to ensure that the amount of DNA arising from the amplification process is within certain bounds.

To do this, the casework sample provides for parallel processing of the sample, particularly in terms of the sample amplification step 204.

The sample receiving step 200 and sample preparation step 202 are basically the same as previously described. The difference comes in the sample amplification step 206.

The channel 5410 containing the eluted DNA from the beads held in the incubation chamber 5358 leads to a junction 5700 where the flow is split into two separate streams 5702, 5704.

The first stream 5702 passes into a PCR chamber 416 of the type previously described (and is not illustrated further). The subsequent handling of this by the cartridge 9 is as described above, save for the possible changes in the sample amplification conditions/duration described shortly.

The second stream 5704 passes into a second separate PCR chamber 5706. This second PCR chamber 5706 contains a bead provided with a coating containing the necessary regents for PCR and for a quantification analysis.

During processing, PCR is advanced in the PCR chamber 416 and in the second PCR chamber 5706, in parallel. After a given number of PCR cycles for the second PCR chamber 5706, the contents of the second PCR chamber 5706 are considered to establish the quantity of DNA which has been generated by the PCR cycles up to that point. This can be equated to the amount of DNA present within the original sample and hence the amount of DNA the PCR chamber 416 is working on. As a result of the quantification, the PCR conditions and/or cycle number for the PCR chamber 416 can be varied to optimise the quality of amplification product.

Further details on the operation of such a system and the use of this feed back are to be found in 61/026,869, the contents of which are incorporated herein by reference, particularly as they relate to the parallel conduct of PCR and the use of the results from one PCR to control and/or modify the conduct of the other PCR.

Suitable reagents include the Plexor HY kit available from Promega Inc, 2800 Woods Hollow Road, Madson, Wis. 53711, USA and Quantifiler® Duo DNA quantification kit available from Applied Biosystems, Foster City, Calif., 944404, USA.

To establish the quantity of DNA present, it is necessary to interrogate the sample using an excitation light source and then quantify the amount of light arising. To do this, light from a light source is conveyed to the second PCR chamber 5706 and focussed thereon using a lens system. The excitation light interacts with the dye(s) associated with the sample. The fluorescent light generated is detected and is proportional to the quantity of DNA present.

The light source used could be the same light source as is used for the electrophoresis step 206, and described in detail below. The light would be conveyed to the second PCR chamber 5706 by an optical fibre. Because the Peltier heater/coolers are positioned in front of and behind the second PCR chamber 5706, the light for the detection is introduced from the side of the cartridge 9. The light source may be a laser, for instance of the type and/or with the set up discussed further below in the electrophoresis step 206. As an alternative, however, it is possible to use a light emitting diode based light source, as described below.

Depending upon the quantity, the number of cycles used in the PCR chamber 416 may be increased, decreased or kept at the normal level, so as to provide a quantity of DNA within the desired range after PCR has been completed in PCR chamber 416.

In the context of real time quantification and/or the handling of samples from crime scenes (rather than those taken under controlled conditions from individuals), differences in the implementation of the invention may be provided. These may include:

1) The parallel processing of the sample so as to allow the results from a first processing of the sample to inform on the optimum conditions etc to be used in the main processing of the sample. Further details of such an approach are to be found in WO2009/098485, the contents of which are incorporated herein by reference with respect to the parallel processing and consideration of samples and the feedback of information from one processing to the other.

2) The efficiency of the extraction should be as high as possible, for instance through optimised sample recovery, lysis and amplification. The use of various processes and/or reagents to separate the DNA of interest from problematic components, such as PCR inhibitors, is beneficial in this respect.

3) The cartridge used will feature many of the steps and components exemplified above, but with the incorporation of the parallel PCR circuit and the ability to analyse the results therefrom, for instance using a laser or LED to apply light to the liquid, with the return light being detected to inform on the PCR process. Photo diodes and/or cameras can be used in the light detection. A control material may be provided within the sample to provide a reference value with respect to the light detected.

4) The instrument would benefit from being able to run positive and/or negative controls. These could be run in the same cartridge as the sample. The controls may be handled by the operator in the same manner as the sample of interest so as to inform on contamination risks. The controls may just be run periodically so as to check on the instrument, for instance in the form of a calibration check.

Cartridge Components

Within the cartridge are a significant number of components, with each being optimised with respect to its role and its role in combination with the other components.

1) Valves

Figure 10A:
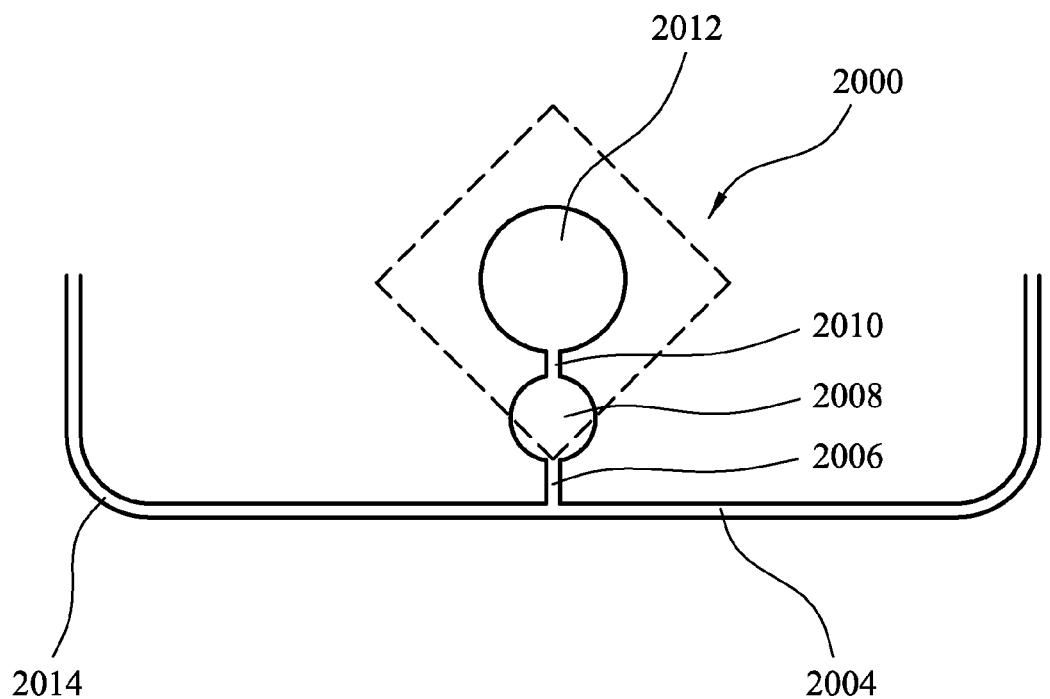
FIG. 10a is an illustration of a closing valve used in the present invention.
Figure 10B:
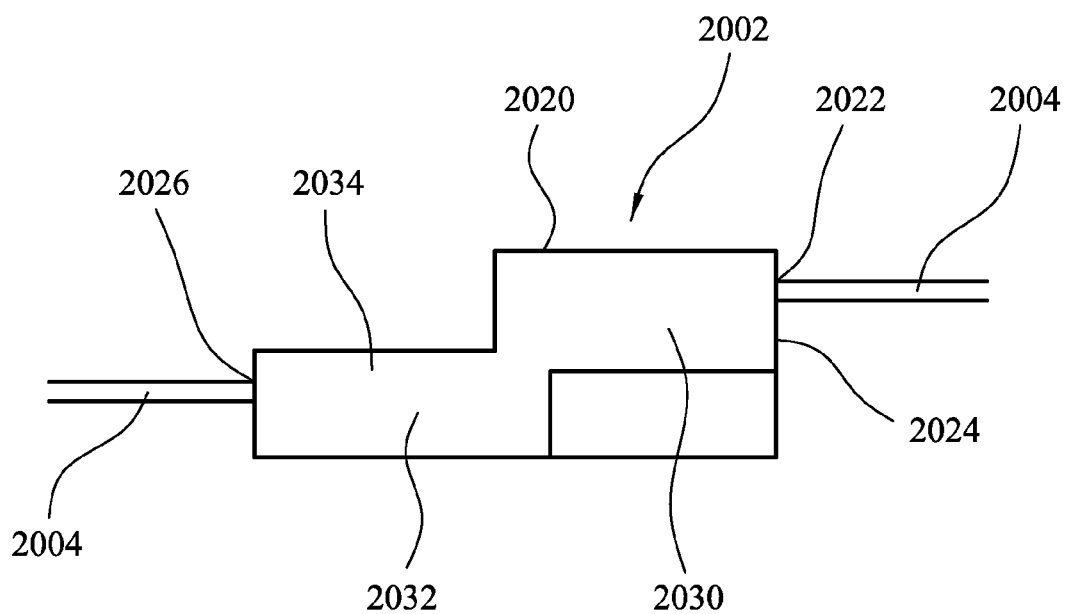
FIG. 10b is an illustration of an opening valve used in the present invention.

To minimise manufacturing costs and give consistent operation, all of the valves in the cartridge are one of two types. The two types are a closing valve 2000; FIG. 10*a*; and an opening valve 2002; FIG. 10*b*.

The closing valve 2000 is shown schematically in FIG. 10*a*. The closing valve 2000 is positioned above, relative to the direction of gravity, the channel 2004 to be closed. The closing valve 2000 is formed by a conduit 2006 which is in fluid communication with the channel 2004 and is in fluid communication with the bottom of a valve reservoir 2008. The valve reservoir 2008 is filled with paraffin wax and is 3 mm in diameter and is provided with the conduit 2006. On the top of the valve reservoir 2008, a gas passage 2010 provides fluid communication with a valve gas reservoir 2012. The valve gas reservoir 2012 is full of air.

The dotted line in FIG. 10*a* shows that part of the location of the closing valve 2000 which is in contact with a heater element, not shown, provided on the adjoining printed circuit board of the instrument.

When the closing valve 2000 is to be activated, the heater element is caused to heat up. This both melts the paraffin wax in the valve reservoir 2008 and causes the air in the valve gas reservoir 2012 to expand. The expansion of the air provides the driving force to displace the melted paraffin wax from the valve reservoir 2008 into the conduit 2006 and then into the channel 2004.

The volume of paraffin wax displaced is controlled by the temperature to which the valve gas reservoir 2012 is heated (variation in pressure) and the duration of the heating applied (as the paraffin wax soon solidified once the heating is switched off).

Continued displacement of the paraffin wax into the channel 2004 causes the paraffin wax to expand in each direction along the channel 2004.

In some cases, the fluid in the channel will not compress or move in one direction (or is limited in the extent possible) and so the flow of the paraffin wax within the channel 2004 occurs preferentially in the other direction. Normally, the paraffin wax is displaced into the channel 2004 until a 2 mm to 10 mm length of the channel 2004 is filled. With the heat removed, the paraffin wax sets in this new position and the channel 2004 is reliably sealed.

The section where the channel 2004 is to be shut, is deliberately chosen to be horizontal, relative to the direction of gravity, as this assists the retention of the paraffin wax at the location to be sealed.

To assist further in the formation of the seal, it is beneficial to arrange the closing valve so that it is between one or two upward, relative to the direction of gravity, bends. As shown in FIG. 10*a* the bend 2014 provides assistance in the accurate formation of the seal within the channel 2004.

The opening valve 2002 is shown schematically in FIG. 10*b*. The opening valve 2002 is positioned as a part of the channel 2004 the fluid flows through. The opening valve 2004 is formed by a valve chamber 2020 which has an inlet 2022 from the channel 2004 in a first side wall 2024 and an outlet 2026 leading to the continuation of the channel 2004 in the opposing side wall 2028.

The paraffin wax is positioned in the initial section 2030 of the valve chamber 2020. Downstream of this initial section 2030, is a trap section 2032. The dotted line in FIG. 10*b* shows that part of the opening valve 2002 which is in contact with a heater element, not shown, provided on the adjoining printed circuit board of the instrument.

When the opening valve 2002 is to be activated, the heater element is caused to heat up. This melts the paraffin wax in the initial section 2030. By the time the paraffin is melted, or shortly thereafter, an electrochemical pump upstream of the opening valve 2002 has been activated for sufficient time to cause a pressure build up, upstream of the opening valve 2002. This pressure causes the driving force to displace the melted paraffin wax from the initial section 2030 and downstream into the trap section 2032. Once in the trap section 2032, the passage 2034 above the paraffin wax is clear allowing fluid communication through the opening valve.

With the heat removed, the paraffin wax sets in this new position and the channel 2004 and passageway 2034 is reliably opened.

The section where the channel 2004 is to be opened is deliberately chosen to be horizontal, relative to the direction of gravity, as this assists the retention of the paraffin wax in the trap section 2032.

In some applications, particularly those close to the high temperatures used in the PCR chamber, the valves benefit from using a high melting point wax. This melts at greater than 95° C. and so does not melt under PCR conditions. In some cases, the valve performance can be improved further by using a high melting point and lower melting point mixture; with the lower melting point wax tending to fill any cracks which form in the higher melting point wax.

A further valve embodiment is shown in FIG. 47. The channel 47-100 is connected to the valve by a side channel 47-102 as usual. The side channel 47-102 leads to a first chamber 47-104. This is connected via a short channel 47-106 to a larger second chamber 47-108.

2) Chambers

Within the cartridge, a variety of chambers are provided for a variety of purposes. To achieve those purposes efficiently and effectively, the chamber designs are optimised in various ways.

With respect to the incubation chamber 358, this is provided with a broad base which is generally horizontal. In operation, the offset magnet (not shown) is used to restrain the magnetic beads in position during washing and during elution. The broad base provides a suitable location to which the beads can be drawn and secured, whilst exposing them to the wash flow or to the elution flow.

The sloping walls within the incubation chamber 358 and the bubble mixing chamber 342 are provided to promote the flow of eluent, introduced into the chambers at the top, to the outlet at the bottom of the chamber.

The angular corners are used to generate improved pressure gradients from the inlet for a part of the process to the outlet in that respective part of the process.

The first further mixing chamber 332 and second further mixing chamber 336 are provided to encourage non-laminar flow within the flow route. As the fluid transitions from the channel, with its cross-section, to the chambers, with their increased cross-section, non-laminar flow arises. This gives good mixing for the different density fluids and particles which are all to be mixed. Such mixing forms are significantly better in this respect than bubble mixing alone or piezoelectric based mixing.

The PCR chamber 416 has two principle embodiments; as described above. In each, the PCR regents are provided within the degradable shell of a bead located within the PCR chamber 416. To ensure proper flow of the liquids around and past the bead, the bead is provided with a bead seat. This provides a defined rest position for the bead, but as the bead is only contacted at discrete locations when in the seat, fluid is still able to flow past the bead. The seat ensures that the bead does not block at inlet to and/or outlet from the PCR chamber 416. The seat ensures that there are no large areas of the bead surface, and hence of the reagents, which are isolated for fluid contact.

In the second of the PCR chamber 416 embodiments, described in the alternatives for the cartridge section, the PCR chamber 416 is completely filled with fluid. This gives a reproducible volume of fluid in the PCR process. The same position arises with the third embodiment, FIG. 22.

In the first of the PCR chamber 416 embodiments, the maximum level of fluid within the PCR chamber 416 is controlled by the relative height of the outlet within the chamber. The outlet in effect acts as an overflow for the fluid, once the PCR chamber 416 has filled to this level. A head space remains above the fluid, within the PCR chamber 416.

3) Vents

To allow fluid flow, air or sample, around the cartridge 9, various vents need to be provided for various chambers.

To prevent any risk or suggestion that material can enter the cartridge 9 through such vents, each of the vents is provided with a filter element to exclude particulate material. In addition, when a vent is part of the active processing on the cartridge 9, the vent is under positive pressure and so air is flowing out through the vent. This too assists in preventing any risk of particulate material entering the cartridge 9.

In some situations, it is desirable to be able to allow air to pass through the vent freely, but for the vent to resist the passage of any subsequent liquid. An example is to be found in the alternative PCR chamber 416 filling embodiment. To provide this, those vents are hydrophobic. The vent may be hydrophobic because of the base material forming the vent and/or because of a treatment applied to the material of the vent. Such a treatment can be provided, for instance, by using polypropylene material and/or by providing a polysulphone coating.

4) Archive

As described above, the fluid not needed in the PCR chamber 416, is pumped onward to an archive chamber 422.

The purpose of the archive chamber 422 is to provide a storable record of the sample supplied to the sample amplification stage 204, and the PCR chamber 416 in particular.

If needed, the sample in the archive chamber 422 can be accessed at a later date to enable a further amplification and analysis to be performed. Further processing in this way is useful where it is necessary to repeat the analysis, for instance by way of verification. Alternatively, further processing enables a different amplification and analysis protocol to be applied, for instance, a protocol suitable for low levels of DNA within the sample.

In the form shown in FIG. 3, the archive chamber 422 is an integral part of the overall cartridge 9.

Figure 11:
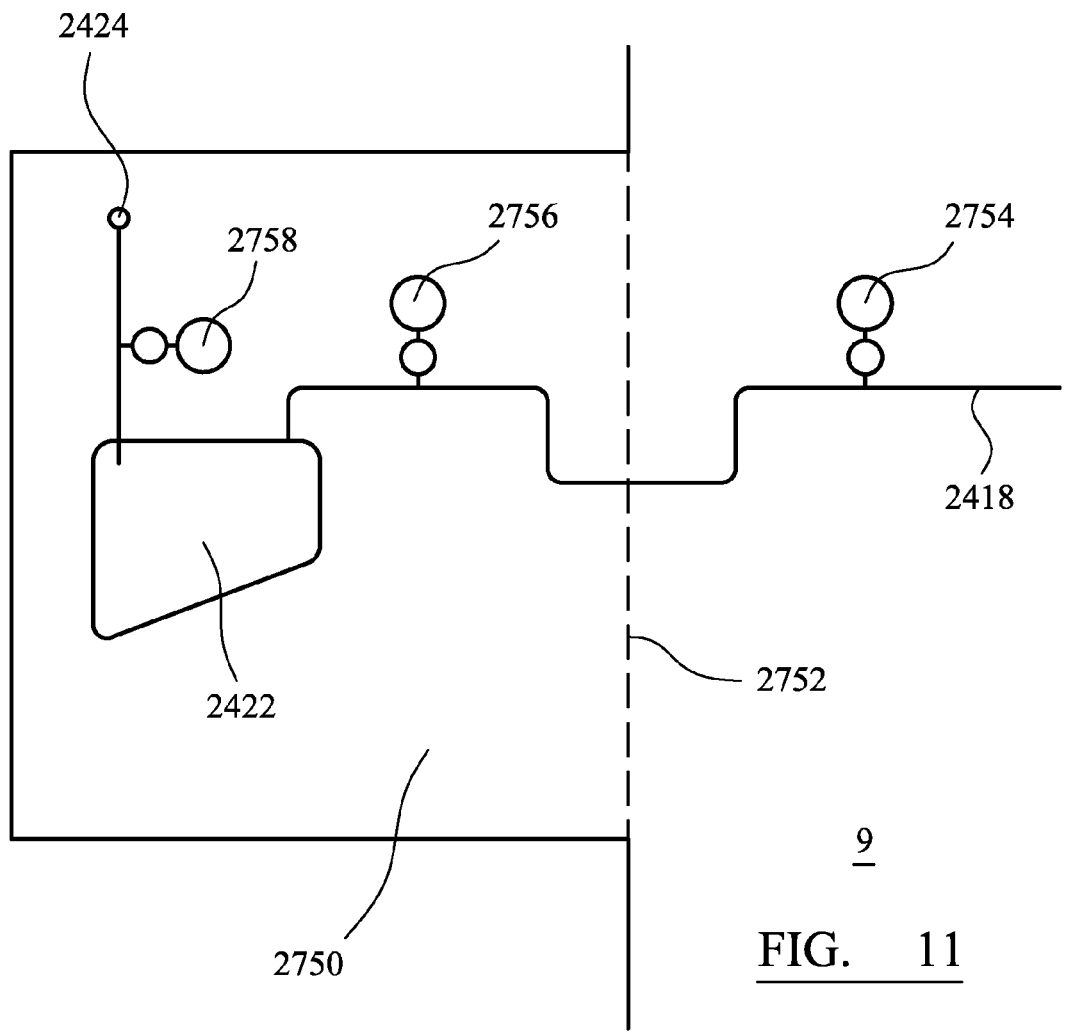
FIG. 11 shows an option for the archiving of a part of the sample handled.

In an alternative, form shown in FIG. 11, the archive chamber 2422 is still fed the surplus sample through a channel 2418 leading away from the PCR chamber, not shown.

The archive chamber 2422 is positioned on a stub 2750 which extends from the side of the cartridge 9. The stub 2750 is connected to the cartridge 9 during normal use, but a line of weakness 2752 is provided. This allows the stub to be snapped off the cartridge 9 after the completion of the processing. This means the archive function can be provided by only storing the stub 2750, rather than have to store the far larger overall cartridge 9. Given the number of samples which may be considered, and the time for which they have to be stored, saving of storage space is a significant issue.

To seal the archive chamber 2422, once it has been loaded, a closing valve 2754 is provided on the cartridge 9 side of the line of weakness 2752 and a further closing valve 2756 is provided on the stub 2750 side of the line of weakness 2752. These valves are activated to place paraffin wax in the channel 2418 on either side of the line of weakness 2752. To provide for long term storage, a further closing valve 2758 is provided on the channel leading from the archive chamber 2422 to the vent 2424.

Just as the cartridge 9 is provided with an identifier, which is used to link it in the records to the sample loaded upon it, then the stub 2750 is also provided with a common identifier so as to maintain the link after the stub 2750 is broken off the cartridge 9.

5) Reagents

Various options exist for the provision of the reagents needed in the various steps of the processing. As far as possible, so as to keep the processing as simple as possible for the user, the cartridge 9 is provided with pre-loaded reagents. Examples of such pre-loaded reagents would include the bead provided in the PCR chamber 416; with the bead carrying the PCR regents inside. Other pre-loaded regents include the various wash liquids and elution liquids described in the methodology above.

If necessary, one or more reagents can be provided separate from the cartridge 9, and be loaded onto the cartridge at or close to the time of use. This may be necessary where the reagent is unable to withstand prolonged storage under the conditions to which the cartridge 9 is exposed. These may be conditions of temperature and/or mechanical conditions such as vibration or orientation.

A preferred form of reagent provision is provided where the reagent(s) are provided as part of a solid phase reagent or solid phase reagent storage component, with release of the reagent being triggered by an increased temperature. Gel forms of reagent and/or reagent storage component, preferably triggered to release by the application of higher temperatures are also a useful option.

6) Electrochemical Pumps

To simplify the construction and costs of the cartridge, a common approach is used to providing the motive power to the various operations on the cartridge; electrochemical pumps. Each of the electrochemical pumps consists of a pair of electrodes immersed in the electrolyte. The flow of a current results in off gassing. The off gas collects in the top of the electrochemical pump, increases in pressure and leaves the pump via the outlet in the top of the pump. This off gas pushes ahead of itself other fluids encountered in the channels and chambers. The off gas contributes to bubble mixing in some of the stages.

To give a desired extent of pumping, the volume of the electrochemical pump can be varied. The extent of pumping can be delivered in one, two or more goes, as turning off the current stops the pumping action.

The rate of pumping and/or pressure delivered can be varied by varying the molarity of the electrolyte. Sodium chloride is the preferred electrolyte; used at 1M; and used in conjunction with aluminium electrodes.

7) Electrophoresis Matrix

The material provided within the capillary of the electrophoresis stage is important to the reliability and resolution of the analysis obtained.

Various possible materials can be used in the capillary. These include the use of polymer matrix, for instance a polyhydroacrylamide, a polydimethylacrylamide or mixtures there of. The polymers may be cross-linked to give the desired properties and/or formed into their state of use within the capillary, after loading. It is also possible to use an inert bed of particulate material to form the matrix in which the size based separation is achieved.

As well as optimising the performance through the properties of the gel, it is also possible to treat the capillary walls to improve properties. For instance it is possible to apply hydrophilic coatings, such as poly(hydroxyethlacrylamide).

A potential methodology for the electrophoresis matrix is to store that material in a chamber which is a part of the CE chip, but not use that chamber for the CE separation. Instead, when required for use, the stored matrix is moved from the chamber into the capillary so as to fill it to the desired degree. As a result of loading just before use, the matrix is no subject to sedimentation effects; these can have a detrimental effect on the analysis. Pressure loading can be used for this purpose.

Another potential methodology is to fill the main channel and arms of the CE chip with the matrix. Those parts of the CE chip where the matrix is not needed, for instance aside from the main channel, may be masked. In this way, when UV light is applied the parts where the matrix is not needed retain the matrix unaltered. The unaltered matrix can be washed away. Where the matrix is exposed to UV light it is altered and resists washing away.

8) CE Chip Design

A preferred configuration for the CE chip is shown in FIG. 42a and the detailed partial view of FIG. 42b.

The end portions 42-100 cooperate with the carrier when the chip is mounted within it. The external profile of the base of the CE chip is designed to match with that defined by the raised surface around the CE chip heater board, described elsewhere in this document.

As described below, a number of electrodes are required in different parts of the channels provided within the CE chip so as to load the sample and then perform the necessary separation to give the analysis. These electrodes within the channels are connected to pins 42-102 which extend above the plane of the CE chip. These pins 42-102 are positioned so that they are within the cut away portion of the second support and so are exposed. This allows suitable connections to be made to these pins 42-102 so as to apply the necessary voltages to them and to the electrodes connected to them.

The CE chip is shown with a single channel in which CE is performed, but channels suitable to perform separations on multiple samples could be provided.

9) PCR Chamber Sealing

In the embodiments described elsewhere, the chambers and the valves which are used to seal the channels leading to and from them are separate. In the following embodiment, the chambers and the valves are integrated as a single component.

Figure 41A:
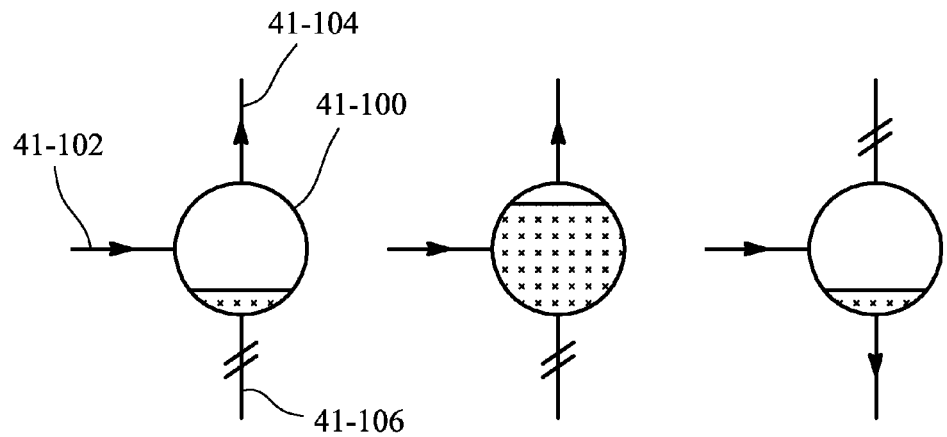
FIG. 41a shows three positions for an alternative PCR chamber embodiment.

As shown in FIG. 41a, the PCR chamber 41-100 is provided in the cartridge. However, the walls defining the circumference, at least, of the chamber 41-100 are rotatable within the body of material forming the cartridge. In the lefthand form, the rotatable wall is positioned such that the holes therein are aligned with the inlet channel 41-102 and the loading outlet channel 41-104. As a result, liquid can enter and gas leaves the chamber 41-100 until the chamber is full, centre form. The rotatable wall can then be rotated to align the holes therein with the inlet channel 41-102 and the dispense outlet 41-106, right hand form, to allow the contents to be emptied.

Figure 41B:
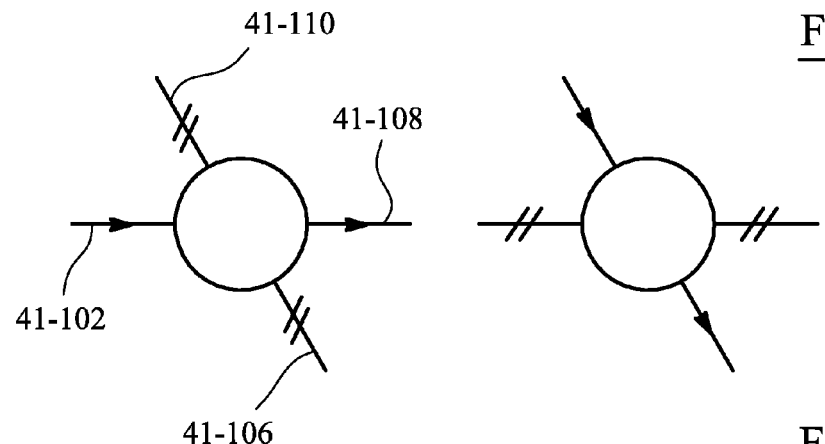
FIG. 41b shows two positions for a further PCR chamber embodiment.

A variant of this approach is shown in FIG. 41b, where inlet channel 41-100 is connected to outlet channel 41-108. Rotation aligns the holes with dispense inlet 41-110 and dispense outlet 41-106.

Figure 41C:
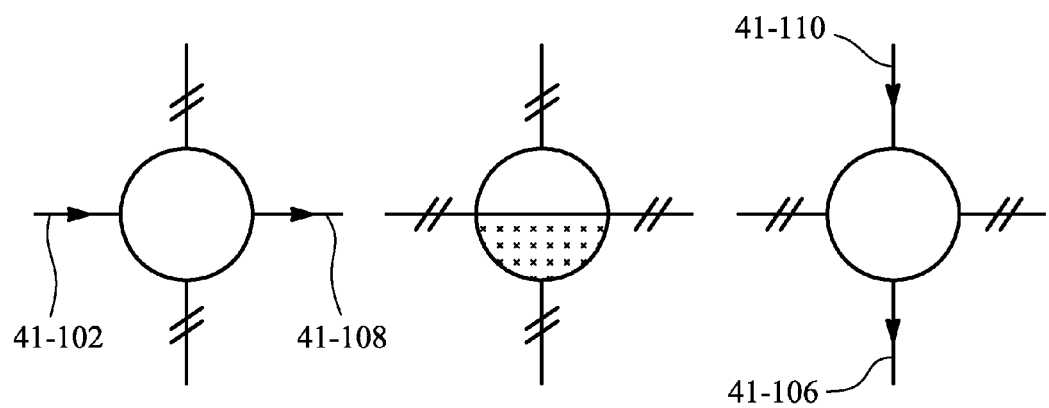
FIG. 41c shows three positions for a still further PCR chamber embodiment.

The variant in FIG. 41c uses the arrangement to seal the chamber during PCR. In the left hand form, the inlet channel 41-102 is connected to and fills the chamber up to the level of the outlet channel 41-108. Partial rotation offsets the holes in the rotating wall from alignment with any of the inlets/outlets, centre form. After PCR, further rotation aligns the holes with the dispense inlet 41-110 and dispense outlet 41-106.

The extent of rotation may be limited by abutment surfaces provide in the cartridge wall which abut surfaces on the rotating walls or vice versa. Partially circular forms for the hole in the cartridge which receives the rotating walls and/or vice versa may also be used to control or limit rotation in one or both directions.

Rotation may be provided by cooperation between an actuator and a slot in the circular wall.

Rotation may cause pads or other pliable material to be compressed or otherwise deformed to give sealing.

One or more of the channels may serve as a light path, rather than or in addition to being a fluid flowpath, so as to allow an investigatory instrument to shine light into the liquid contained within the chamber. Such an embodiment is useful in the context of the cartridge variant for real time PCR discussed above.

Instrument Configuration and Appearance

The instrument 11 is illustrated in FIG. 12 and is provided within a casing 8000. The mid section 8002 of the instrument 11 is provided with a door 8004 provided with a latch 8006. Behind the door 8004 is the location at which the cartridge 9 is mounted in use. This location is a position in which the plane of the cartridge 9 is parallel to the plane of a printed circuit board 8008. At the location, the cartridge 9 and components on the printed circuit board 8008 contact one another.

Behind the printed circuit board 8008 are the electronics for operating and controlling the components provided on the printed circuit board 8008. These include the power supplies, voltage controllers, temperature controllers and the like.

The upper section 8010 of the instrument 11 provides the display 8012 by means of which the user inputs information into the instrument 11 and receives visual information from the instrument. The software and hardware for operation of the display 8012 are provided on a computer positioned behind the display screen 8012 in the upper section 8010.

The lower section 8014 of the instrument 11 contains the high voltage power supply and controller for the laser used in the inspection of the capillary electrophoresis. Also in this lower section 8014 are the charge couple device used to sensor the fluorescence and the optics for conveying the light to and from the capillary.

Figures 29A, 29B:
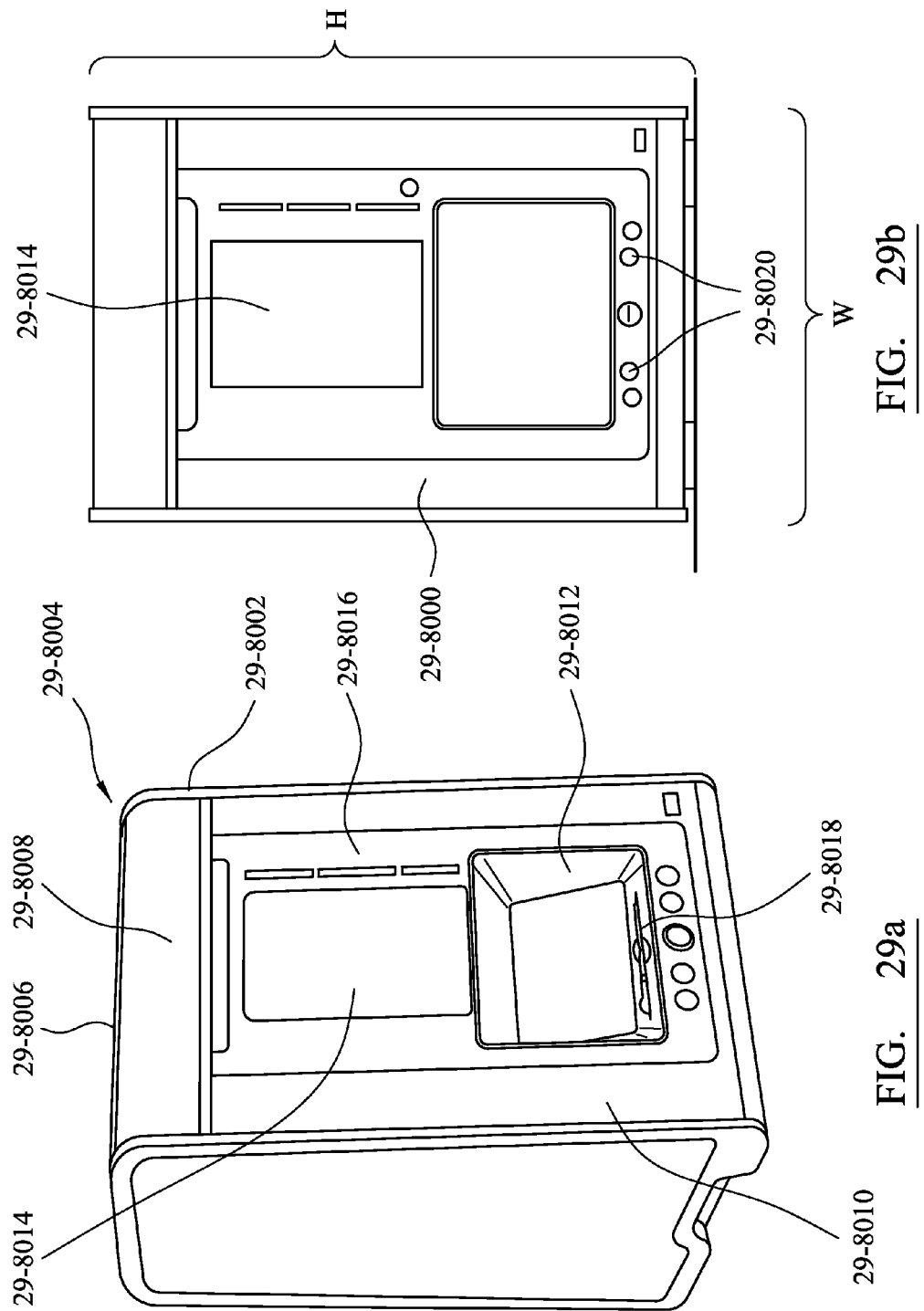
Figures 29C, 30:
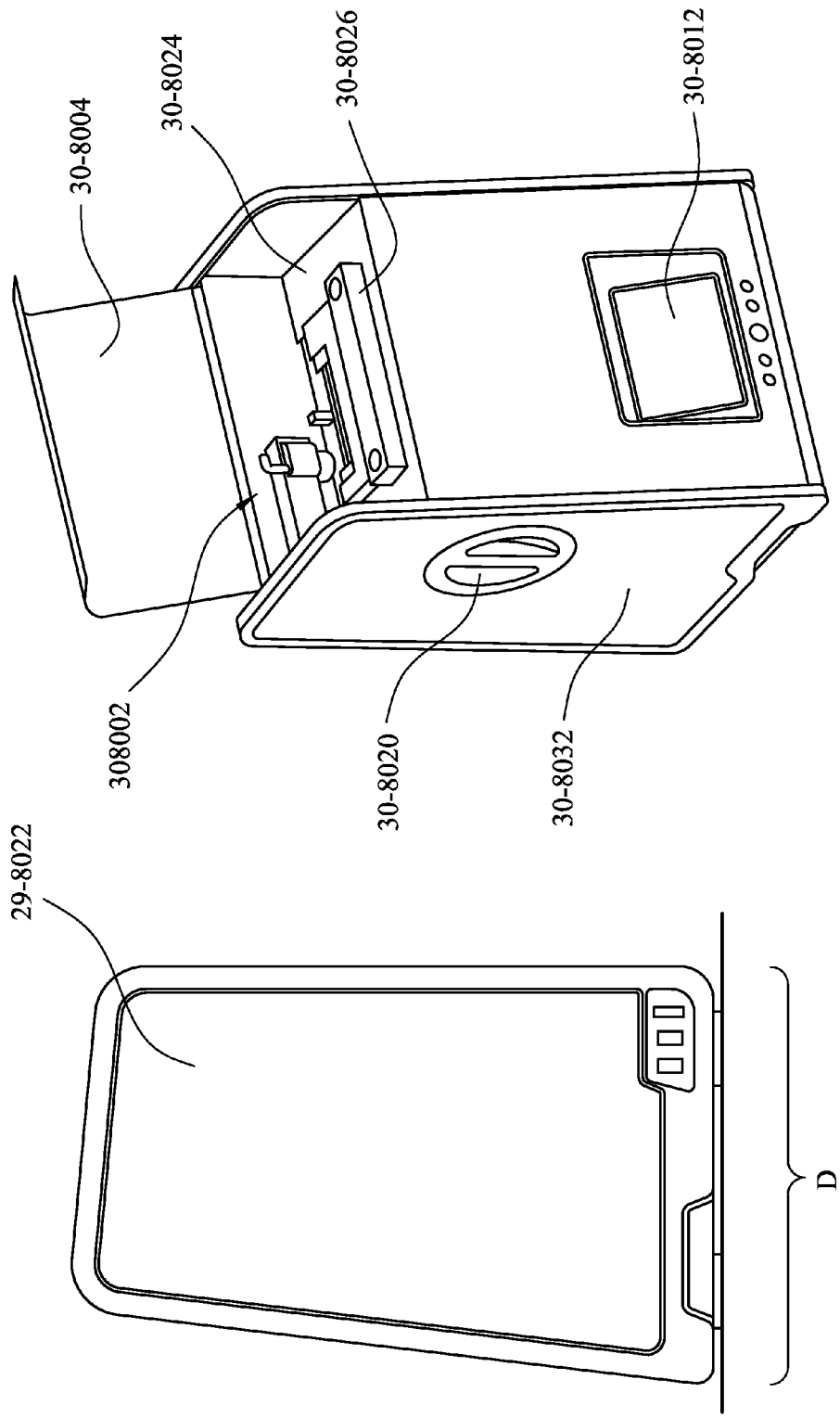

Another embodiment of the instrument is shown in FIGS. 29a, 29b and 29c. The instrument 29-11 is provided within a casing 29-8000. The upper section 29-8002 of the instrument 11 is provided with a door 29-8004. The door 29-8004 is a combination of a top section 29-8006 and front section 29-8008 of the casing 29-8000.

The lower section 29-8010 of the instrument 11 provides the display 29-8012 by means of which the user inputs information into the instrument 11 and receives visual information from the instrument 11.

The window 29-8014 allows for visual inspection of the cartridge used. A series of light bars 29-8016 are used to indicate the extent of progress through the steps involved; the more of the bar which is lit the greater the extent of the step performed.

A stylus 29-8018 is used by the operator to interact with the display 29-8012.

Various control buttons 29-8020 are provided below the screen 29-8012.

The overall dimensions of the instrument are width, W, 419 mm, overall height, OH, 621 mm, depth, D, 405 mm.

The side panel 29-8022 is removable for maintenance purposes.

The embodiment of FIG. 30 shows the door 30-8004 structure more clearly, together with the workspace 30-8024 that is accessed through it. The workspace 30-8024 includes the slot into which the cartridge carrier 30-8026 is inserted. The cartridge carrier 30-8026 is as described elsewhere in this document. The workspace 30-8024 also includes the lane finding apparatus 30-8028.

The cover 30-8030 in the side panel 30-8032 is opened by rotation to allow access to the optics for maintenance purposes.

Cartridge to Instrument Interface

As described above, once the cartridge 9 is loaded with the sample, the cartridge 9 is loaded into the instrument 11 for the processing to be conducted.

As a first step, the latch 8004 is released and the door 8002 is opened.

To insert the cartridge 9, FIG. 13, the section of the cartridge 9 which bears the PCR chamber 416 is inserted into a slot 8023 between the components which will control the PCR process. These components include the thermoelectric heaters/coolers, Peltier devices 8025, and fans 8027 there for. These components are free to travel to a limited extent to help with the locating of the cartridge 9 within the slot 8023, whilst being forcibly returned to the optimum position after insertion so as to give effective heating/cooling.

The cartridge 9 is provided with a series of recesses which cooperate with dowels extending through the printed circuit board 8008 to accurately register the cartridge 9 relative to the printed circuit board 8008. The dowel arrangement is such that the cartridge 9 cannot be fitted the wrong way round.

Once positioned, the cartridge 9 is provided in a plane which is parallel to the plane of the printed circuit board 8008. Both components have flat surfaces facing one another so as to assist with the good contact needed between them.

The closing of the door 8002 and operation of the latch 8004 applies a compressive force to the cartridge 9 by way of a series of spring loaded pins mounted on the inside surface of the door 8002. This helps hold the cartridge 9 in firm contact with the printed circuit board 8008.

The printed circuit board 8008 is important to the successful operation of the invention. It provides the energy sources for the various components to be driven on the cartridge 9. In effect, the drivers are all provided in the cartridge 9, but the energy sources are provided on the printed circuit board 8008. In this way, the precision operation needed is ensured by the expensive and bespoke electronics and arrangement of the printed circuit board 8008; a reusable component of the instrument. In this way, the cartridge 9 is simple and self-contained. This reduces the complexity of the interface between the two and also removes the risk of contamination of the contents of the cartridge 9. The only transfer between the printed circuit board 8008 and the cartridge 9 is conducted and radiated heat from the heaters and the magnetic field provided by the magnet.

The components provided on the printed circuit board include:
   a) The electrical contacts 9000 which connect to the pins of the electrochemical pump electrodes on the cartridge 9. These provide the electrical power, when needed, to operate the electrochemical pumps.
   b) The electrical heaters 9002 which are used to apply heat to the valves on the cartridge so as to open or close the valves depending upon their type. These are square areas of resistance heating material which is applied by printing a paste to the desired location. The heating effect is improved if the square block is rotated through 45° relative to the axis of the channel subject to the valve.
   c) The magnet 9004 which is advanced into proximity with the cartridge 9 when it is desired to retain the beads and prevent them from moving. The magnet 9004 is retracted away from the cartridge 9 when it is desired to release the beads within the chamber 358.
   d) The sensors 9006 are providing feed back and/or verification of the conditions induced by the heaters etc.

Alternatives for Cartridge to Instrument Interface

Figure 23:
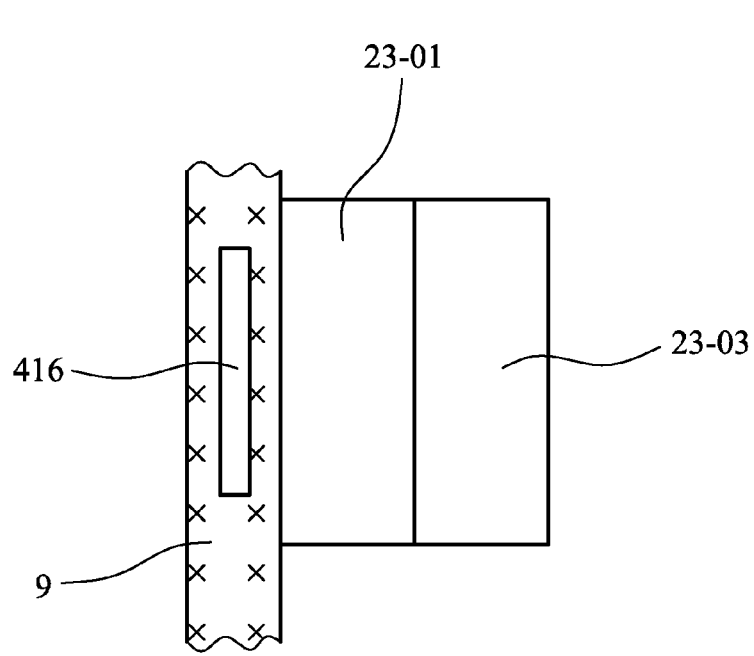
FIG. 23 is an illustration of the position of stacked Peltier effect devices.

If it is necessary to alter or improve the contact between the cartridge and the printed circuit board, there are various options for doing so, including the following:
   a) The loading provided by the sprung pins mounted on the door 8002 can be increased. This applies a force to the cartridge 9 and pushes it against the printed circuit board 8008.
   b) The cartridge 9 can be mechanically clipped to the printed circuit board 8008, with the clip(s) applying a compressive force.
   c) The cartridge 9 can be provided with a compressible substrate mounted on the surface which is intended to contact the printed circuit board. In this way, when then cartridge 9 and printed circuit board 8008 are pushed together, the substrate will provide good all over contact. The substrate can be a solid material, paste or even a liquid. The materials of the substrate, or parts there of, are selected so as to provide maximum thermal conductivity, for instance. Particles, nanoparticles or other materials may be added to alter the properties. The substrate may be protected, prior to use, by a peelable backing.

d) As described above, the components (such as heaters etc) are provided in a fixed position on the printed circuit board 8008. This means they move with the printed circuit board 8008. It is possible to provide one or more, and even each of these components with a degree of independent movement. For instance, they may be provided with a sprung mounting on the printed circuit board. In this way, each is able to independently adjust its position, forward and backwards, relative to the cartridge.

e) As shown in FIG. 23, it is possible to provide the section of the cartridge 9 which bears the PCR chamber 416 in opposition to stacked components which will control the PCR process. In this example, the stack includes a first Peltier device 23-01 in contact with the cartridge 9 and in contact with and aligned with a second Peltier device 23-03. The stacking of the devices allows high temperatures, for instance greater than 150° C. to be obtained within the PCR chamber. Such temperatures are beneficial in terms of melting the high melting point wax seals described elsewhere within this document.

f) Alternative forms of heater may be used instead of Peltier effect device. For instance infra red heating devices may be used. The material around the PCR chamber, or a part of that material, may be capable of resistance heating to give the necessary heating for the chamber. Resistance heaters positioned against the cartridge may be used. Microwave heating may be used.

Alternative Cartridge to Instrument Interface

In the alternative embodiments of the instrument described above in relation to FIGS. 29a, b, c and FIG. 30, the cartridge is not loaded directly into the instrument. Instead, once loaded with the sample, the cartridge 31-01 is loaded into a cartridge carrier 31-03.

The use of the carrier 31-03 means that the cartridge 31-01 and the CE chip can be constructed separately. This allows different material and/or different production tolerances to be used for the different components; a beneficial effect on cost and/or performance and/or the balance between those can thus be provided.

The carrier 31-03 also allows for easy assembly of the required components and their insertion into the instrument in a unitary form. At the same time, the carrier is designed so as to allow separate alignment checking and adjustment for the cartridge and the CE chip so that both are in their correct, optimised position within the instrument.

If desired, the cartridge position can be checked and any alignment adjustment necessary can be made. Before CE starts, a separate check can be made on the alignment of the CE chip, within any adjustments it needs being made before CE starts.

Figure 31B:
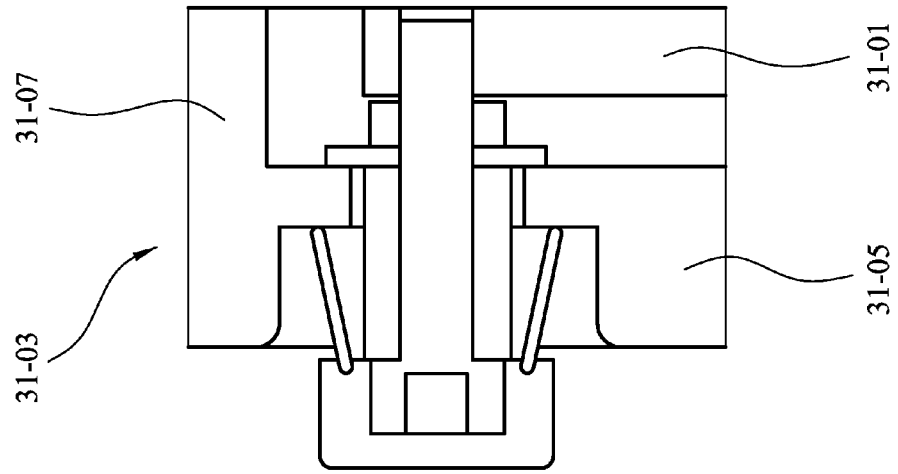
FIG. 31b is an illustration of a detail of the carrier to cartridge engagement.
Figure 31A:
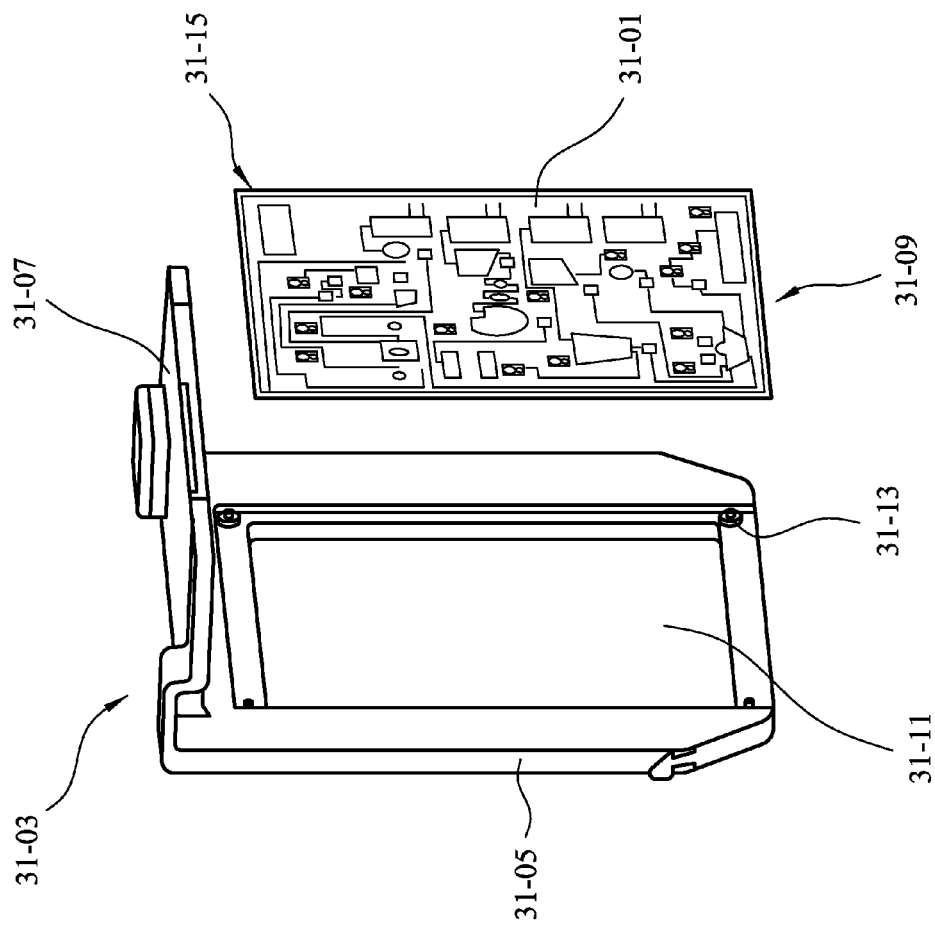
FIG. 31a is an illustration of a carrier, cartridge and CE chip embodiment.

The cartridge carrier 31-03 is illustrated in FIG. 31a. The cartridge carrier 31-03 includes a first support 31-05 and a second support 31-07 which is perpendicular to the first support 31-05.

The first support 31-05 is used to carry the cartridge 31-01. The second support 31-07 is used to carry the capillary electrophoresis, CE, chip; this interaction is described further below.

The prepared cartridge 31-01 is presented with its face 31-09 to the face 31-11 defined by the first support 31-05. An externally threaded screw 31-13 provided at each corner of the first support 31-05 is received into an opposing aperture 31-15 provided at each corner of the cartridge 31-01. Rotation of the screws 31-13 causes them to engage with and enter an internal screw thread provided in the apertures 31-15. Further tightening mounts the cartridge 31-01 on the first support 31-05 and hence the carrier 31-03 in a secure and known position.

The interaction between the cartridge 31-01 and the carrier 31-03 is shown in more detail in FIG. 31b in relation to one of the screws 31-13.

The screw 31-13 is provided with a knurled head 31-17. The threaded engagement occurs between the end 31-19 of the screw 31-13 and the aperture 31-21 in the cartridge 31-01. A jam nut 31-23 in cooperation with a washer 31-25 serves to hold the screw 31-13 on the carrier when not engaged with a cartridge 31-01 The jam nut 31-23. washer 31-25 and sleeve 31-27 serve to prevent over tightening between the carrier 31-03 and the cartridge 31-01.

Rotation of the screw 31-13 pulls the knurled head 31-17 and the cartridge 31-01 closer together. This causes compression of the conical spring 31-29 between the knurled head 31-17 and an abutment surface 31-31 on the first support 31-05. The spring 31-29 assists in ensuring correct alignment during tightening. Once rotation is finished, the first support 31-05 and hence carrier 31-03 is in a known position relative to the cartridge 31-01.

Figure 32A:
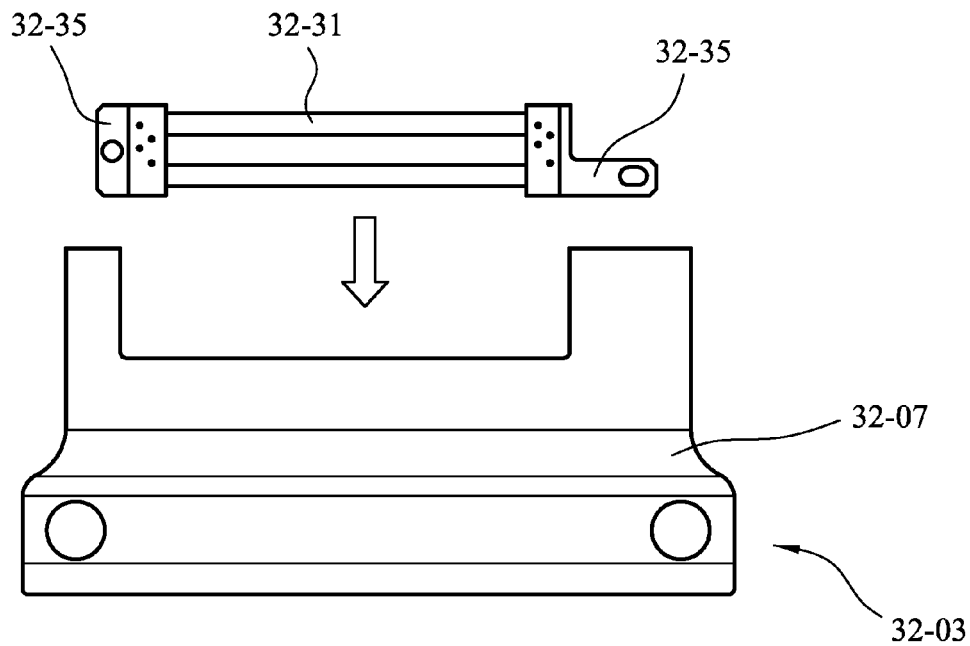
FIG. 32a is an illustration of a carrier to CE chip engagement.
Figure 32B:
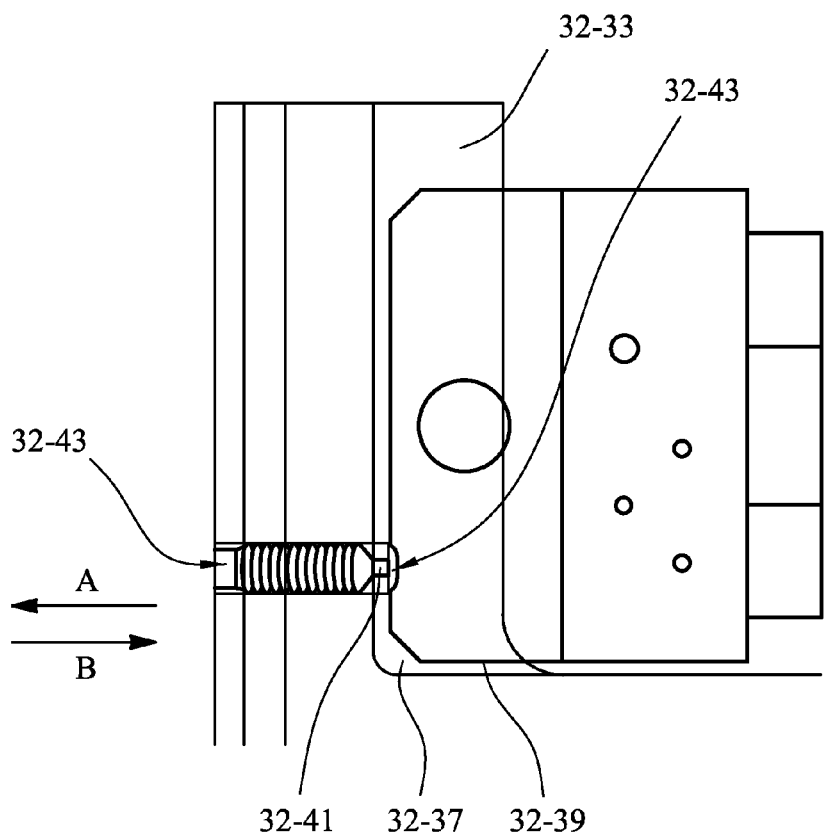
FIG. 32b is a cut away illustration of a part of the FIG. 32a engagement.

The CE chip 32-31 is inserted into the carrier 32-03 as shown in FIG. 32a. The CE chip 32-31 is slid into a slot. As shown in FIG. 32b, the second support 32-07 provides such a slot 32-33 at either end for receiving the end portions 32-35 of the CE chip 32-31. An incline 32-37 on the lead edge 32-39 of the CE chip 32-31 engages with the end 32-41 of a spring loaded plunger 32-43 and causes it to displace outward, arrow A. Once the recess 32-43 is presented to the end 32-41 of the plunger 32-43, the plunger 32-43 returns, arrow B, and so prevents onward movement of the CE chip 32-31 past the desired position.

Figure 33A:
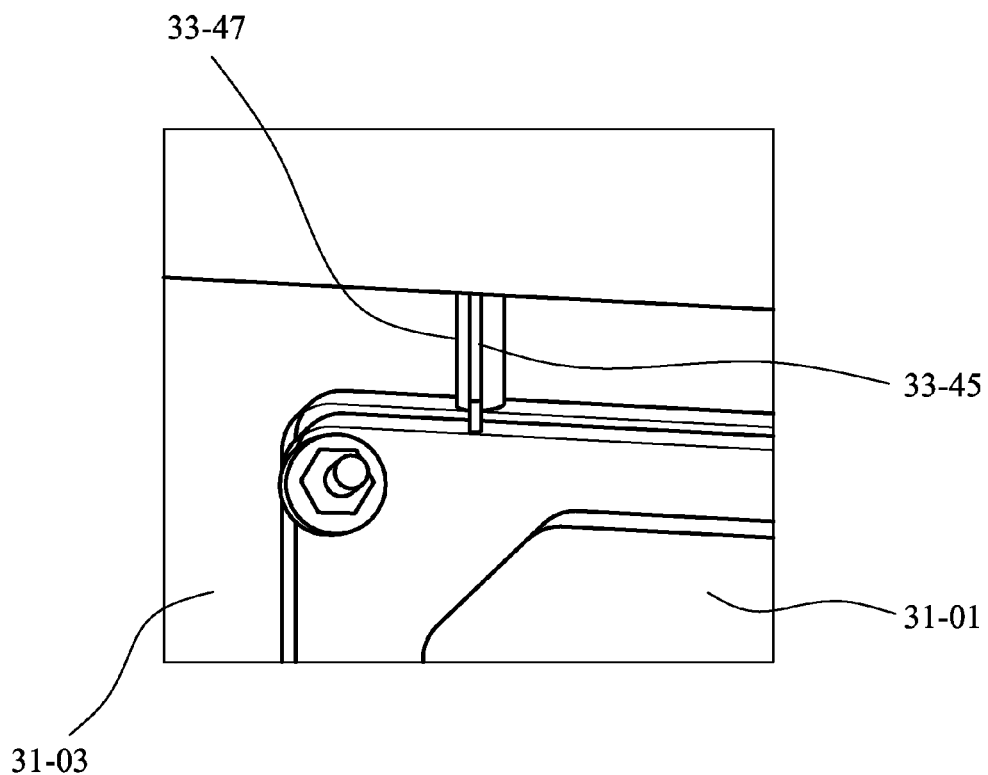
FIG. 33a is an illustration of the tube and cartridge connection.
Figure 33B:
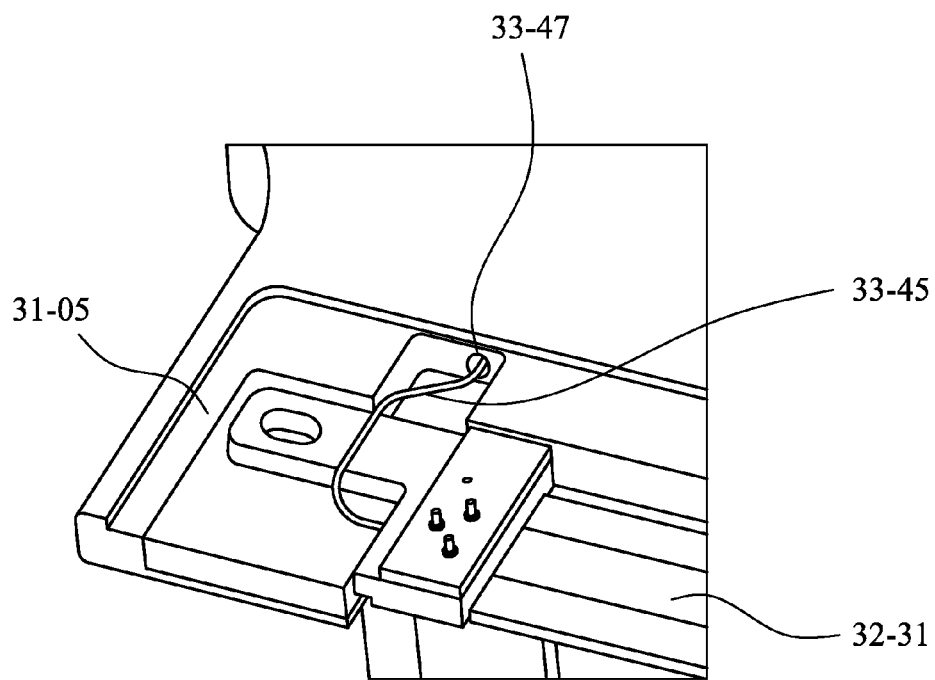
FIG. 33b is an illustration of the tube to CE chip connection.

Once the cartridge 31-01 and the CE chip 32-31 are inserted into the carrier 31-03, 32-03, the fluid connection between the two is provided by a tube 33-45. The insertion of the cartridge 31-01 into the carrier 31-01 causes the electrophoresis step inlet 28-570 on the cartridge 31-03 (see FIG. 28a) to become connected to the tube 33-45. As shown in FIG. 33a, the tube 33-45 extends upward, parallel to the plane of the cartridge 31-01 and the first support 31-05 through an opening 33-47 in the carrier 31-03. As shown in FIG. 33b, once through the opening 33-47, the tube 33-45 makes a 90° turn into the plane of the second support 31-07 and the CE chip 32-31. The tube 33-45 is accommodated within the second support 31-07 above the CE chip 32-31. A further 90° turn leads the tube 33-45 into the CE chip 32-31. The remaining fluid transport is handled within the CE chip 32-31 itself, as described elsewhere in this document.

After insertion of the cartridge 31-01 and the CE chip 32-31 into the carrier 31-03, as described above, the carrier 31-03 is ready for insertion.

Figure 34A:
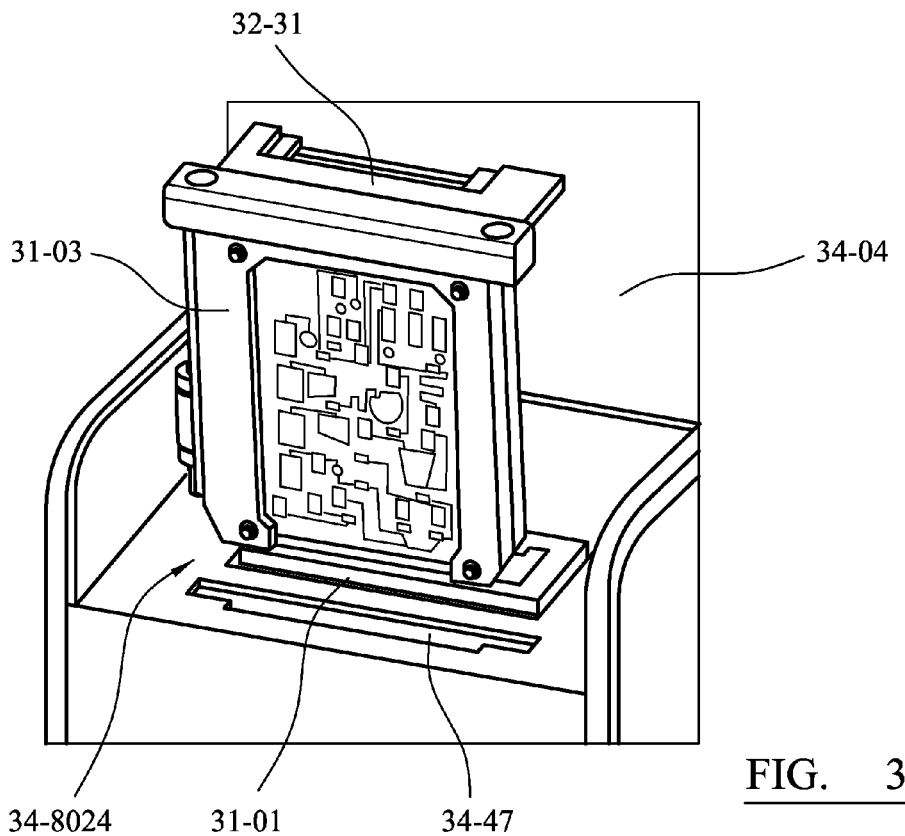
FIG. 34a is an illustration of the carrier being inserted into the instrument.

As a first step, the door 34-8004 is opened, FIG. 34a, to expose the workspace 34-8024. The work space 34-8024 includes the slot 34-47 that the carrier 34-03 is inserted into.

Figure 34B:
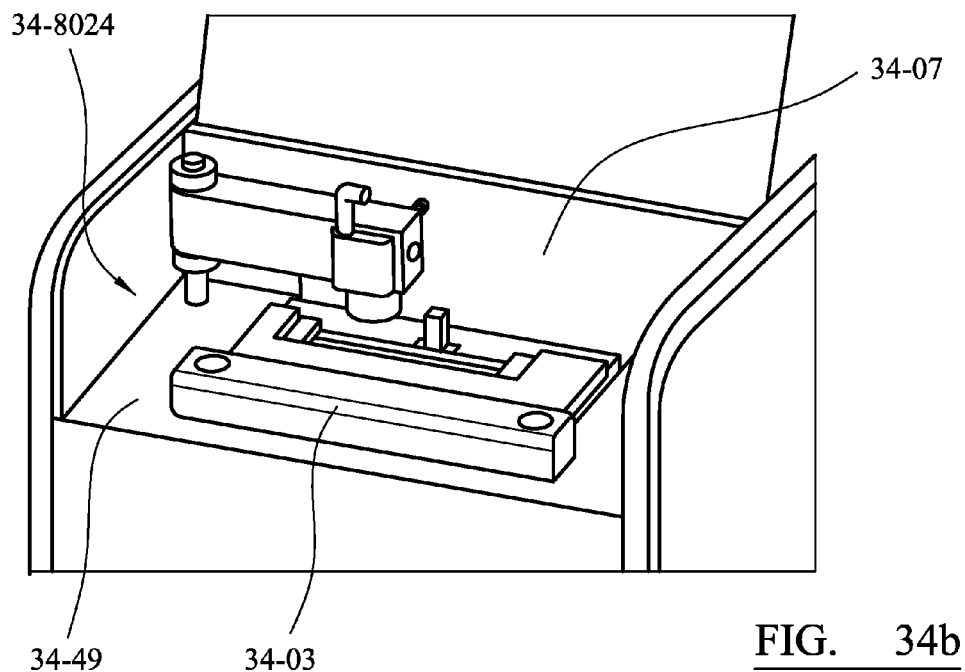
FIG. 34b is an illustration of the inserted carrier.

The carrier 34-03 is inserted into the slot 34-47 until the second support 34-07 comes to rest on the surface 34-49 of the workspace 34-8024. The cooperation of the carrier 34-03 with the slot 34-47 ensures the correct general positioning of the cartridge 34-01 with respect to the instrument, both in terms of lateral and vertical positioning; FIG. 34b.

Insertion in this way provides the section of the cartridge which bears the PCR chamber between the components which will control the PCR process; as described further below.

Once inserted, the door 34-8004 is closed. The closing of the door 34-8004 triggers various actions based upon contact between the closed door 34-8004 and casing. The clamping of the cartridge to the PCB, the positioning of the CE chip on the CE chip heater board, the introduction of the electrical contacts to the pins provided on the CE chip, the introduction of the electrical contacts to the pins providing the conduction path to the electrodes in the electrochemical pumps are all triggered in this way. The closure of the door 34-8004 is also used to turnoff the interlock for various safety systems within the instrument. The interlock prevents, for instance, the laser being active with the door or any other opening in the instrument's casing being open. a similar principle applies to the power supplies within the instrument.

As with other embodiments, it is important to provide effective and accurate contact between the cartridge and the instrument interface. In FIGS. 35a, b and c the provision of the contact is illustrated.

FIG. 35a shows the carrier 35-03 in position in the slot 35-47. In the insertion position, as shown, the arrangement provides for a gap 35-51 between the face 35-53 of the cartridge 35-01 which opposes the face 35-55 of the printed circuit board 35-57 of the instrument.

In the next step, FIG. 35b, the cartridge 35-01 is moved into the use position. A platen 35-59 is moved, direction of arrows, by an actuator, not shown. This causes the cartridge 35-01 to be brought into full contact with the PCB 35-57. The movement is such that the conical spring 35-29 is further compressed. During this movement, a series of rods which extend through the PCB 35-37 enter various holes (27-13 in FIG. 27) and so ensure that the alignment between the cartridge and the PCB is correct in that orientation too.

When the use of the cartridge 35-01 has finished, then the force applied to the platen 35-59 by the actuator is released. As a result, the carrier 35-03 is returned to the insertion position by return springs, not shown. The release causes the conical springs 35-29 to pull the cartridge 35-01 back into position inside the carrier 35-03, FIG. 35c. The carrier 35-03 can then be removed by lifting it out of the slot 35-47, taking with it the cartridge 35-01.

The face to face contact between the cartridge and the PCB provides the majority of the interactions between the cartridge and the instrument, for instance, heating for valve control, sensor etc. The contact between the PCR chamber and its temperature cyclers are provided through further components, however; see FIGS. 36a, b, c and d.

Figure 36A:
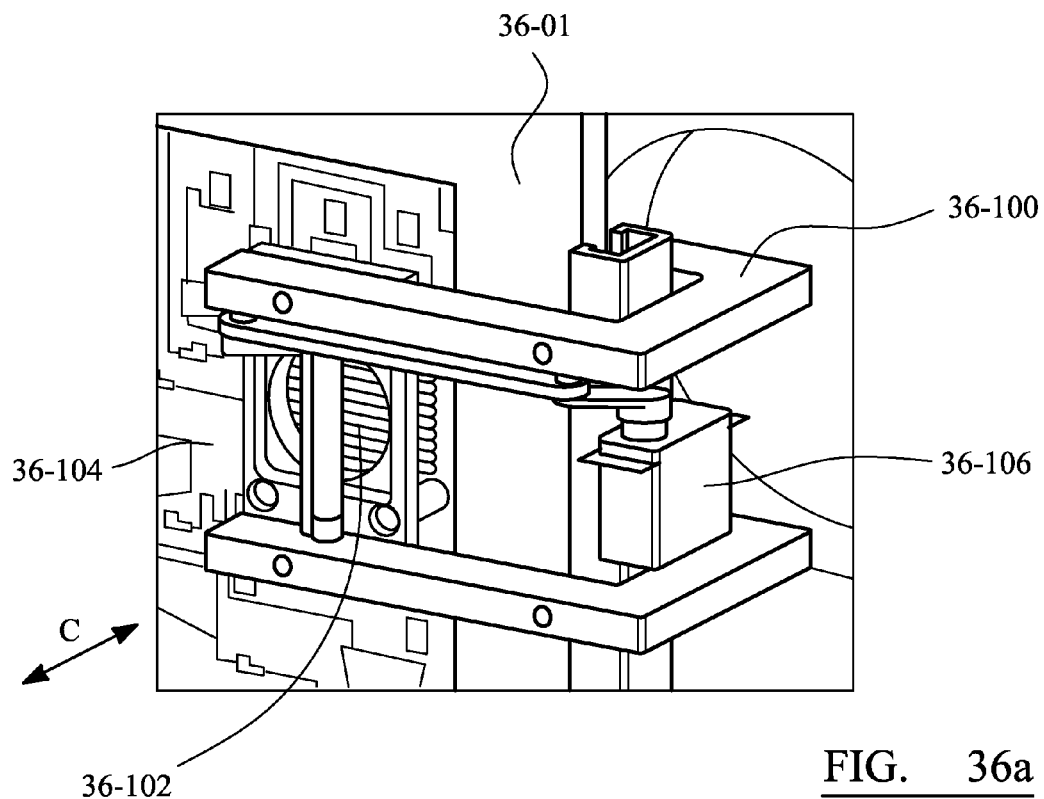
FIG. 36a is a perspective view of the position of the pair of calipers.
Figure 36B:
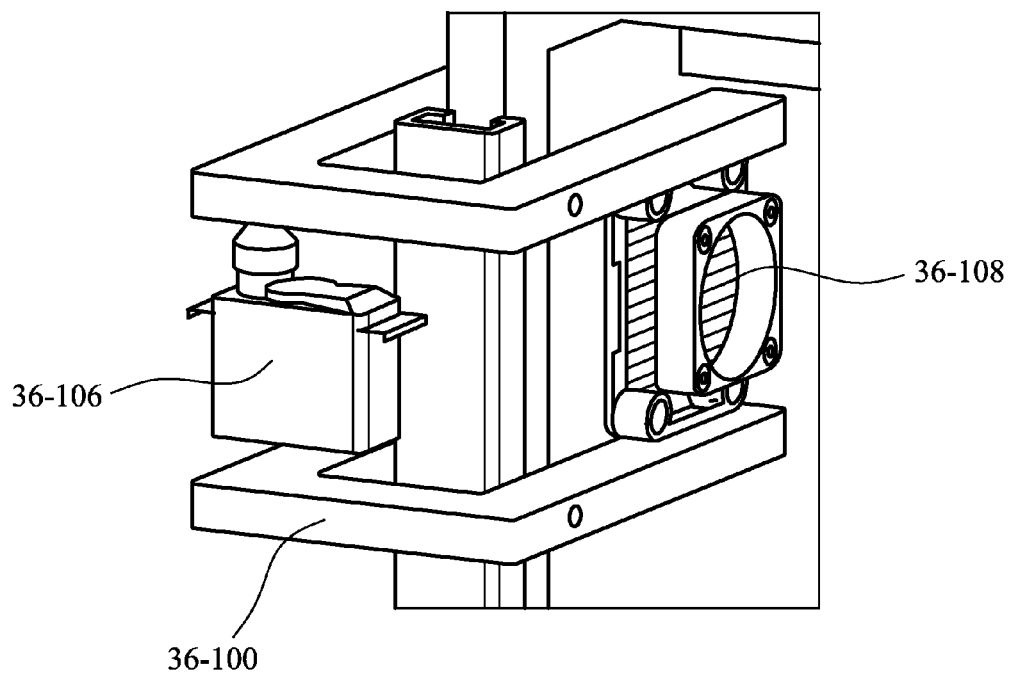
FIG. 36b is a perspective view of the back of the pair of calipers.

In FIG. 36a, the cartridge 36-01 is shown inserted into the slot provided in the instrument. Once inserted, the section of the cartridge 36-01 bearing the PCR chamber is positioned between a pair of calipers 36-100. The PCB is cut away at this location so as to not be in the way of the Peltier effect devices 36-102, 36-108 and pair of calipers 36-100. The calipers 36-100 are floating such that they do no interfere with the contact sought between the cartridge 36-01 and the PCB during the movement from the insertion position to the use position.

The front caliper 36-100a is provided with a Peltier effect device 36-102 mounted on a support 36-104 which is capable of reciprocating movement, arrow C, under the control of actuator 36-106. The actuator 36-106 is also mounted on the pair of calipers 36-100.

The back caliper 36-100b is provided with a second Peltier effect device 36-108 mounted fixedly on the caliper 36-100b.

The second Peltier effect device 36-108 is provided in opposition to the Peltier effect device 36-102.

Figure 36C:
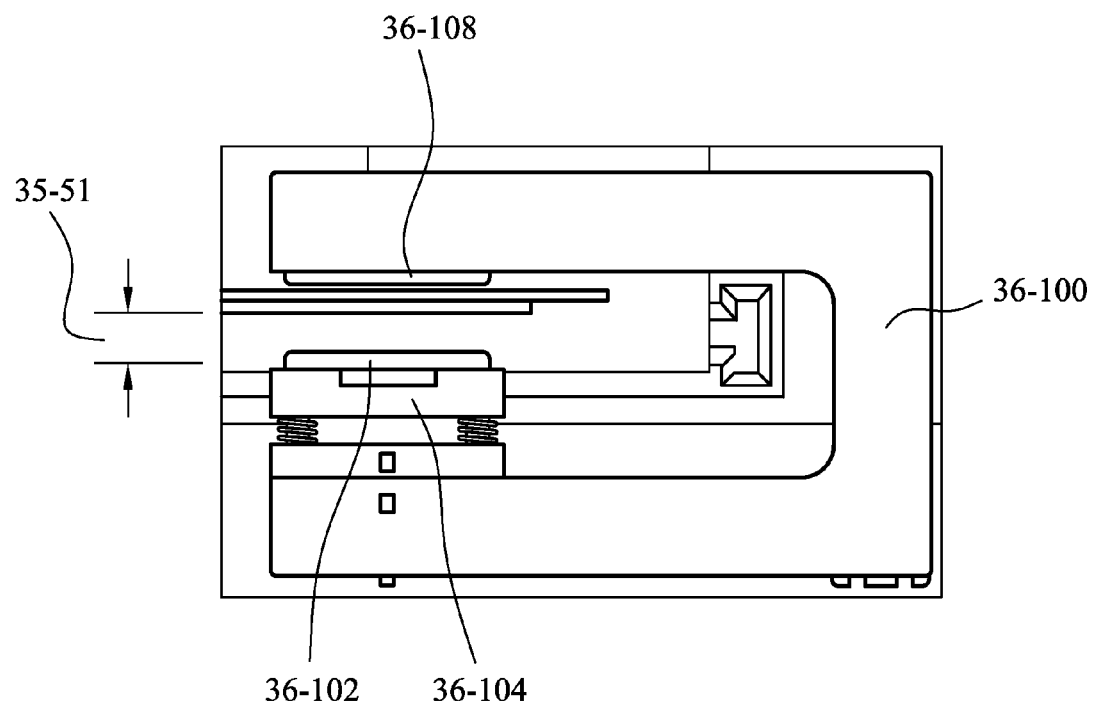
FIG. 36c is a plan view of the caliper structure in the open form.

In the open position shown in FIG. 36c, such as is provided with the cartridge in the insertion position, the distance between the opposing faces 36-110, 36-112 of the Peltier effect device 36-102 and the second Peltier effect device 36-108 is more than the thickness of that section of the cartridge 36-01 and more than the thickness of the carrier 36-03 which passes between the pair of calipers 36-100 during insertion of the carrier 36-03.

Figure 36D:
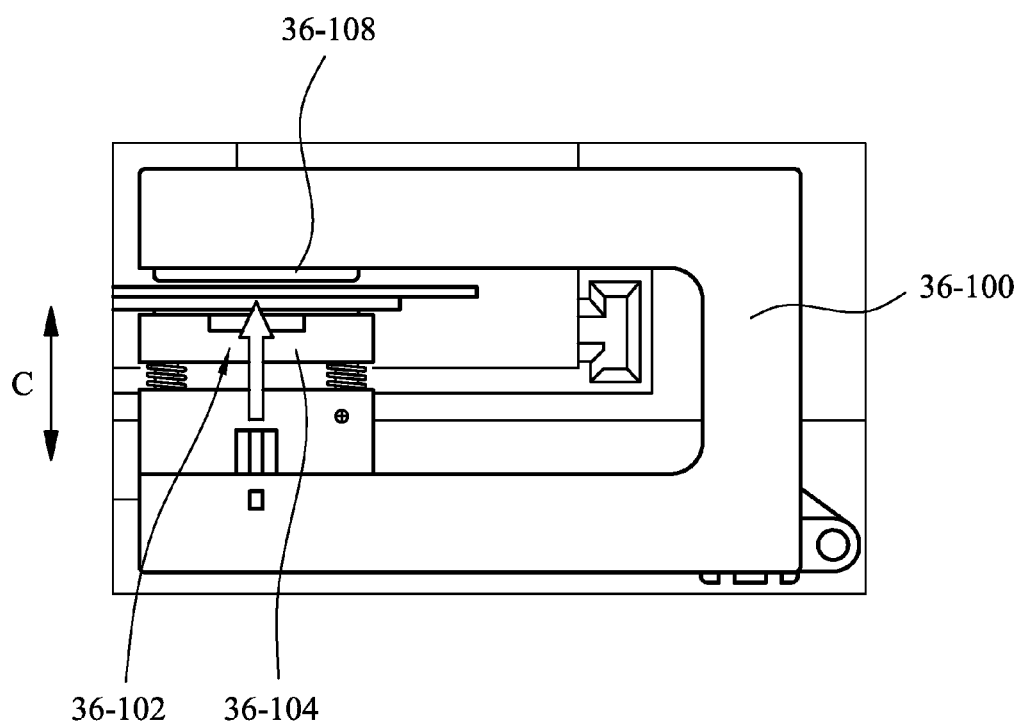
FIG. 36d is a plan view of the caliper structure in the closed form.

In the closed position shown in FIG. 36d, such as is provided during the amplification step, the distance is reduced. This is achieved by the actuator 36-106 moving the Peltier effect device 36-102 on the front caliper 36-100a towards the cartridge 36-01 and towards the opposing second Peltier effect device 36-100b. This actuation, combined with the floating nature of the pair of calipers 36-100 brings both of the Peltier effect devices into firm contact with the cartridge 36-01 on opposing sides thereof. They are now in position to provide the necessary heating and/or cooling for the PCR step.

Thermocouples to sense the temperatures applied, and potentially to be used to control the temperatures applied, are provided in close proximity with the Peltier effect devices, embedded in copper shims, bonded to the Peltier effect devices.

Before the carrier 36-03 is removed, the actuator 36-106 returns the Peltier effect devices 36-100 to the open position.

In addition to the carrier allowing for relative movement of the cartridge to ensure correct positioning with respect to the PCB, the carrier also allows for totally independent relative movement of the CE chip. This is importing in ensuring correct positioning of the CE chip for the CE step. This is achieved by the structure and operation shown in FIGS. 37a and b.

As the carrier 37-03 with the CE chip 37-31 in it is inserted into the slot in the instrument, the second support 37-07 approaches the work surface 37-49. The work surface 37-49 carries a CE chip board heater 37-100 in the form of a planar surface. this is surrounded by a raised surface 37-102 which provides a nest for the CE chip 37-31 once positioned.

Projecting pins 37-104 on the work surface 37-49 enter apertures 37-106 provided in the second support 37-07 of the carrier 37-03; FIG. 37a. In FIG. 37b, the top part of the second support 37-07 is shown cut away so that the full extent of the CE chip 37-31 can be seen. The apertures 37-106 in the second support 37-07 align with the slot 37-108 which receives the end portions 37-108, 37-110 of the CE chip 37-31. As a result, the end portions 37-108, 37-110 are also provided with through apertures 37-112a, 37-112b. The projecting pins 37-104 thus pass through these apertures 36-112a, 36-112b too as the carrier 37-03 approaches the work surface 37-49.

Figure 38:
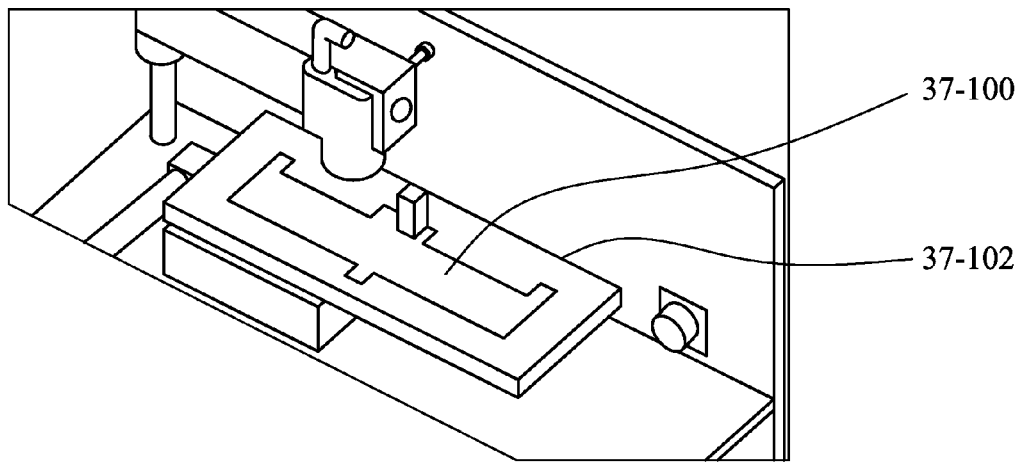
FIG. 38 is a perspective view of the CE chip heater board.

The conical ends of the pins 37-104 mean that they enter the apertures 37-106, 37-112a, b, even where there is potential misalignment. The fuller diameter parts of the pins 37-104 encourage the CE chip 37-31 into the correct position. The CE chip 37-31 is centred to the CE chip board heater 37-100 as a result. The CE chip heater board 37-100 and raised surface 37-102 can be seen clearly in FIG. 38.

Electrophoresis Components
1) Optics

In the electrophoresis step 206, at the detection location 628, light from a laser 800 is focussed to be incident upon the fluorescent dye associated with a DNA element to make it detectable.

A different dye is used for each different DNA element type; a type is generally associated with a given locus.

Figure 14:
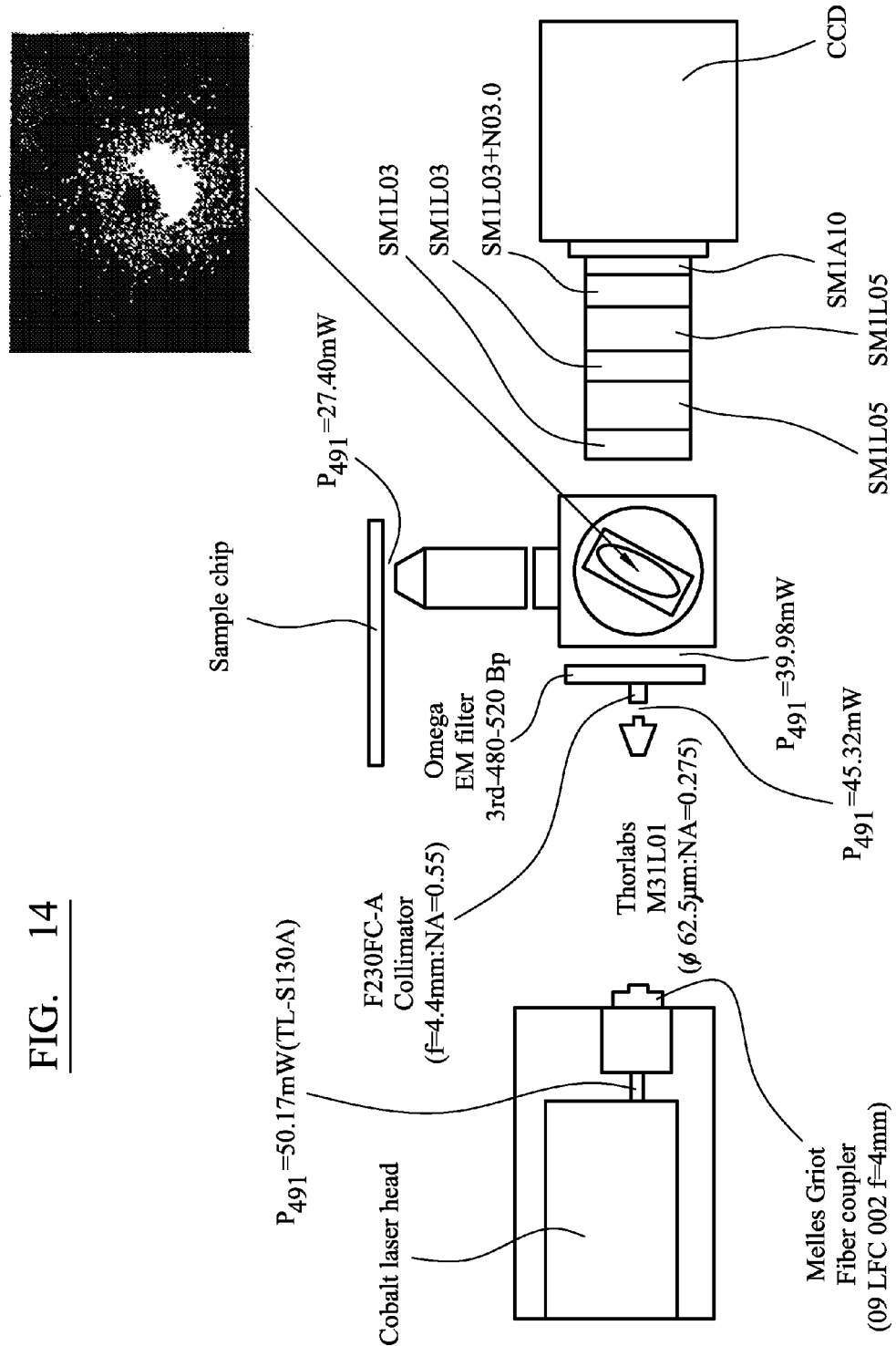
FIG. 14 is a schematic of the light source, optics and detector setup for the electrophoresis section of the instrument.

To get good sensitivity, it is important for the incident light to be of sufficient intensity for the detectors to receive sufficient light to be sensitive to the emitted fluorescent light, but for the intensity not to be so high as to give rise to photobleaching of the dyes. To provide for this, the following arrangement is used; FIG. 14.

The light source is a compact laser 900 which is mounted on a heat sink 902. The laser 900 is a Cobolt Calypso laser (from Cobolt AB, Kraftriken 8, SE-104 05, Stockholm, Sweden) and emits at 491 nm with a maximum power of 50 mW. The light emitted by the laser 900 is fed to a fibre coupler 904 (09 LFC 001, f=3.5 mm from Melles Griot, 2051 Palomar Airport Road, 200, Carlsbad, Calif. 92011, USA) and hence into an patch cable assembly (M31L01, from Thorlabs, 435 Route 206 North, Newton, N.J., 07860, USA) and optical fibre 906 (GIF625, dia 62.5:m, NA=0.275 from Thorlabs, 435 Route 206 North, Newton, N.J., 07860, USA).

The use of the optical fibre 906 is beneficial as it safely controls the laser light direction, enables the laser light to be easily conveyed to the position of use and enables mechanical stability to be provided within the overall system. At the end of the optical fibre 906 a power of up to 45.32 mW is still observed.

The laser light then passes through a collimator 908 (F230FC-A, F=4.5 mm, NA=0.55, from Thorlabs) and a log-pass filter with a sharp cut-off wavelength, EM filter (Omega Optical XF3093, T50=515 nm) before reaching the spot mirror 910.

The spot mirror 910 is used to both direct the laser light to the detection location 628 of the capillary and to transmit, anisotropically and without filtering, the fluorescent light received there from to the detector unit. It is angled at 45° to the beam of laser light. To do this, the reflector 910 consists of a 25 mm round glass disc which transmits all light from <80 above 380 nm. An ellipse, 2 mm long by 1 mm wide, is provided at the centre of the reflector 910 (so as to present an effective 1 mm circular mirror), formed of a highly reflective mirror layer deposited there (reflectivity of 99.99%).

Before reaching the detection location 628, the laser light passes through a focussing lens 912. This can be a microscope optic or other such adjustable focussing lens. Such optics are useful as they introduce no optical aberrations to the light, shape the beam for application to the detection location 628 and don't give any selective loss of light colours. The power reaching the detection location 628 is over 27.40 mW.

The fluorescent light is effectively scattered from the dye in the capillary 616 in all directions. For the fluorescence light to reach the detector unit, that light needs to hit the spot mirror 910 at a location outside of the glass spot. If it does so, the light is transmitted into the detector unit 914.

The detector unit 914 includes a slit in front of a spectrometer to obtain diffraction-limited incident light, the spectrometer provided with a diffraction grating and a lens 918 (LA1608A plano convex, f=50 mm, D=25 mm, with anti-reflective coating within 350-650 nm, made of BK7 glass, Thorlabs Inc), to direct the light to the charge coupled device 916. The CCD 916 has spectroscopic abilities.

Figure 15:
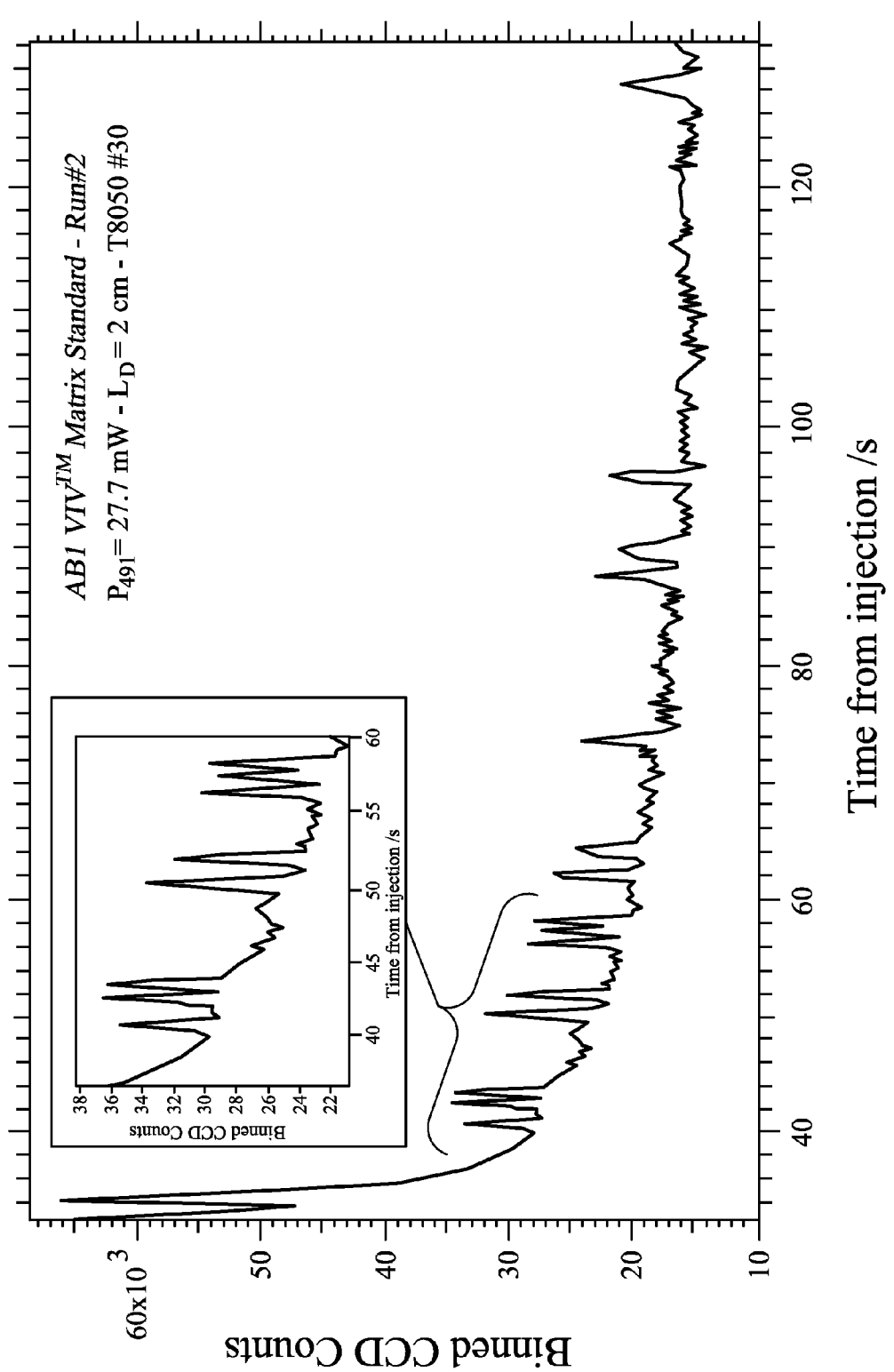
FIG. 15 is an electropherogram showing the variation in signal from the detector setup with time.

The CCD 916 generates the signals which are then used to generate the electropherogram, an example of which is shown in FIG. 15

Using such an approach, a sensitivity approaching that of laboratory style electrophoresis instruments can be reached. The instrument is able to detect down to the presence of 2.5 pM of fluorescein dye at pH 7.

In an alternative approach, certain problems with the stability of the fibre optics can be avoided by providing an open beam approach to delivering the light from the laser to the channel.

Figure 39:
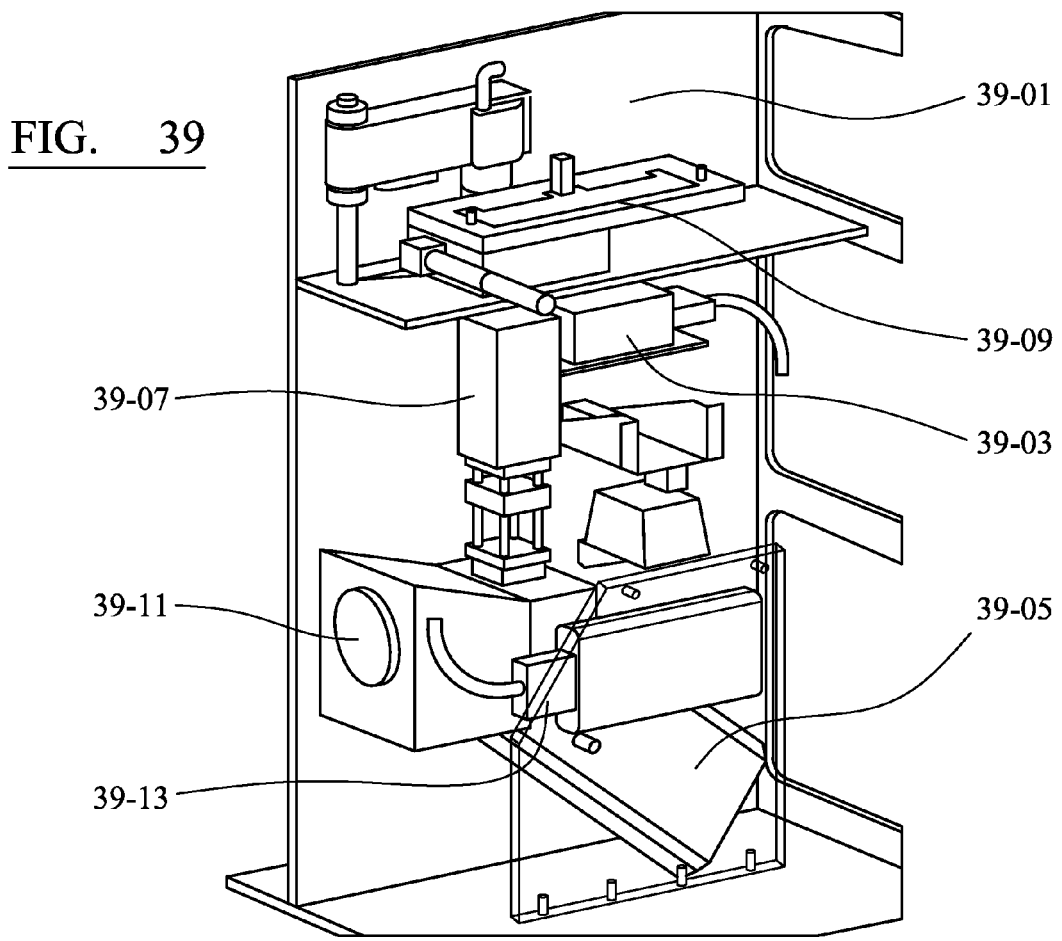
FIG. 39 is a perspective view of an embodiment of the optics.

An alternative embodiment of the optics is shown in the cut away perspective view of FIG. 39. The instrument casing 39-01 provides various mounts for the optics. The light is generated by the laser head 39-03 operated under control by the laser controller 39-05. The light enters the optics 39-07 and is directed at the channel in the CE chip, not shown, mounted in the CE chip heater board 39-09.

The return light enters the optics 39-07 and is directed back to the spectrometer 39-11 and CCD camera 39-13. Above the CE chip heater board 39-09 is the chip alignment structure 39-15 which is described further below.

2) Calibration and Verification for Optics

When first using the optics for detecting the electrophoresis results, and periodically thereafter, it is beneficial to ensure that the optics are properly calibrated to the capillary 616 at the detection location 628 in the electrophoresis cartridge section. This ensures best transmission of the excitation light into the detection location 628, best recovery of the fluorescence light from the dyes encountered at the detection location 628 and the performance of the detection at the detection location 628 (and hence at the correct distance from the point at which the sample is injected).

To achieve these aims, the electrophoresis cartridge section is provided with various aids. These are intended to allow automated verification and calibration of the position by the instrument 11.

Firstly, a fixed marker is provided on the electrophoresis cartridge section, a known distance along the capillary 616 and a known distance perpendicular to the capillary 616, from the detection location 628. When the laser light is incident upon the fixed marker, a response is detected by the CCD 916. The position of the incident laser light is thus known. The incident position of the laser light along the capillary is thus correct. The known distance of the fixed marker from the detection location 628, perpendicular to the capillary 616 can then be used to adjust the position at which the laser light is incident so as to correspond with the detection location 628. X and Y axis verification of the incident laser light position corresponding with the detection location 628 is thus provided. The marker could be a physical mark (for instance etched) on the cartridge and/or a coloured mark (for instance a dye) and/or a quantum dot.

To provide for the verification on the Z axis, the working distance between the lens and the capillary 616, a known source, with a known characteristic is provided on the electrophoresis cartridge section at a known Z axis distance relative to the correct Z axis distance of the capillary 616. By adjusting the focus of the lens so as to maximise the response by the CCD 916, the correct working distance for the known source is established. An adjustment can then be made to reflect the relative working distance for the known source relative to the capillary 616. Ideally, these are in the same plane at the same working distance so as to allow the known to provide direct verification for the Z axis position relative to the capillary 616.

As an alternative means of verification on the position, it is possible to use the marker for the X axis and then use variation in transmission to check the Y axis position. Thus a marker is used to determine the correction position along the axis of the capillary 616. The adjustment can then scan in the Y axial direction are use the CCD (or another detector) to consider the variation with position. The reflected signal will be constant at a level when the laser light is incident on the cartridge away from the capillary. When incident light traverses the capillary 616, then the signal will vary in a predictable manner, so allowing the position to be set subsequently at the position corresponding to the middle of the capillary 616 in the signal. To assist in this, it is possible to introduce a polariser insert for the calibration part of the process so as to increase the observed variation in the signal. The polariser is removed before the actual electrophoresis results collection starts. The effect whose variation is detected can arise from the capillary 616 itself, a marker at a known distance from the capillary 616 or a material present in the capillary 616 (for instance, a dye labelled component provided as part of a sizing standard, whose mobility is higher than the other elements of the size standard or unknown elements).

Figure 40A:
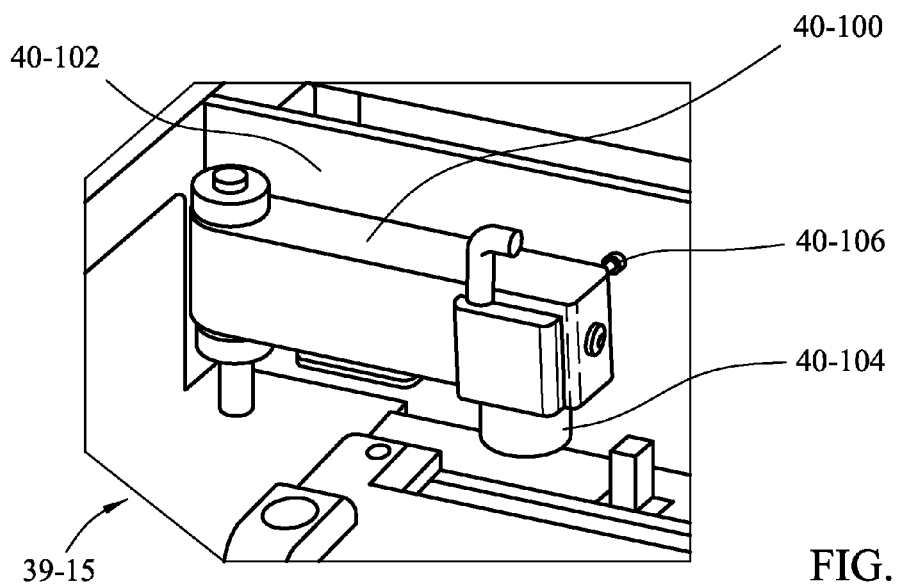
FIG. 40a is a perspective view of the alignment structure.

The FIG. 39 and FIGS. 40a, b and c embodiment shows the alignment structure 39-15 and its operation.

The alignment structure 39-15 is in the form of a swing arm 40-100 which can be pivoted relative to the casing 40-102 under the power of an actuator contained within the swing arm 40-100. The other end of the swing arm 40-100 is provided with a camera 40-104.

Figure 40B:
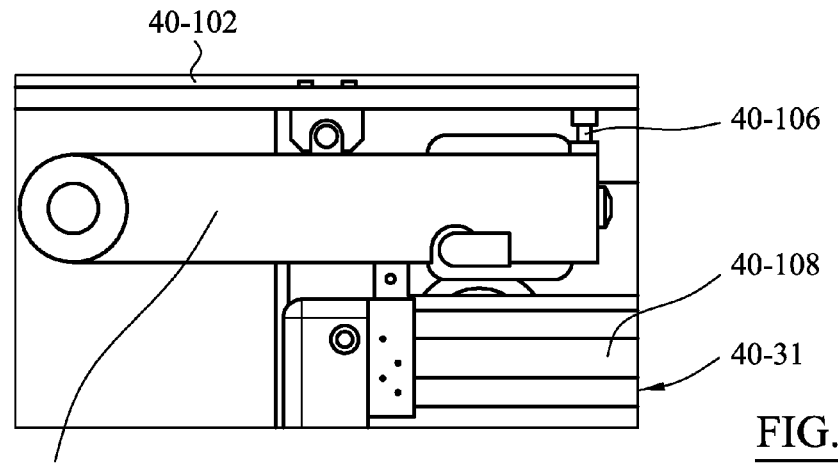
FIG. 40b shows the alignment structure of FIG. 40a in the stowed position.
Figure 40C:
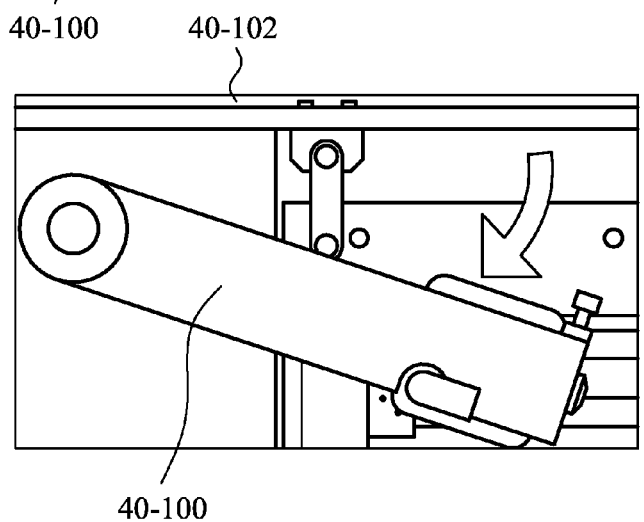
FIG. 40c shows the alignment structure of FIG. 40a in the use position.

In the stowed position, FIG. 40b, the swing arm is positioned in contact with a hard stop 40-106 mounted on the casing 40-102 too. In the check position, FIG. 40c, the actuator has caused the swing arm 40-100 to swing away from the casing 40-102 and so position the camera 40-106 over the channel 40-108 in the CE chip 40-31.

In the use position, triggered by the operator, a laser is activated and this creates a diffraction pattern which can be seen on the camera display. The adjustment for the CE chip position is used to move the CE chip until the diffraction pattern indicates that the middle of the channel has been located. The alignment of the channel with the optics used in the analysis is thus provided. The camera can also be used to achieve focussing of the system in the Z axis adjustment.

3) Electrophoresis Environment Control

For the necessary resolution to be obtained in the electrophoresis step 206, the temperature of the capillary 616 and its contents need to be carefully controlled at the optimum temperature. In the present embodiment, the electrophoresis cartridge section is in contact with a thermally conductive block, with a series of resistance heaters provided on the opposing side of the block. These are provided with controllers and are capable of maintaining the temperature of the electrophoresis cartridge section at the optimum temperature +/−0.3° C.

In addition, the cavity that the electrophoresis cartridge section is provided in is thermostatically controlled at the optimum temperature. This reduces still further temperature variation before, during and after use.

The use of a CE chip heating bed, and raised surface around it, is beneficial in controlling the temperature within the CE chip. The nest so formed ensures consistent positioning and good contact.

4) Use of LED's as Light Source

Figure 16:
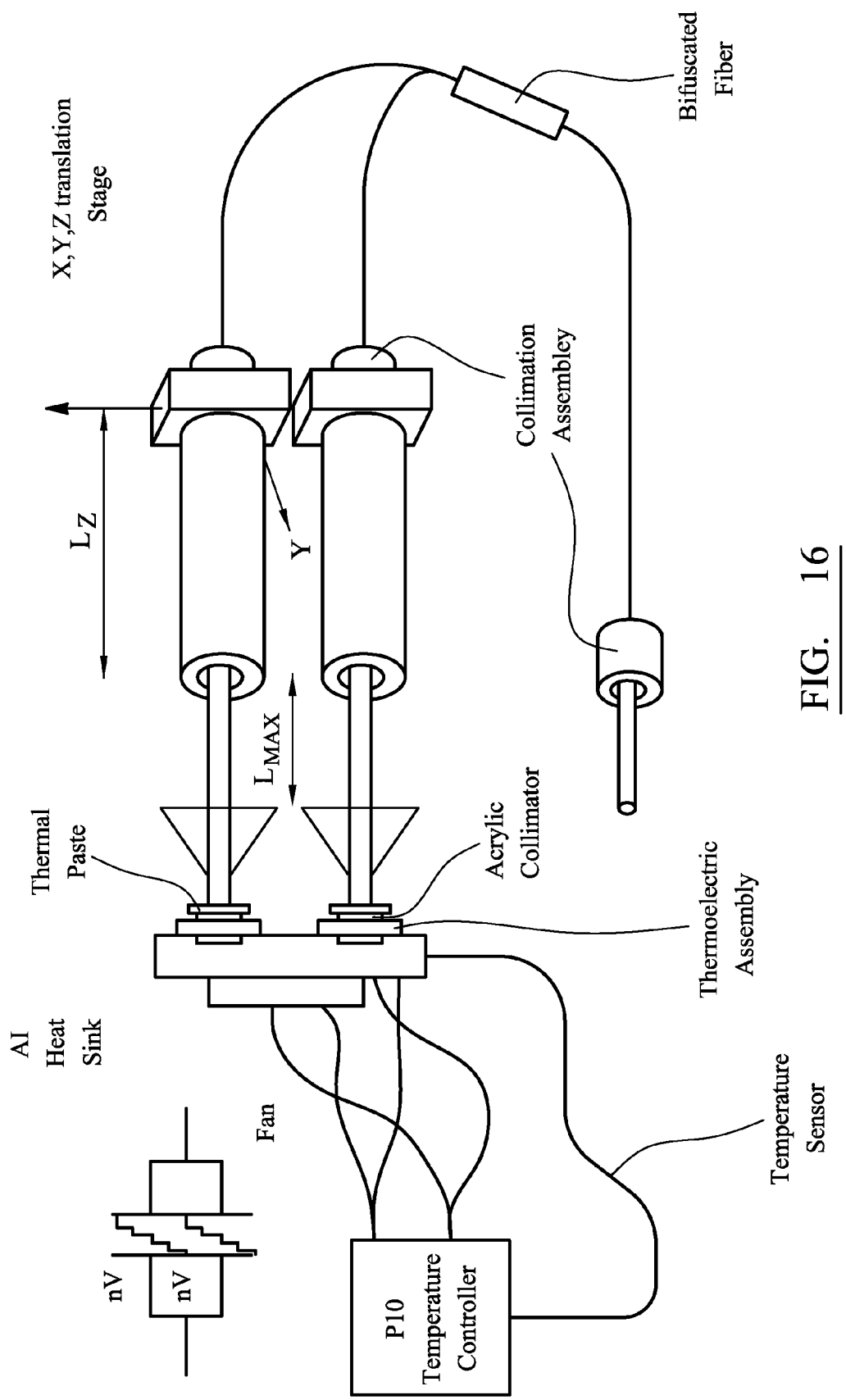
FIG. 16 is a schematic of an example of a system for detecting fluorescence.

FIG. 16 depicts a schematic of an example of a system for detecting fluorescence. The system includes light emitting diodes (LEDs), e.g., high power cyan LEDs, to provide excitation wavelength light to detect dyes combined with biological samples. The system also includes a bifurcated optical fibre assembly made, e.g., from high transmission fused-silica cores with high numerical apertures (NAs), e.g., NA=0.22. The LED excitation system described herein can be applied for DNA detection in capillary electrophoresis systems in mobile analytical units. The compactness and light weight of the LED system enables automating assays for nucleic acid studies. Using the compact and light weight system allows creating bench-top analysis systems that can be used both in the laboratory and in the field.

In some implementations, two LEDs are assembled in parallel and supplied with a stabilized DC voltage of 3.6 V. The current passing through the LED assembly is 1.8 A. The junction is maintained at 15±1° C. by a Proportional-Integrative-Derivative (PID) control loop (Model TE-36-25 from T.E. Technology, Inc.) acting on two 13×13 mm thermoelectric modules. To save power, and space, two Peltiers modules are controlled in parallel and the thermocouple sensor is placed on only one of them assuming that, by construction symmetry, they both behave similarly. An aluminum heat sink and a fan (12 V DC) complete the cooling module. This module extends the lifetime of the LEDs by two orders of magnitude. Without cooling the junction, the supplied current is 2.7 A.

The first step of collimation is the use of an acrylic-molded lens from Lumiled, which collimates the emitted light to a 15° cone half-angle (NA~n sin($2_{1/2}$)~0.26). The light is then focused onto a plano-convex lens (f=35 mm, D=25 mm; NA~D/2f~0.36). $NA_{LED} < NA_{lens}$, or the numerical apertures are matched. The distance between the apex of the lens and the plane of the collimator, $L_{max}$, is adjusted by a micrometer screw to maximize the power read by a calibrated silicon photodiode sensor. The value obtained (25 mm) is only close to the focal length f since the collimated LED is not a point source. The light beam is then refocused onto a collimation package assembled around an aspheric lens (f=10 mm, D=5 mm; NA~D/2f~0.25, Ocean Optics Ltd) within an anodized aluminum lens tube of length l=30 mm Each LED is thus coupled into one arm of a 2 m-long bifurcated silica core (Ø=600 μm, NA=0.22) optical fibre assembly (attenuation: 0.013 dB/m at 505 nm–relative transmission: 82% (arm 1) and 87% (arm 2)).

Table 1 illustrates a power optimization of the system depicted in FIG. 16. The power at 505 nm, P505, is read by the silicon photodiode while the distance between the LED collimator and the lens surface ($L_{max}$), the lens geometry, and the lens tube length (l) are changed. Only one arm of the bifurcated fibre is used.

TABLE 1

| Lens | I | $L_{max}$ | $P_{SOS}$ |
| --- | --- | --- | --- |
| Hemispherical | 3 cm | 20 mm | 225.2 μW |
| Hemispherical | 5 cm | 18 mm | 200.4 μW |
| Hemispherical | 8 cm | 19 mm | 222.8 μW |
| Cylindrical | 3 cm | 9 mm | 170.9 μW |
| Cylindrical | 5 cm | 9 mm | 164.1 μW |
| Plano-convex | 3 cm | 16 mm | 220.9 μW |
| Plano-convex | 5 cm | 15 mm | 204.1 μW |
| Plano-convex | 8 cm | 15 mm | 173.7 μW |
| None | None | 12 mm | 187.4 μW |

For the bias values described above, when both arms of the fibre are used, the power at 505 nm read by the photodiode is 820 μW.

Figure 17:
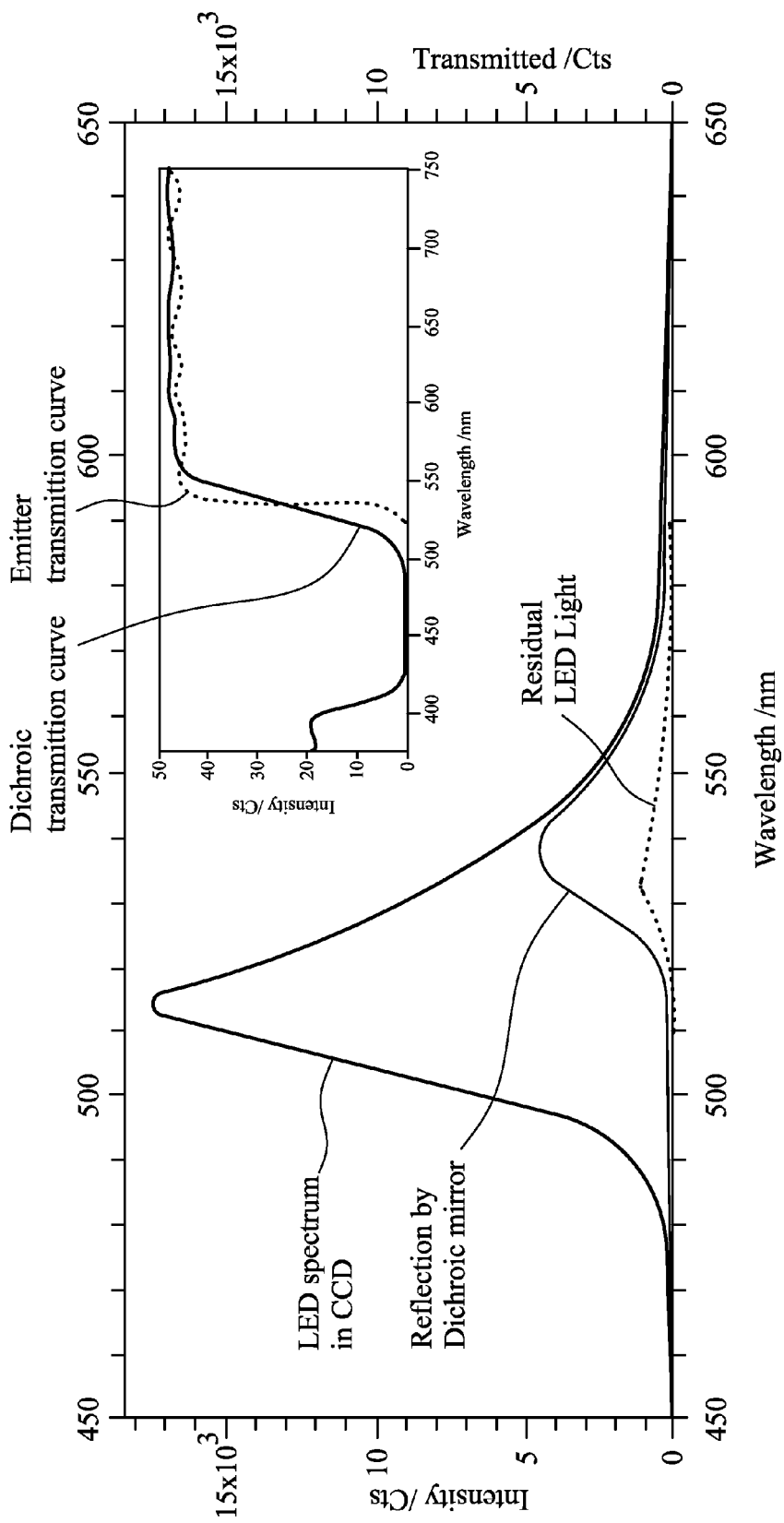
FIG. 17 is a plot of LED spectrum, light reflected, and residual LED light over a range of wavelengths.

FIG. 17 is a plot of LED spectrum, light reflected, and residual LED light over a range of wavelengths (nm). FIG. 17 illustrates an LED spectrum obtained in the cooled CCD (diodes: Ug=2.0 V; I=0.3 A; T=15° C.), calculated light reflected by the dichroic mirror, and residual LED light after the emitter. The insert shows the transmission curves of the dichroic and emitter. The plot indicates that there is a loss of power when the incident light is reflected onto the sample. Additionally, light is red-shifted by 20 nm, which causes some of the LED light to interfere with the carboxyfluorescein dyes. The choice of available emitters and dichroic mirrors is limited by the dyes chosen to label the migrating DNA strands.

Figure 18:
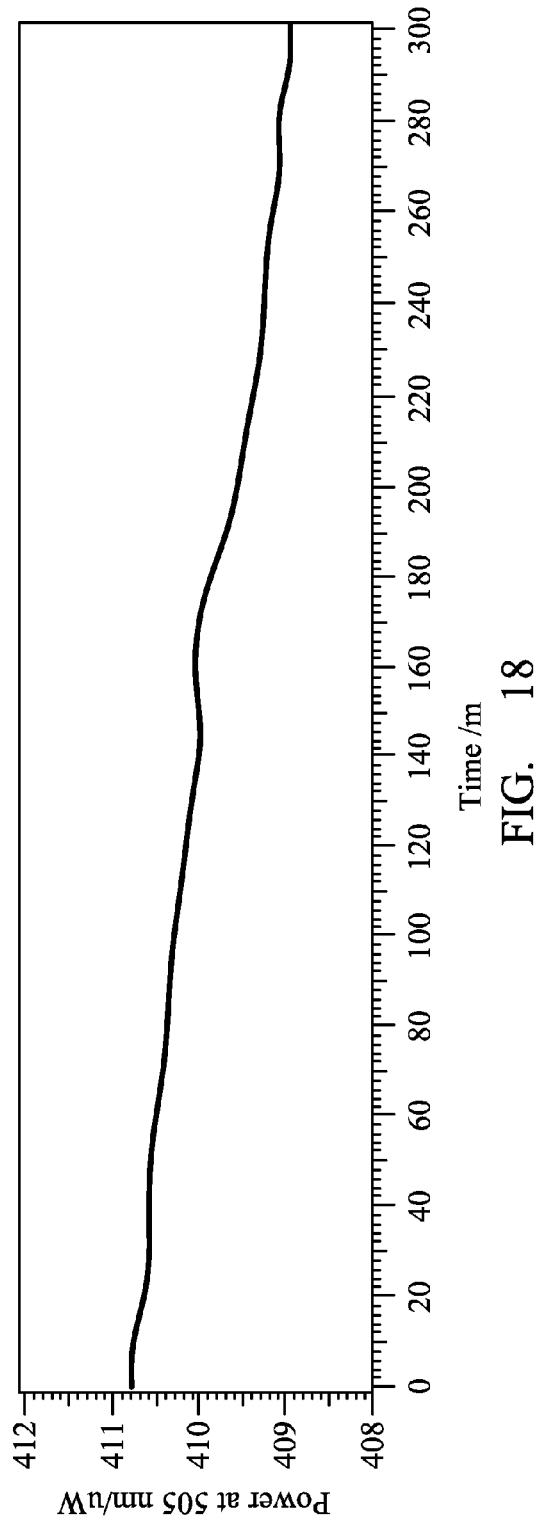
FIG. 18 is a plot of power of the LED-module over time.

FIG. 18 is a plot of power of the LED-module over time. During a CE experiment, it is crucial to reduce the fluctuations of the power of the light source within less than 1%. FIG. 18 shows an example of the power recorded by the silicon photodiode (Probe S130A, Thorlabs) using the internal calibration function to record the power emitted by the fiber-LED assembly at 505 nm over time. The diodes are supplied with a 3.4 V DC voltage corresponding to a current of 1.4 A while the junction is maintained at 15±1° C. The room is maintained at a temperature of 22° C. (R.H.=24%). The plot illustrates a temporal power evolution of the LED-module. The lines mark regimes where the power drops, e.g., by 4.8 nW/s, 11.6 nW/s, and 5.0 nW/s. Overall, the power drops by about 1.95 µW over 5 min, i.e. 0.48%.

Figure 19:
FIG. 19 is an illustration showing beam shape and size as measured by the laser camera.

FIG. 19 is an illustration showing beam shape and size after the sample objective as measured by the laser camera. The asymmetry observed is due to imperfections occurring when the two fibre arms are fused because of the large core diameter of the fibre, mismatches between the LED-to-LED and the fiber-to-fibre distances, and tilt in the optical elements. In the results reported in the next section, the situation corresponding to the single-spot will be used. One method includes adjusting all the optics to obtain the maximum power at the merged end of the bifurcated fibre. This can yield a misshapen light beam as the core size of each arm is large (multimode fibre). To characterize the beam shape and size after the microscope objective, i.e. at the entrance of the microchip, a Coherent Lasercam II ½ camera was placed on an {x,y,z} translation stage equipped with micrometer precision positioners and equipped with a Leica HCX PL FLUOTAR (40×, NA=0.75, WD=0.40 mm) and adjustable filters. The objective was brought within ~8 mm of the Olympus LUCPLFLN (20×, NA=0.45, WD=6.6-7.8 mm) mounted on the CE setup. This allowed directly imaging the beam coming out of the fiber-LED assembly via the CE setup. The micrometer positioners allowed measuring the dimension of the beam with a precision of 10 µm by moving the camera from one spot of the obtained beam profile image to another and reporting the traveled distance. The power can be maximized by adjusting each optical collimation element (P=1.6 mW at 505 nm) (A) or the collimation elements can be adjusted to give one single spot (P=1.0 mW at 505 nm) (B).

The system was employed for both static and dynamic fluorescence measurements. For the static fluorescence measurements, a 1 µM fluorescein, 6-FAM or rhodamine B solution is loaded into the microchannel by using a standard laboratory vacuum line (13 PSI (0.88 atm) depression) to pull the solution through the channel via 2-mm-diameter access holes. The glass microchannel is anisotropically etched with fluorhydric acid (HF) in Schott Borofloat® low-fluorescence glass (CE chip X8050, Micronit, B.V., The Netherlands). It is semi-elliptic with a width of 50 µm, a depth of 20 µm and a length of 85 mm. The plastic microchannels are hot-embossed into a 1.1-mm-thick cyclic olefin copolymer (COC) sheet at ~160° C. from a reactive-ion etched Si(100) master. The channel section is tapered with a 25° taper angle and has a width of 60 µm (top) and 39 µm (bottom), a depth of 20µ and a length of 85 mm. Glass capillaries that are 1-cm-long (inner diameter 4 mm) borosilicate are epoxy-glued onto the access holes to act as reservoirs (or wells). All solutions are filtered with a nylon membrane (pore diameter: 0.2-µm) to remove small particles that will clog the channel.

The loaded chip is placed on the CE setup and the focus of the 63× sample objective is aligned with the bottom of the channel. The emitted fluorescent light is gathered onto the 26.6 mm×6.7 mm (1024×255 pixels) array of the thermoelectrically cooled Andor CCD. The processed signal is vertically binned from the software-restricted central rows irradiated by the light focused onto the spectrometer entrance slit. The CCD is cooled down to −50° C. to reduce the binned dark counts to 270 while the exposure time is 0.05 s.

FIGS. 21A and 21B are plots of CCD signal v/s wavelengths. The plots indicate the vertically-binned signal from a 1 µM 6-FAM solution loaded into a glass microchannel (A) and a 1 µM fluorescein solution loaded into a plastic COC channel (B). The counts from the same microchannel filled with water are subtracted to take into account the autofluorescence of the glass or plastic microdevice. The power emitted from the system is 0.98 mW and 1.03 mW at 505 nm for glass and COC, respectively. This is obtained by supplying the two LEDs (placed in series) with a constant current of 0.74 A, which corresponds to a voltage of 7.0 V. Due to the choice of filters (emitter cut-on: T50 at 535 nm), only the tail of the fluorophore emission is observed (fluorescein: $8.^{em}_{max}$=513 at pH=13, 6-FAM: $8^{em}_{ma}x$=517 at pH=9. The signal-to-noise ratio is 87 for 1 µM 6-FAM in glass and 36 for 1 µM fluorescein in COC. The SNR is lower in glass because 6-FAM is known to photobleach faster than fluorescein. The detection limit parameters for glass and plastic CE microdevices are summarized in Table 2.

TABLE 2

| Device material | Fluorophore | Power at 505 nm | Maximum counts | signal-to-noise ratio |
| --- | --- | --- | --- | --- |
| Glass | 1 uM 6-FAM | 0.98 mW | 720 | 36 |
| COC | 1 uM fluorescein | 1.03 mW | 1750 | 87 |

For dynamic fluorescence measurements, glass microchannels are loaded with reagents similar to the reagents for the static measurement testing, but a first sequence of reagents are flushed through the microdevice to reduce the effect of the electroosmotic flow (EOF) that opposes the electrophoretic flow and results in peak distortion from a Gaussian shape and therefore loss of resolution. EOF arises from the re-equilibration of the electrical double layer arising from the surface charge of the microchannel walls after the perturbation caused by the migrating charges under the electric field. The EOF can be efficiently controlled by using a coating polymer matrix such as poly-N-hydroxyethylacrylamide (pHEA) dissolved in water at 0.1% w/v.

The DNA fragments are separated by electrophoretically migrating within a sieving polymer matrix such as POP-5™ (Applied Biosystems, Inc.), a mixture of polyacrylamides in an appropriate buffer, according to their size and interactions with the polymer network. After the pHEA coating has been applied, IX A.C.E.™ buffer (Amresco, Inc.) is flushed into the channel by vacuum followed by POP-5™. A 1 µM solution of a poly-adenine oligonucleotide labeled with 6-FAM is placed in the sample well and will be electrokinetically injected in the separation channel via a cross-injection geometry. 1× A.C.E.™ buffer is placed in the sample waste, buffer waste, and waste wells to ensure ionic conductivity in the whole device.

Figure 20A:
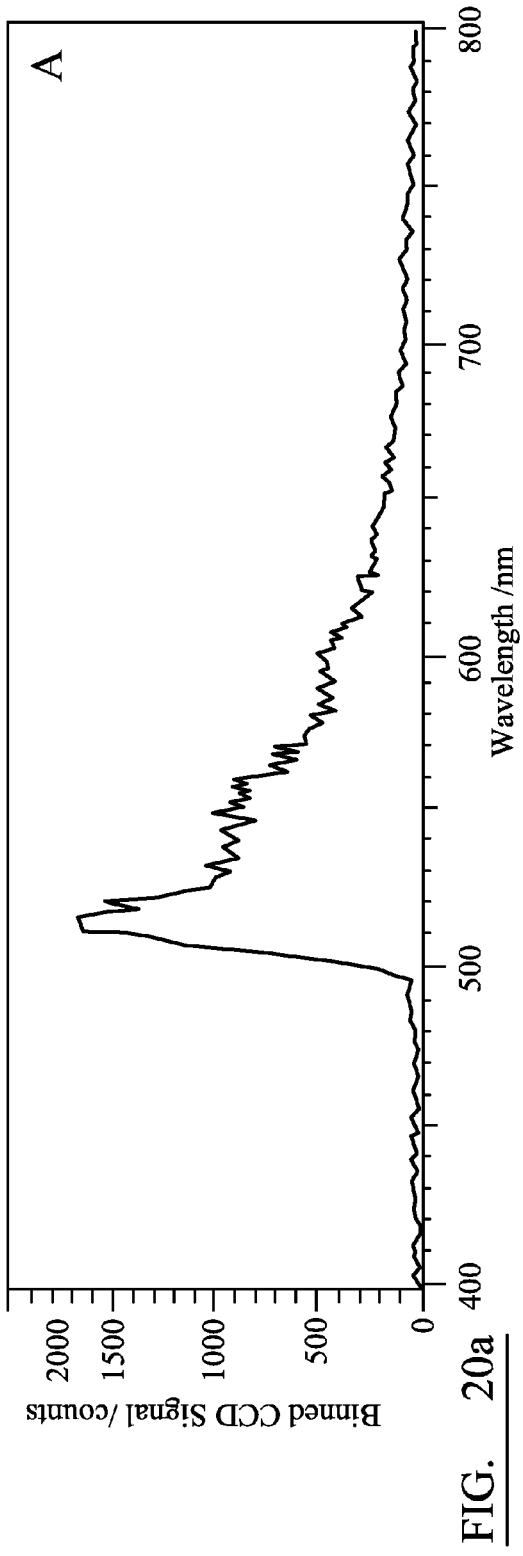
FIGS. 20a and 20b are plots of CCD signal v/s wavelengths for static fluorescence measurements.
Figure 20B:
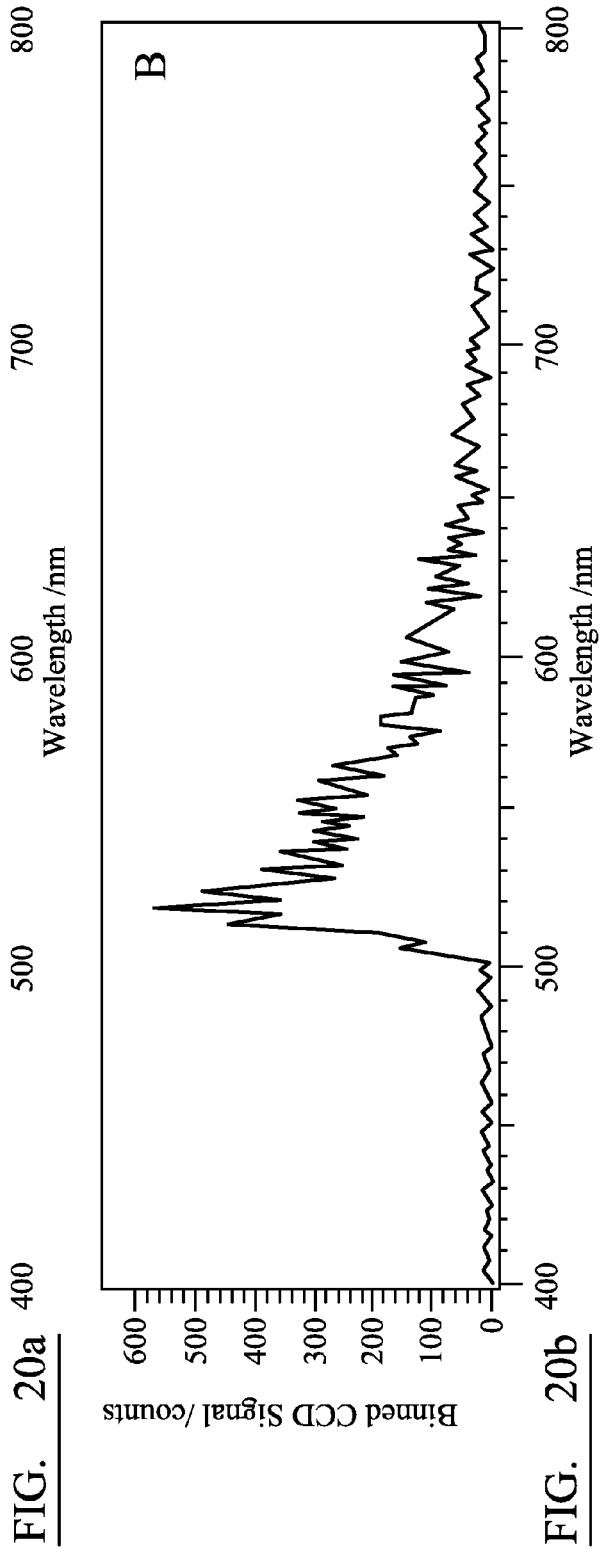
Figure 21:
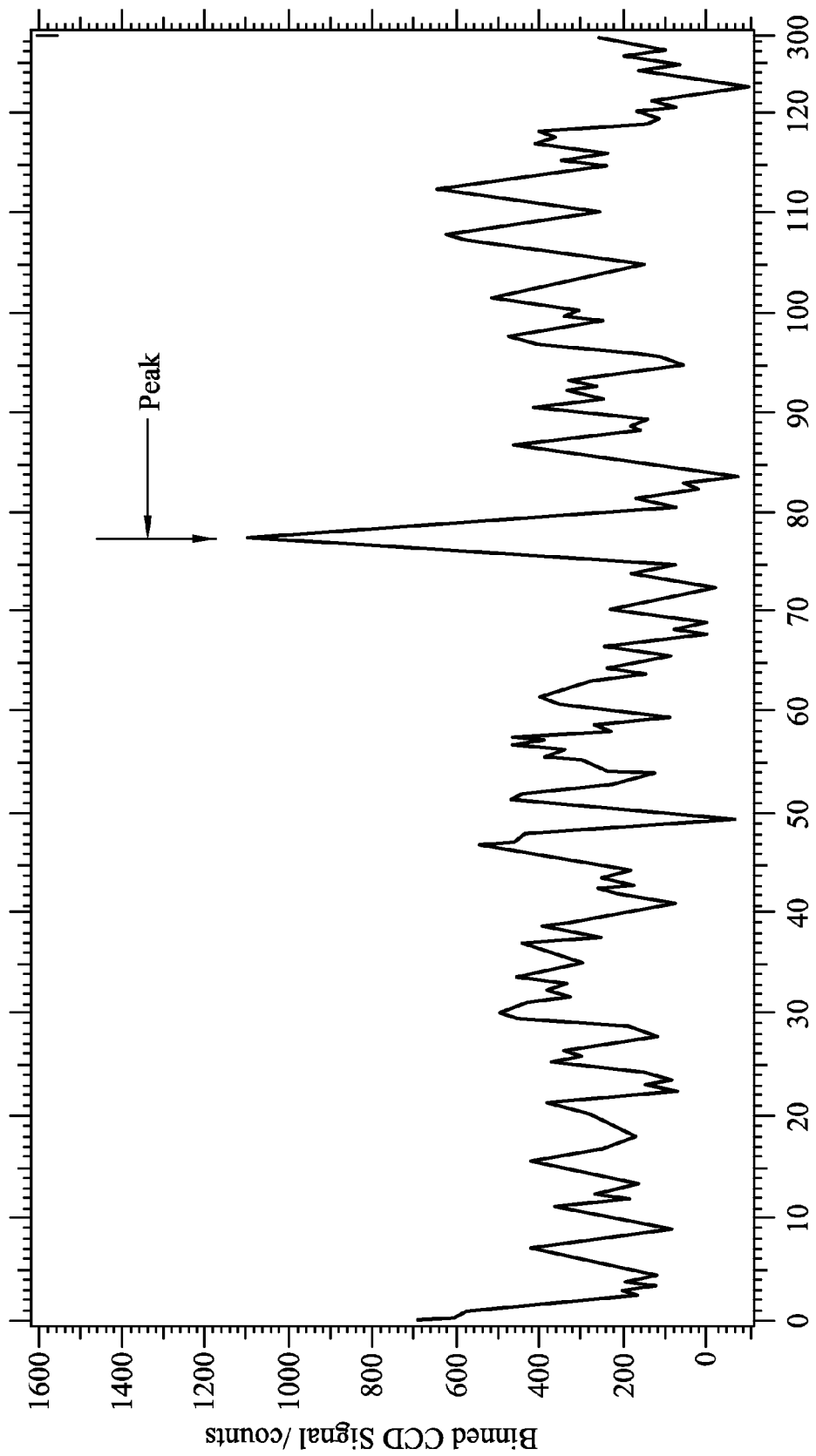
FIG. 21 is a plot of CCD signal v/s time for dynamic fluorescence measurements.

FIG. 21 is a plot of CCD signal v/s time for dynamic fluorescence measurements. The plot indicates fully binned CCD signal showing the peak corresponding to the elution of the 1 µM oligonucleotide (elution time, $t_{el}$=77 s) detected by the optical module. The nature of the peak is confirmed by the spectrum obtained in the CCD at t=77 s. It is similar to the peak shown in FIG. 20a. The signal-to-noise ratio of 10 can be improved by uniformly heating the chip to 50° C. The plot shows the result of the migration of the oligonucleotide while the LED-fibre assembly delivers about 980 μW at 505 nm. The two LEDs, placed in parallel, are supplied with 3.9 V (I=1.9 A) while the junction is kept at 15° C. The migration field in the separation channel is 110 V/cm.

In this manner, an optical excitation module capable of visualizing a 1 μM oligonucleotide migrating in a glass microchannel loaded with a sieving matrix is assembled and tested. The output fibre beam size and divergence, the power distribution in the beam exiting the fibre assembly as well as the output power stability over time approach the specifications of existing LIF setups. A modified epifluorescence microscope arrangement is used in conjunction with a lightweight compact fixed spectrograph built around ion-etched grating and aligned with a cooled Charge-Coupled Device (CCD) camera for added sensitivity. Fluorescent dyes such as fluorescein, 6-carboxyfluorescein (6-FAM) and rhodamine B can be detected in conventional plastic (cyclic olefin copolymer) and glass microchannels at submicromolar levels. A migrating single-stranded oligonucleotide DNA fragment (10-mer) labeled with 6-FAM can also be detected with high signal-to-noise ratio when electrophoretically migrated in the microchannels at 100 V/cm. LEDs operated in conjunction with Peltier elements controlled by a Proportional Integrative Derivative (PID) module can be used to replace bulky, expensive and power-consuming Argon ion lasers conventionally used in Laser Induced Fluorescence (LIF) Capillary Electrophoresis (CE) experiments. The LEDs in the system can be HP803-CN obtained from Roithner LaserTechnik GmBH or Luxeon Star series from Philips Lumiled Lighting Company that offer LEDs emitting at 505±15 nm with a full-width at half maximum of 20 nm. The LEDs are available with a Lambertian profile with a half-cone angle of 75°, which is not suited for microchip applications. However, these are high power LEDs with a nominal radiometric output power of 45 or 80 mW. When properly collimated, the available power becomes relevant to applications of DNA detection by CE.

While this specification contains many specifics, these should not be construed as limitations on the scope of the disclosure or of what may be claimed, but rather as descriptions of features specific to particular implementations of the disclosure. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

Thus, particular implementations of the disclosure have been described. Other implementations are within the scope of the following claims. For example, the actions recited in the claims can be performed in a different order and still achieve desirable results. In some implementations, the sharpness of the cut-on edge of the dichroic mirror can be improved and the lower wavelength $T_{50}$ can be shifted to a lower wavelength to improve the signal-to-noise ratio. In some implementations, the diodes can be operated in a pulsed AC mode where the "on" time is synchronized with the frame acquisition of the CCD camera, thereby also extending the lifetime of the LEDs. In some implementation, a customized LED array can be used that does not have the mold that yields divergent light. In some implementations, the collimation parts can be embedded in a rigid casing made, e.g., from black anodized aluminum.

In some implementations, the LED-based detection system described in this disclosure can be used as the microfluidic electrophoresis system that is described in the attachment, which is enclosed as part of the present disclosure.

5) Size Standards

The size standards used in the invention are beneficially stored within the formamide pump liquid.

The size standards may be provided according to the form detailed in International Patent Application no PCT/GB2009/002186, the contents of which are incorporated herein by reference, particularly with respect to the provision of and use of size standards which operate within a single CE channel, together with the sample being considered.

Instrument Performance

The result of the above embodiment is the provision of an instrument, cartridge and operating method which provides quick, reliable sample analysis, whilst doing so at a wide variety of locations and when operated by a wide variety of people.

By way of abilities are performance, the invention provides a fully integrated instrument capable of performing extraction, PCR, electrophoresis and analysis, whilst requiring minimal training and/or intervention by the user. In its optimum form, a fully automated system from start to finish is provided, the user simply needing to load the cartridge into the instrument and start it.

The modular nature of the instrument allows for upgrading of one or more modules without impact on the other modules. The data output format has been carefully selected to allow the analysis of the data outputted by a variety of existing analysis software applications, such as $I^3$ of Forensic Science Service Limited, and future software applications.

The end result of the analysis may be a profile for the sample and/or an indication of a match between the sample and a database recorded sample and/or other interpretation based data.

The use of a single cartridge type to handle a wide variety of sample from a wide variety of sources is beneficial. The methodology is able to handle samples originating from buccal swabs, cotton and other soft swabs, aqueous samples, clothing samples, cigarette butts, chewing gum and the like.

The methodology is also able to separate the useful DNA from residual cellular material, PCR inhibitors (such as ethanol, indigo etc) and chemical inhibitors.

The instrument is fully portable and so can be used in a wide variety of locations. The fully sealed and protected nature of the cartridge means that contamination is not a risk, even where the instrument is used outside of laboratory standard conditions. The instrument operates off a standard mains power supply, 110-240V, 50 Hz, using a conventional electric plug.

With respect to the overall time, from the sample receiving step 202, to the transmission away from the instrument in the data communication step 210, the embodiment described provides this process in a time period of 141 minutes. That time period can be reduced, including by the options and variables set out in the following paragraphs.

With respect to the sample receiving step 2002, the embodiment described provides this step in a time period of 2 minutes. Time periods of between 20 seconds and 5 minutes are easily achievable, depending upon the loading methodology used and the number of reagents or samples that need to be loaded.

With respect to the sample preparation step 202, the embodiment described provides this step in a time period of 24 minutes. That time period can be reduced by shortening the residence in one or more of the chambers, for instance the incubation chamber 358, and/or by reducing the time separation between a valve being activated and reliance on the outcome of the activation and/or by reducing the washing and/or elution volumes used. Time periods of between 15 to 30 minutes are easily achievable.

With respect to the sample amplification step 204, the embodiment described provides this step in a time period of 80 minutes. That time period can be reduced by shortening the number of cycles used, the duration of one or more parts of a cycle and the time period after introduction to the chamber and before PCR starts and/or after PCR finishes and before the sample is removed to the next stage. Again, the time separation between a valve being activated and reliance on the outcome of the activation is of significance. Time periods of between 60 to 120 minutes are easily achievable.

With respect to the electrophoresis step 206, the embodiment described provides this step in a time period of 15 minutes. That time period can be reduced by the use of higher voltages and/or faster migration media in the capillary and/or reductions in the sample introduction time. Time periods of between 1 to 60 minutes are easily achievable. This functionality is achieved in an instrument weighing less than 10 kg and occupying a footprint of less than 0.1 m$^2$.

Instrument Fields of Use

The structures and method discussed above are useful in the consideration of a wide variety of samples, over and above forensic samples. For instance, they can be used: the consideration of marker targets, diagnostic assays, disease markers, biobanking applications, STR based targets in transplants, identification of drug resistant microorganisms, blood testing, mutation detection, DNA sequencing and the like. Food analysis, pharmogenetics and pharmogenomics are also areas of use. A wide variety of uses in the medical and/or biotech field can make use of the invention.

The invention is also applicable in situations where familial relationships need to be determined from DNA, for instance paternity testing. Pedigree testing in animals is a further example.

The use of the invention in border control, security, customs situations and other governmental type uses is beneficial.

The invention claimed is:

1. An instrument for analysing a sample, the instrument including:
   one or more sample processors;
   electronics for operating the sample processors;
   a device to instrument interface; and
   a device location which recites the device in use;
   wherein one or more of the sample processors are provided on a device provided in the instrument, the device being provided in a device location in opposition to the device to instrument interface; and
   wherein the device to instrument interface includes components, the components including one or more heaters, one or more coolers, one or more sensors, and one or more magnets; and
   wherein the device provides all pumps for the sample processors.

2. An instrument according to claim 1 in which the device location is a planar location and the device to instrument interface includes a planar surface, the planar surface facing the device location.

3. An instrument according to claim 1 in which one or more of the heaters are provided by the instrument and the one or more heaters are printed onto the device to instrument interface.

4. An instrument according to claim 1 in which an actuator is provided by the instrument and the actuator provides reciprocating motion and is connected to a mounting for one or more magnets, the actuator having a first state and the actuator having a second state, the magnet being closer to the device location in the second state than in the first state.

5. An instrument according to claim 4 in which the device provides all of the materials which form all the moveable components for the processors, aside from the actuator for the magnet.

6. An instrument according to claim 1 in which the device to instrument interface is a printed circuit board.

7. An instrument according to claim 1 in which the device to instrument interface is connected to the operating electronics on the rear surface thereof.

8. An instrument according to claim 1 in which operating electronics are provided by the instrument and the operating electronics for the device to instrument interface include one or more power supplies, including a power supply connected to the electrical connections for a pump provided in the device.

9. An instrument according to claim 1 in which operating electronics are provided by the instrument and the operating electronics for the device to instrument interface include one or more power supply controllers and one or more heater controllers.

10. An instrument according to claim 1 in which the device provides all of the elements which move fluids within the processors.

11. An instrument according to claim 1 in which the device provides all of the materials which form the valves and seals in the device.

12. An instrument according to claim 1 in which the device has no electrical power sources.

13. An instrument according to claim 1 in which no material or elements enter the device from the device to instrument interface.

14. An instrument according to claim 1 in which the device to instrument interface provides all of the electrical power sources for the device and/or all of the variable magnetic field sources for the device and/or all of the fluid expansion drivers for the device and/or all the heaters for the device and/or all of the coolers for the device and/or all of the energy sources for the device.

15. An instrument according to claim 1 in which the device to instrument interface has no direct contact with the contents of the device.

16. An instrument according to claim 1 in which the interaction between the device and the device to instrument interface is limited to radiation of heat into the device and/or conduction of heat into the device and/or one or more electrical contacts and/or a magnetic field passing into or through the device.

17. An instrument according to claim 1 in which operating electronics are provided by the instrument and the operating electronics for the device to instrument interface include one or more temperature controllers and one or more actuator controllers.

18. An instrument according to claim 1 in which operating electronics are provided by the instrument and the operating electronics for the device to instrument interface include one or more sensor monitors and voltage controllers.

19. An instrument according to claim 1 in which the device provides all materials which form reagents for the processors.

20. An instrument according to claim 1 in which the device has no variable magnetic field source therein and fluid expansion drivers therein.

21. An instrument according to claim 1 in which the device has no heaters therein and no coolers therein.

22. An instrument according to claim 1 in which the device has no sensors therein and no energy sources therein.

* * * * *